United States Patent
Kim et al.

(10) Patent No.: US 10,118,965 B2
(45) Date of Patent: *Nov. 6, 2018

(54) COMPOSITIONS AND METHODS RELATED TO ANTI-EGFR ANTIBODY DRUG CONJUGATES

(71) Applicant: LegoChem Biosciences, Inc., Daejeon (KR)

(72) Inventors: Yong Zu Kim, Daejeon (KR); Yun Hee Park, Daejeon (KR); Hyo Jung Choi, Daejeon (KR); Ji Eun Jung, Daejeon (KR); Jeong Hee Ryu, Daejeon (KR); Ho Young Song, Daejeon (KR); Jeiwook Chae, Daejeon (KR); Chul-Woong Chung, Daejeon (KR)

(73) Assignee: LegoChem Biosciences, Inc., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/276,231

(22) Filed: Sep. 26, 2016

(65) Prior Publication Data
US 2017/0088621 A1  Mar. 30, 2017

Related U.S. Application Data

(60) Provisional application No. 62/232,662, filed on Sep. 25, 2015.

(51) Int. Cl.
*C07K 16/28* (2006.01)
*A61K 47/68* (2017.01)

(52) U.S. Cl.
CPC ...... *C07K 16/2863* (2013.01); *A61K 47/6817* (2017.08); *A61K 47/6849* (2017.08); *A61K 47/6889* (2017.08)

(58) Field of Classification Search
CPC ........ A61K 47/48646; A61K 47/48092; A61K 47/48338; A61K 47/48415; A61K 2039/505; C07K 16/32; C07K 2317/24
(Continued)

(56) References Cited

U.S. PATENT DOCUMENTS

| 5,112,739 A | 5/1992 | Meneghini et al. |
| 6,218,519 B1 | 4/2001 | Kenten et al. |

(Continued)

FOREIGN PATENT DOCUMENTS

| KR | 10-2015-0137015 | 12/2015 |
| KR | 10-2014-0192328 | 7/2016 |

(Continued)

OTHER PUBLICATIONS

Dunn, PJ. et al. Green Chemistry Principle #8. ACS What is Green Chemistry. Accessed from ACS Website on Jan. 8, 2016.*
(Continued)

*Primary Examiner* — Daniel R Carcanague
(74) *Attorney, Agent, or Firm* — Foley Hoag LLP; David P. Halstead; Lucas P. Watkins

(57) ABSTRACT

In some aspects, the invention relates to an antibody-drug conjugate, comprising an anti-epidermal growth factor receptor ("EGFR") antibody; a linker; and an active agent. The antibody-drug conjugate may comprise a self-immolative group. The linker may comprise an O-substituted oxime, e.g., wherein the oxygen atom of the oxime is substituted with a group that covalently links the oxime to the drug; and the carbon atom of the oxime is substituted with a group that covalently links the oxime to the antibody.

26 Claims, 17 Drawing Sheets

Specification includes a Sequence Listing.

(58) Field of Classification Search
USPC .................................................. 424/179.1
See application file for complete search history.

(56) References Cited

U.S. PATENT DOCUMENTS

| | | | |
|---|---|---|---|
| 8,039,273 | B2 | 10/2011 | Jeffrey |
| 8,568,728 | B2 | 10/2013 | Jeffrey |
| 9,919,057 | B2* | 3/2018 | Kim ................. A61K 47/69 |
| 9,993,568 | B2 | 6/2018 | Kim et al. |
| 2006/0088522 | A1* | 4/2006 | Boghaert ............. C07K 16/30 424/133.1 |
| 2012/0107332 | A1 | 5/2012 | Jeffrey |
| 2012/0308584 | A1 | 12/2012 | Kim et al. |
| 2014/0031535 | A1 | 1/2014 | Jeffrey |
| 2014/0032535 | A1 | 1/2014 | Singla |
| 2014/0161829 | A1 | 6/2014 | Kim et al. |
| 2014/0187756 | A1 | 7/2014 | Kim et al. |
| 2014/0286969 | A1 | 9/2014 | Tschoepe et al. |
| 2015/0105541 | A1 | 4/2015 | Kim et al. |
| 2016/0184451 | A1* | 6/2016 | Kim ............... A61K 47/48384 530/391.9 |
| 2016/0257709 | A1 | 9/2016 | Kline et al. |
| 2017/0088614 | A1* | 3/2017 | Kim ................. A61K 47/6889 |
| 2017/0095576 | A1* | 4/2017 | Kim ............... A61K 47/48646 |

FOREIGN PATENT DOCUMENTS

| | | | |
|---|---|---|---|
| WO | WO-2004050089 | A1 | 6/2004 |
| WO | WO-2011066418 | A1 | 6/2011 |
| WO | WO-2012/153193 | A2 | 11/2012 |
| WO | WO-2015/182984 | A1 | 12/2015 |
| WO | WO-2016/040684 | A1 | 3/2016 |
| WO | WO-2016/094517 | A1 | 6/2016 |
| WO | WO 2016108587 | * | 7/2016 |
| WO | WO-2017/051249 | A1 | 3/2017 |
| WO | WO-2017/051254 | A1 | 3/2017 |
| WO | WO 2017089890 | * | 6/2017 |
| WO | WO 2017089894 | * | 6/2017 |
| WO | WO 2017089895 | * | 6/2017 |

OTHER PUBLICATIONS

Wermuth, CG. Similarity in drugs: reflections on analogue design. Drug Discovery Today, 2006, vol. 11, p. 348.*

Lee; Angew.Chem. Int. Ed. 2015, 54 , 12020-12024. (Year: 2015).*

Yewale; Biomaterials 2013, 34, 8690-8707. (Year: 2013).*

Jeffrey; ACS Med. Chem. Lett. 2010, 1, 277-280. (Year: 2010).*

Behrens et al., "Methods for Site-specific Drug Conjugation to Antibodies," MAbs, 6(1): 46-53 (2014).

Chu et al., "Antibody-drug Conjugates for the Treatment of B-cell Non-Hodgkin's Lymphoma and Leukemia," Future Oncol, 9(3): 355-368 (2013).

Connolly et al., "Discovery of Orally Active 4-amino-6-arylaminopyrimidine-5-carbaldehyde Oximes with Dual EGFR and HER2 Inhibitory Activity," AACR 104th Annual Meeting, Abstract 2456 (2013).

Kim et al., "Synthesis of Bispecific Antibodies Using Genetically Encoded Unnatural Amino Acids," J Am Chem Soc, 134: 9918-9921 (2012).

McCombs et al., "Antibody Drug Conjugates: Design and Selection of Linker, Payload and Conjugation Chemistry," AAPS J, 17(2): 339-351 (2015).

Carey, FA. Organic Chemistry 6th Ed. McGraw Hill. 2006, chapter 1, p. 9.

Desbene, S. et al. Doxorubicin prodrugs with reduced cytotoxicity suited for tumour-specific activation. Anti-Cancer Drug Design. 1998,vol. 13,p. 955.

Grinda, M. et al., A Self-Immolative Dendritic Glucuronide Prodrug of Doxorubicin, Medicinal Chemistry Communications, (2012) vol. 3, No. 1, pp. 68-70.

International Search Report and Written Opinion from corresponding International Application Publication No. WO2015182984.

Lee et al., "Enzymatic Prenylation and Oxime Ligation for the Synthesis of Stable and Homogeneous Protein-Drug Conjugates for Targeted Therapy," Angew Chem Int Edit, 54:1-6 (2015).

Leong, KW. Biomaterials. El Sevier. Accessed on Sep. 26, 2016.

Merriam-Webster. Biomaterial Definition. Accessed on Sep. 26, 2016.

Extended European Search Report issued by the European Patent Office in corresponding Application No. EP 15799360.1, dated Dec. 21, 2017.

Jeffrey et al., Development and properties of β-glucuronide linkers for monoclonal antibody-drug conjugates, Bioconjugate Chem, 17:835 (2006).

Lartigue, "Antibody-Drug Conjugates: Guided Missiles Deployed Against Cancerous Cells," Oncology Live, p. 1 (2012).

Tranoy-Opalinski et al., "ß-Glucuronidase-responsive prodrugs for selective cancer chemotherapy: an update," Eur J Med Chem, 74:302-313 (2014).

* cited by examiner

When  part is carbamate,

When  part is ester,

A

1: Erbitux #140416
2: Erbitux #140725
3: Erbitux(LC) G7-CVIM #140814
4: Erbitux(HC) G7-CVIM #140725
5: Erbitux(LC, HC) G7-CVIM #140725

B

1 : Herceptin(LC) G7-CVIM #140417
2 : Erbitux #140725
3 : Erbitux(LC) G7-CVIM #140814
4 : Erbitux(HC) G7-CVIM #140725
5 : Erbitux(LC, HC) G7-CVIM #140725

A

B

C

A

B

C

A

B

COMPOSITIONS AND METHODS RELATED TO ANTI-EGFR ANTIBODY DRUG CONJUGATES

CROSS-REFERENCE TO RELATED APPLICATIONS

This application claims priority to U.S. Provisional Application No. 62/232,662 filed Sep. 25, 2015, which is hereby incorporated by reference in its entirety.

The instant application contains a Sequence Listing which has been submitted electronically in ASCII format and is hereby incorporated by reference in its entirety. Said ASCII copy, created on Nov. 11, 2016, is named LCH-003_01_SL.txt and is 1,066 bytes in size.

BACKGROUND

Antibody-drug conjugate (ADC) technology is a target-oriented technology, which allows for selective apoptosis of cancer cells. Typically, ADCs function by targeting cancer cells using the antibody and then releasing a toxic material (i.e., the drug) in a cell, thereby triggering cell death. Since ADC technology allows a drug to be accurately delivered to a target cancer cell and released under specific conditions, while minimizing collateral damage to healthy cells, ADC technology increases the efficacy of a therapeutic antibody and decreases the risk of an adverse reaction.

A basic structure of an antibody-drug conjugate is an "antibody-linker-low molecular drug (toxin)". The linker ideally allows the drug to exhibit an effect on a target cancer cell, e.g., after being separated from the antibody (for example, by enzyme-mediated hydrolysis), after the drug reaches a target cell. The linker also plays a functional role, by connecting the antibody and the drug. The efficacy and toxicity of the antibody-drug conjugate thereby depends, in part, on the stability of the linker, and thus, the linker plays an important role in drug safety.

The linkers of antibody-drug conjugates may be roughly classified as non-cleavable or cleavable. Many non-cleavable linkers are attached to antibodies using a thioether, comprising a cysteine of the antibody. The pendant drug generally cannot dissociate from the antibody in vivo. In the case of the widely-used thiol-maleimide method, however, the antibody-drug conjugate is unstable, which may result in dissociation of the drug from the conjugate before or after it reaches a target cell.

Cleavable linkers may be hydrolyzed, for example, by a cytosolic enzyme. A cleavable linker may comprise a disulfide bond, e.g., including a cysteine of the antibody. A disulfide linker, which allows for dissociation via a thiol exchange reaction, relies in part on the uptake of an antibody-drug conjugate into a target cell and the exposure of the disulfide to the cytosol, which is a reducing environment. Since various types of thiols (for example, albumin, and glutathione) are present in the blood, however, a drug may dissociate from the antibody prior to reaching its target.

In light of the foregoing, improved linkers for antibody-drug conjugates are desirable.

SUMMARY

In some aspects, the invention relates to anti-epidermal growth factor receptor (EGFR) antibody-drug conjugates (ADCs). The antibody-drug conjugate may comprise a self-immolative group, e.g., for use in separating an active agent from the antibody and linker.

In some embodiments, the invention relates to an antibody-drug conjugate, comprising an anti-epidermal growth factor receptor ("EGFR") antibody, a linker, and an active agent (e.g., a drug). The linker may comprise an O-substituted oxime. In preferred embodiments, the oxygen atom of the oxime is substituted with a group that covalently links the oxime to the active agent, and the carbon atom of the oxime is substituted with a group that covalently links the oxime to the antibody. In some embodiments, the carbon atom of the oxime is substituted with a group that covalently links the oxime to the active agent, and the oxygen atom of the oxime is substituted with a group that covalently links the oxime to the antibody. In some embodiments, the linker does not comprise an oxime. For example, the linker may comprise a substituted triazole instead of an oxime.

In some embodiments, the invention relates to an antibody-drug conjugate represented by Formula (I), comprising an antibody (A) having binding specificity for EGFR, a linker, and an active agent (B), such as a drug, a toxin, a ligand, a detection probe, or the like, having a desired function or activity.

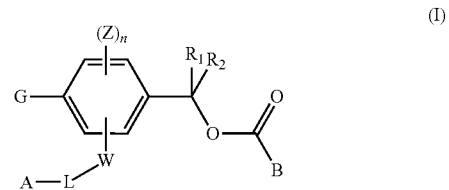

(I)

wherein

G is a residue of a sugar or sugar acid, preferably a residue of glucuronic acid or a derivative thereof;

A represents the anti-EGFR antibody;

B represents the active agent, such as a drug;

W represents an electron-withdrawing group, preferably —C(O)NR'—, where C(O) is bonded to the phenyl ring and NR' is bonded to L;

each Z independently represents $(C_1-C_8)$alkyl, halogen, cyano, or nitro, preferably hydrogen;

n is an integer of 0 to 3;

L comprises a chain of 3 to 100 atoms that covalently links A to W; and $R_1$ and $R_2$ are each independently hydrogen, $(C_1-C_8)$alkyl, or $(C_3-C_8)$cycloalkyl, preferably hydrogen, or $R_1$ and $R_2$ taken together with the carbon atom to which they are attached form a $(C_3-C_8)$cycloalkyl ring.

In some aspects, the invention relates to a pharmaceutical composition comprising an antibody-drug conjugate. In some aspects, the invention relates to a method of treating cancer in a subject, comprising administering to the subject a pharmaceutical composition comprising an antibody-drug conjugate.

In some aspects, the invention relates to a method for making an antibody-drug conjugate. The method may comprise reacting a biomolecule with a prodrug. For example, the biomolecule may comprise an anti-EGFR antibody and a ketone or aldehyde, the prodrug may comprise an alkoxyamine, and the reaction may produce an oxime, thereby covalently linking the antibody to the prodrug. The method may comprise isoprenylating an antibody. For example, the antibody may be an anti-EGFR antibody, the antibody may comprise an isoprenylation sequence, isoprenylating the antibody may comprise incubating the antibody with an isoprenoid transferase and an isoprenoid transferase substrate, and the substrate may comprise a prodrug. Thus, incubating the antibody with the isoprenoid transferase and the substrate may covalently link the antibody to the prodrug.

BRIEF DESCRIPTION OF THE DRAWINGS

FIG. 8(A) and FIG. 8(B) shows SDS-PAGE analyses of various antibody derivatives. In FIG. 8(A), the left and right gel images depict cetuximab derivatives run under non-reducing conditions and reducing conditions, respectively. FIG. 8(b) shows images that depict cetuximab derivatives, run under reducing conditions, imaged for either the fluorophore nitrobenzoxadiazole (NBD) (left), added by prenylating each antibody, or for protein (Coomassie blue) (right). Cetuximab is denoted by "Erbitux"; cetuximab with the linker/prenylation peptide sequence GGGGGGGCVIM (SEQ ID NO: 1) appended to each light chain is denoted by "Erbitux(LC) G7-CVIM"; cetuximab with the linker/prenylation peptide sequence GGGGGGGCVIM (SEQ ID NO: 1) appended to each heavy chain is denoted by "Erbitux(HC) G7-CVIM"; and cetuximab with the linker/prenylation peptide sequence GGGGGGGCVIM (SEQ ID NO: 1) appended to each light chain and each heavy chain is denoted by "Erbitux(LC, HC) G7-CVIM". For the bottom gel, the antibodies were prenylated with the 3,7-dimethyl-8-(7-nitrobenzo[1,2,5]oxadiazol-4-ylamino)-octa-2,6-diene-1-pyrophosphate (NBD-GPP) substrate using farnesyltransferase, which specifically targets prenylation of free cysteine thiols in a C-terminal CVIM amino acid sequence (SEQ ID NO: 2).

In FIG. 9(A), Cetuximab with the linker/prenylation peptide sequence GGGGGGGCVIM (SEQ ID NO: 1) appended to each light chain is denoted by "EG7(LC)"; in FIG. 9(B), cetuximab with the linker/prenylation peptide sequence GGGGGGGCVIM (SEQ ID NO: 1) appended to each heavy chain is denoted by "EG7(HC)"; in FIG. 9(C), cetuximab with the linker/prenylation peptide sequence GGGGGGGCVIM (SEQ ID NO: 1) appended to each light chain and each heavy chain is denoted by "EG7 (LC&HC)"; and, in FIGS. 9(A), (B), and (C), antibodies prenylated with the LCB14-0606 substrate are denoted by "-0606PR".

FIG. 12(A) shows results for in vitro cytotoxicity assays performed with MCF-7 cells, which express low levels of EGFR, HCC-827 cells, which express high levels of EGFR, and A431 cells, which express an intermediate level of EGFR. Serial dilutions of the anti-EGFR antibody-drug conjugate ADC14-0810 (batch #150129), unconjugated parent antibody cetuximab (Erbitux®), and unconjugated drug (toxin MMAF-OMe) were added to the wells of 96-well plates containing the different cell lines. In FIGS. 12(B) and 12(C), Cetuximab displayed activity against HCC-827 (FIG. 12(B)) cells and A431 cells (FIG. 12(C)), but its IC$_{50}$ was out-of-range for the assay (>100 nM). MMAF-OMe displayed non-specific cytotoxicity against each cell line. Only the antibody-drug conjugate ADC14-0810 (cetuximab conjugated to MMAF-Ome, as described herein) displayed specificity for both the intermediate and high-level EGFR-expressing cells (HCC-827 and A431, respectively) without displaying appreciable cytotoxicity against the low level EGFR-expressing cell line (MCF-7).

FIG. 14(A) and FIG. 14(B) show the drug:antibody ratio for the antibody-drug conjugate ADC14-0810 in rat plasma after injecting the conjugate into rats. ADC14-0810 comprises cetuximab and one MMAF moiety linked to each of cetuximab's two light chains, and thus, the initial ratio was about 2.0. The concentration of both the antibody and MMAF decreased over the course of the 28-day experiment (FIG. 14A), and the ratio of drug to antibody also decreased (FIG. 14B).

DETAILED DESCRIPTION

Figure 1:
FIG. 1 illustrates an active drug release mechanism from a β-glucuronide based linker.
Figure 1:
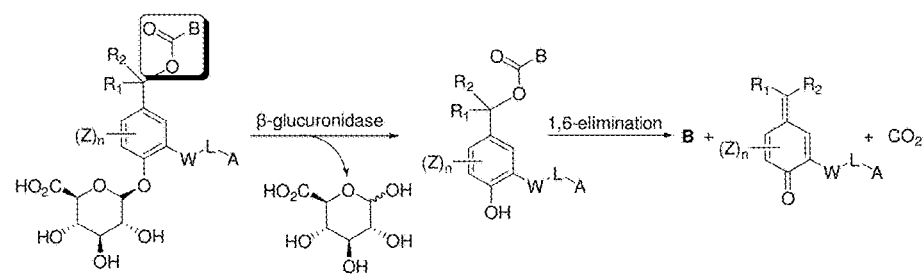
Figure 1:
Figure 1:
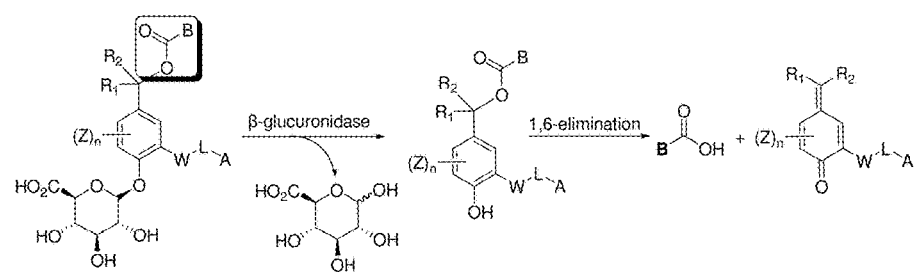

In some aspects, the invention relates to anti-EGFR antibody-drug conjugates (ADCs). The antibody-drug conjugate may comprise a self-immolative group, e.g., for use in separating an active agent from the ADC.

In some embodiments, the invention relates to an antibody-drug conjugate, comprising an anti-EGFR antibody, a linker, and an active agent (e.g., a drug). The linker may comprise an O-substituted oxime. In preferred embodiments, the oxygen atom of the oxime is substituted with a group that covalently links the oxime to the active agent, and the carbon atom of the oxime is substituted with a group that covalently links the oxime to the antibody. In some embodiments, the carbon atom of the oxime is substituted with a group that covalently links the oxime to the active agent, and the oxygen atom of the oxime is substituted with a group that covalently links the oxime to the antibody. In some embodiments, the linker does not comprise an oxime. For example, the linker may comprise a substituted triazole instead of an oxime.

An ADC may be represented by Formula (I), comprising an antibody (A) having binding specificity for EGFR, a linker, and an active agent (B), such as a drug, a toxin, a ligand, a detection probe, or the like, having a desired function or activity.

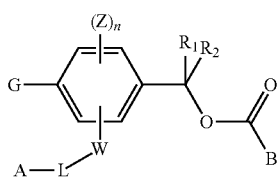

(I)

wherein
G is a residue of a sugar or sugar acid, preferably a residue of glucuronic acid or a derivative thereof;
A represents the anti-EGFR antibody;
B represents the active agent, such as a drug;
W represents an electron-withdrawing group, preferably —C(O)NR'—, where C(O) is bonded to the phenyl ring and NR' is bonded to L;
each Z independently represents $(C_1-C_8)$alkyl, halogen, cyano, or nitro, preferably hydrogen;
n is an integer of 0 to 3;
L comprises a chain of 3 to 100 atoms that covalently links A to W; and
$R_1$ and $R_2$ are each independently hydrogen, $(C_1-C_8)$alkyl, or $(C_3-C_8)$cycloalkyl, preferably hydrogen, or $R_1$ and $R_2$ taken together with the carbon atom to which they are attached form a $(C_3-C_8)$cycloalkyl ring.

The moieties connecting A and B, taken together (i.e., from L to OC(=O)), form the linker.

The linker may comprise residue of a sugar or sugar acid, e.g., coupled by a bond susceptible to enzymatic cleavage, such as a glycosidic bond. This residue is represented by G in Formula (I). The sugar or sugar acid may be glucuronic acid, or a derivative thereof, which is capable of being cleaved from the ADC by a β-glucuronidase. The residue of glucuronic acid, or derivative thereof, may be represented by Formula (II):

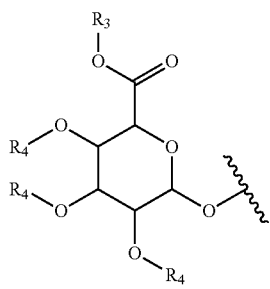

(II)

wherein $R_3$ is hydrogen or a carboxyl protecting group, preferably hydrogen, and each $R_4$ is independently hydrogen or a hydroxyl protecting group, preferably hydrogen.

A carboxyl protecting group may be any suitable protecting group for masking a carboxylic acid, e.g., in organic synthesis, such as methyl, methoxymethyl, methylthiomethyl, tetrahydropyranyl, benzyloxymethyl, phenacyl, N-phthalimidomethyl, 2,2,2-trichloroethyl, 2-haloethyl, 2-(p-toluenesulfonyl)ethyl, t-butyl, cinnamyl, benzyl, triphenylmethyl, bis(o-nitrophenyl)methyl, 9-anthrylmethyl, 2-(9,10-dioxo)anthrylmethyl, piperonyl, 2-trimethylsilylethyl, trimethylsilyl, or t-butyldimethylsilyl. In some embodiments, the entire moiety $R_3$—OC(=O)— is replaced by a carboxyl-masking moiety such as 2-alkyl-1,3-oxazolinyl.

A hydroxyl protecting group may be any suitable protecting group suitable for masking a hydroxyl group, e.g., in organic synthesis, such as acetyl, methyl, ethoxyethyl, benzoyl, benzyl, 4-methoxybenzyl, 3,4-dimethoxybenzyl, tetrahydropyranyl (THP), tetrahydrofuranyl (THF), tert-butyldimethylsilyl (TBDMS), trimethylsilyl (TMS), triethylsilyl (TES), triisopropylsilyl (TIPS), tert-butyldiphenylsilyl (TBDPS), tri-isopropylsilyloxymethyl (TOM), β-methoxyethoxymethyl (MEM), methoxymethyl (MOM), allyl, or trityl.

The electron withdrawing group W may be —C(O)—, —C(O)NR'—, —C(O)O—, —SO$_2$NR'—, —P(O)R"NR'—, —SONR'—, or —PO$_2$NR'—, preferably —C(O)NR'—, and R' and R" may be each independently hydrogen, $(C_1-C_8)$alkyl, $(C_3-C_8)$cycloalkyl, $(C_1-C_8)$alkoxy, $(C_1-C_8)$alkylthio, mono- or di-$(C_1-C_8)$alkylamino, $(C_3-C_{20})$heteroaryl or $(C_6-C_{20})$aryl. In such embodiments, W is preferably oriented such that the carbonyl, phosphoryl, sulphonyl, or sulphinyl group is directly bound to the phenyl ring.

The linker may comprise an electron withdrawing group, selected from —C(O)—, —C(O)NR'—, —C(O)O—, —SO$_2$NR'—, —P(O)R"NR'—, —SONR'—, and —PO$_2$NR'—, preferably —C(O)NR'—, wherein R' and R" may be each independently hydrogen, $(C_1-C_8)$alkyl, $(C_3-C_8)$cycloalkyl, $(C_1-C_8)$alkoxy, $(C_1-C_8)$alkylthio, mono- or di-$(C_1-C_8)$alkylamino, $(C_3-C_{20})$heteroaryl or $(C_6-C_{20})$aryl.

L and/or the linker may comprise a substituted or unsubstituted alkylene having 1 to 50 carbon atoms and satisfy at least one, preferably at least two, of the following (i) to (iv):
  (i) the alkylene includes at least one unsaturated bond, preferably 3 or 4 double bonds and no triple bonds,
  (ii) the alkylene includes at least one heteroarylene,
  (iii) at least one carbon atom of the alkylene is replaced by one or more heteroatoms selected from nitrogen (N), oxygen (O), and sulfur (S), preferably at least one nitrogen and at least one oxygen (e.g., as in an oxime), and
  (iv) the alkylene is substituted with one or more alkyls having 1 to 20 carbon atoms, preferably 2 or 3 methyls.

For example, L and/or the linker may comprise at least one isoprenyl derivative unit, preferably two isoprenyl derivative units, each represented by Formula (III), which is preferably recognizable by an isoprenoid transferase, e.g., as part of a product or substrate of the isoprenoid transferase.

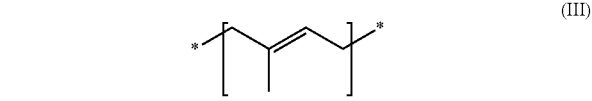

(III)

L and/or the linker may comprise a binding unit formed by a 1,3-dipolar cycloaddition reaction, hetero-Diels-Alder reaction, nucleophilic substitution reaction, non-aldol type carbonyl reaction, addition to a carbon-carbon multiple bond, oxidation reaction, or click reaction. A binding unit may be formed by a reaction between an acetylene and azide, or a reaction between an aldehyde or ketone group and hydrazine or alkoxyamine; such binding units may be represented by Formula (A), (B), (C), or (D).

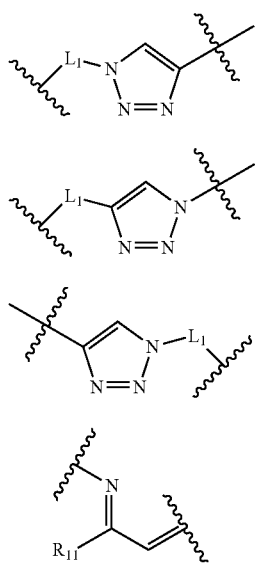

$L_1$ is a single bond or alkylene having 1 to 30 carbon atoms, preferably 12 carbon atoms;
$R_{11}$ is hydrogen or an alkyl having 1 to 10 carbon atoms, preferably methyl; and
$L_2$ is an alkylene having 1 to 30 carbon atoms, preferably 11 carbon atoms. In some embodiments, $L_1$ and/or $L_2$ may comprise at least one isoprenyl derivative unit, represented by Formula (III), preferably two isoprenyl derivative units. $L_2$ may consist of at least one isoprenyl derivative unit, represented by Formula (III), preferably two isoprenyl derivative units.

Click chemistry reactions may be carried out under mild conditions, which can be performed in the presence of an antibody without denaturing the antibody. A click chemistry reaction shows high reaction specificity. Therefore, even though antibodies have various functional groups (for example, amines, carboxyls, carboxamides, and guanidiniums), a click chemistry reaction may be performed, for example, without affecting the amino acid side chains of the antibody. A click chemistry reaction between an azide group and an acetylene group, for example, may occur in the presence of an antibody without modifying the amino acid side chain functional groups of the antibody. Further, a click chemistry reaction may precisely target a specific functional group, such as functional groups rarely found in nature, regardless of the nature of the reactants. In some cases, the reactants are selected to improve overall reaction efficiency. For example, an azide-acetylene click chemistry reaction may produce triazole with a high yield (see, e.g., Hia, R K et al., Chem. Rev., 109:5620 (2009); Meldal, M & Tornoe, C W, Chem Rev., 108:2952 (2008); Kolb, H C et al., Angew. Chemie Int. Ed. Engl., 40:2004 (2001), each of which is hereby incorporated by reference).

Azide and acetylene functional groups do not exist in natural proteins. Thus, none of the amino acid side chains, N-terminal amines, or C-terminal carboxyls should be affected by a click chemistry reaction that utilizes these functional groups.

The L moiety of Formula I and/or the linker may further include a connection unit represented by $-(CH_2)_r(V(CH_2)_p)_q-$ or $-(CH_2CH_2X)_w-$, wherein
V is a single bond, $-O-$, $-S-$, $-NR_{21}-$, $-C(O)NR_{22}-$, $-NR_{23}C(O)-$, $-NR_{24}SO_2-$, or $-SO_2NR_{25}-$, preferably $-O-$;
X is $-O-$, $(C_1-C_8)$alkylene, or $-NR_{21}-$, preferably $-O-$;
$R_{21}$ to $R_{25}$ are each independently hydrogen, $(C_1-C_6)$alkyl, $(C_1-C_6)$alkyl$(C_6-C_{20})$aryl, or $(C_1-C_6)$alkyl$(C_3-C_{20})$heteroaryl, preferably hydrogen;
r is an integer of 1 to 10, preferably 3;
p is an integer of 0 to 10, preferably 1;
q is an integer of 1 to 10, preferably 1; and
w is an integer of 1 to 10, preferably 3.

L and/or the linker preferably comprises the binding unit represented by Formula (A), (B), (C), or (D) and the connection unit represented by $-(CH_2)_r(V(CH_2)_p)_q-$ or $-(CH_2CH_2X)_w-$.

For example, L is preferably represented by one of the following two structures, and thus, the linker may comprise one of the following two structures:

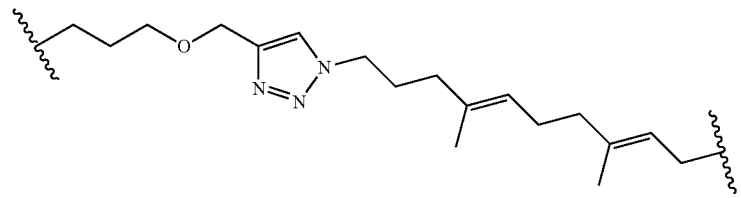

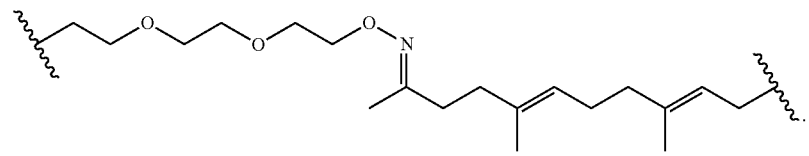

L and/or the linker may comprise

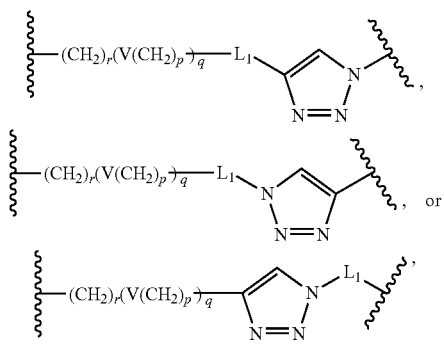

wherein
V represents a single bond, —O—, —S—, —C(O)NR$_{22}$—, —NR$_{23}$C(O)—, —NR$_{24}$SO$_2$—, or —SO$_2$NR$_{25}$—, preferably —O—;
R$_{21}$ to R$_{25}$ represents each independently hydrogen, (C$_1$-C$_6$) alkyl, (C$_1$-C$_6$)alkyl(C$_6$-C$_{20}$)aryl, or (C$_1$-C$_6$)alkyl(C$_3$-C$_{20}$) heteroaryl;
r is an integer of 1 to 10, preferably 3;
p is an integer of 0 to 10, preferably 1;
q is an integer of 1 to 10, preferably 1; and
L$_1$ is a single bond.

In preferred embodiments, the antibody comprises an isoprenylation sequence capable of being recognized by an isoprenoid transferase. That is, at least one C-terminus of the antibody may comprise an isoprenylation sequence capable of being recognized by an isoprenoid transferase (e.g., as a substrate, for example, prior forming the antibody-drug conjugate, or as a product of an isoprenoid transferase, for example, after forming the antibody-drug conjugate). The antibody may further comprise a spacer, such as an amino acid or a stretch of amino acids that links a peptide chain of the antibody to the isoprenylation sequence. The spacer may consist of 1 to 20 consecutive amino acids. Glycine and proline are preferred amino acids for the spacer, and may be used in any combination. The antibody may comprise an addition or deletion at a carboxy terminus, e.g., relative to a form of the antibody not included in an ADC.

Examples of isoprenoid transferases include farnesyl protein transferase (FTase) and geranylgeranyl transferase (GGTase), which can catalyze the transfer of a farnesyl or geranylgeranyl group to at least one C-terminal cysteine of a target protein. A GGTase may be classified as either GGTase I or GGTase II. FTase and GGTase I may recognize a CAAX motif, and GGTase II may recognize a XXCC, XCXC, or CXX motif, wherein C represents cysteine, A represents an aliphatic amino acid (e.g., isoleucine, valine, methionine, leucine), and each X independently represents, for example, glutamine, glutamate, serine, cysteine, methionine, alanine, or leucine (see Nature Rev. Cancer, 5(5):405-12 (2005); Nature Chemical Biology 17:498-506 (2010); Lane K T, Bees L S, J. Lipid Research, 47:681-699 (2006); Kasey P J, Seabra M C, J. Biological Chemistry, 271(10): 5289-5292 (1996), each of which is hereby incorporated by reference in its entirety).

Isoprenoid transferases from various sources may be used. For example, the isoprenoid transferase may be obtained from a human, animal, plant, bacteria, virus, or other source. In some embodiments, a naturally occurring isoprenoid transferase is used. In some embodiments, a naturally-modified or artificially-modified isoprenoid transferase may be used. For example, the isoprenoid transferase may comprise one or more amino acid substitutions, additions, and/or deletions, and/or the isoprenoid transferase may be modified by the addition of at least one of Histidine-tag, GST, GFP, MBP, CBP, Isopeptag, BCCP, Myc-tag, Calmodulin-tag, FLAG-tag, HA-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty-tag, and the like.

Isoprenoid transferases recognize an isosubstrate and/or a substrate. The term isosubstrate refers to a substrate analog comprising a chemical modification. Isoprenoid transferases can alkylate a specific amino acid motif (for example, a CAAX motif) at the C-terminus of an antibody (see, e.g., Duckworth, B P et al., ChemBioChem, 8:98 (2007); Uyen T T et al., ChemBioChem, 8:408 (2007); Labadie, G R et al., J. Org. Chem., 72(24):9291 (2007); Wollack, J W et al., ChemBioChem, 10:2934 (2009), each of which is hereby incorporated by reference). A functionalized antibody may be produced using an isoprenoid transferase and an isosubstrate, which may alkylate a C-terminal cysteine.

The isosubstrate may be, for example, the compound of Formula IV.

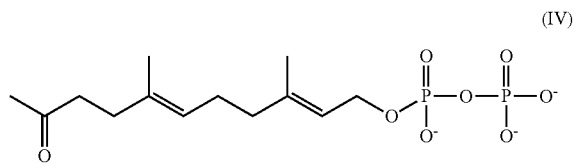 [SMILES: CC(=O)CC/C(C)=C/CC/C(C)=C/COP(=O)([O-])OP(=O)([O-])[O-]]

(IV)

The cysteine of a C-terminal CAAX motif may be bound to an isosubstrate using an isoprenoid transferase. In some embodiments, AAX may subsequently be removed by a protease. The cysteine may optionally be methylated at the carboxyl terminus, e.g., by an enzyme (see, e.g., Bell, I M, J. Med. Chem., 47(8):1869 (2004), which is hereby incorporated by reference).

The antibody-drug conjugates of the invention may be prepared using any method known in the art, including molecular biology and cell biology methods. For example, transient or stable transfection methods may be used. Genetic sequences encoding a specific amino acid motif capable of being recognized by an isoprenoid transferase may be inserted into a known plasmid vector using standard PCR and/or ligation technologies so as to express an antibody having the specific isoprenylation sequence at a C-terminus thereof. An antibody having at least one isoprenylation sequence capable of being recognized by the isoprenoid transferase may thus be expressed in a suitable host, e.g., a CHO cell or in E coli.

The term "antibody" refers to an immunoglobulin molecule that recognizes and specifically binds to EGFR through at least one antigen recognition site within a variable region of the immunoglobulin molecule. The term "EGFR" refers epidermal growth factor receptor. As used herein, the term "antibody" includes intact polyclonal antibodies, intact monoclonal antibodies, antibody fragments (for example, Fab, Fab', F(ab')$_2$, Fd, and Fv fragments), single chain Fv (scFv) mutants, multispecific antibodies such as bispecific antibodies generated from two or more intact antibodies, chimeric antibodies, humanized antibodies, human antibodies, fusion proteins including an antigen determination portion of an antibody, and any other modified immunoglobulin molecule including an antigen recognition site so long as the antibodies specifically bind to EGFR. The antibody may be any of the five major classes of immunoglobulins: IgA, IgD, IgE, IgG, and IgM, or subclasses (isotypes) thereof (for example, IgG1, IgG2, IgG3, IgG4, IgA1, and IgA2), based on the identity of its heavy chain constant domains, referred to as alpha, delta, epsilon, gamma, and mu, respectively. The different classes of immunoglobulins have different and well-known subunit structures and three-dimensional configurations. The term "antibody" does not refer to molecules that do not share homology with an immunoglobulin sequence. For example, the term "antibody" as used herein does not include "repebodies".

The term "antibody fragment" refers to a portion of an intact antibody and refers to antigenic determining variable regions of an intact antibody. Examples of antibody fragments include Fab, Fab', F(ab')$_2$, Fd, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant or epitope. This contrasts with polyclonal antibodies that typically include different antibodies directed against a variety of different antigenic determinants. The term "monoclonal antibody" includes antibody fragments (such as Fab, Fab', F(ab')$_2$, Fd, Fv), single chain (scFv) mutants, fusion proteins including an antibody portion, and any other modified immunoglobulin molecule including an antigen recognition site as well as both intact and full-length monoclonal antibodies, but are not limited thereto. Additionally, "monoclonal antibody" refers to such antibodies made in any number of methods, including but not limited to hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. In general, humanized antibodies are human immunoglobulins in which residues from complementary determining region (CDR) are replaced by residues from CDR of a non-human species (e.g., mouse, rat, rabbit, and hamster) having the desired specificity, affinity, and capability (see, e.g., Jones et al., Nature, 321:522-525 (1986); Riechmann et al., Nature, 332:323-327 (1988); Verhoeyen et al., Science, 239:1534-1536 (1988)). In some instances, Fv framework region (FR) residues of a human immunoglobulin are replaced with the corresponding residues in an antibody from a non-human species having a desired specificity, affinity, and/or binding capability (i.e., which targets EGFR). The humanized antibody may be further modified by the substitution of additional residues either in the Fv framework region and/or within the replaced non-human residues to refine and optimize antibody specificity, affinity, and/or binding capability. In general, a humanized antibody includes substantially all of at least one, and typically two or three, variable domains containing all or substantially all of the CDRs that correspond to the non-human immunoglobulin whereas all or substantially all of the framework regions (FRs) have those of a human immunoglobulin consensus sequence. The humanized antibody may also include at least a portion of an immunoglobulin constant region or domain (Fc), typically that of a human immunoglobulin. Examples of methods used to generate humanized antibodies are described in U.S. Pat. No. 5,225,539, hereby incorporated by reference.

The term "human antibody" as used herein refers to an antibody encoded by a human nucleotide sequence or an antibody having an amino acid sequence corresponding to an antibody produced by a human using any technique known in the art. This definition of the human antibody includes intact full-length antibodies and/or fragments thereof.

The term "chimeric antibody" refers to an antibody wherein an amino acid sequence of an immunoglobulin molecule is derived from two or more species, one of which is preferably human. In general, variable regions of both light and heavy chains correspond to variable regions of antibodies derived from one species of mammals (e.g., mouse, rat, rabbit, etc) with the desired specificity, affinity, and capability, while constant regions are homologous to the sequences in antibodies derived from another species (usually human), e.g., to avoid eliciting an immune response in that species.

The terms "epitope" and "antigenic determinant" are used interchangeably herein and refer to that portion of an antigen capable of being recognized and specifically bound by a particular antibody. When the antigen is or comprises a polypeptide or protein, epitopes may be formed from contiguous and/or non-contiguous amino acids, e.g., juxtaposed by secondary, tertiary, and/or quaternary folding of a protein. Epitopes formed from contiguous amino acids are typically retained upon protein denaturing, whereas epitopes formed by tertiary folding may be lost upon protein denaturing. An epitope typically includes 3 or more, 5 or more, or 8 to 10 or more amino acids in a unique spatial conformation. In preferred embodiments, an epitope is a portion of an EGFR, preferably an extracellular portion of an EGFR, preferably a human EGFR.

An antibody "specifically binds" to an epitope or antigenic molecule, which means that the antibody interacts or associates more frequently, more rapidly, with greater duration, with greater affinity, or with some combination of the foregoing to an epitope or antigenic molecule than alternative substances, including unrelated proteins. In specific embodiments, "specifically binds" means, for instance, that an antibody binds to a protein with a $K_D$ of about 0.1 mM or less, but more usually, less than about 1 µM. In specific embodiments, "specifically binds" means that an antibody binds to a protein at times with a $K_D$ of about 0.1 µM or less, and at other times, with a $K_D$ of about 0.01 µM or less. Because of the sequence identity between homologous proteins in different species, specific binding may include an antibody recognizing a particular protein in more than one species. It is understood that an antibody or binding residue that specifically binds to a first target may or may not specifically bind to a second target. As described above, "specific binding" does not necessarily require (although it may include) exclusive binding, that is, binding to a single target. Generally, but not necessarily, the term binding used herein means specific binding.

The antibodies, including fragments/derivatives thereof and monoclonal antibodies, may be obtained using methods known in the art (see, e.g., McCafferty et al., Nature 348: 552-554 (1990); Clackson et al., Nature 352:624-628; Marks et al., J. Mol. Biol. 222:581-597 (1991); Marks et al., Bio/Technology 10:779-783 (1992); Waterhouse et al., Nucleic Acids Res. 21:2265-2266 (1993); Morimoto et al., J Biochemical & Biophysical Methods 24:107-117 (1992); Brennan et al., Science 229:81 (1985); Carter et al., Bio/Technology 10:163-167 (1992); Kohler et al., Nature 256: 495 (1975); Kilpatrick et al., Hybridoma 16(4):381-389 (1997); Wring et al., J. Pharm. Biomed. Anal. 19(5):695-707

(1999); Bynum et al., Hybridoma 18(5):407-411 (1999), Jakobovits et al., Proc. Natl. Acad. Sci. USA, 90:2551 (1993); Jakobovits et al., Nature, 362:255-258 (1993); Bruggemann et al., Year Immuno. 7:33 (1993); Barbas et al., Proc. Nat. Acad. Sci. USA 91:3809-3813 (1994); Schier et al., Gene 169:147-155 (1995); Yelton et al., J. Immunol. 155:1994-2004 (1995); Jackson et. Al., J. Immunol. 154(7): 3310-9 (1995); Hawkins et al., J. Mol. Biol. 226:889-896 (1992), U.S. Pat. Nos. 4,816,567, 5,514,548, 5,545,806, 5,569,825, 5,591,669, 5,545,807; PCT Patent Application Publication No. WO 97/17852, each of which is hereby incorporated by reference in its entirety).

Preferred antibodies of the invention can specifically bind to EGFR, preferably human EGFR. Although not limited, the antibody may be preferably selected from cetuximab, panitumumab, and zalutumumab, e.g., further comprising an isoprenylation sequence and/or spacer. In some embodiments, the antibody comprises cetuximab.

When the antibody comprises at least one light chain and at least one heavy chain, at least one light chain of the antibody, or at least one heavy chain of the antibody, or both may comprise an amino acid region having an amino acid motif capable of being recognized by an isoprenoid transferase. As an antibody may comprise four polypeptide chains (e.g., two heavy chains and two light chains), an antibody may comprise four isoprenylation sequences, each of which can be used to conjugate an active agent to the antibody via a linker. Thus, an antibody-drug conjugate may comprise 4 linkers, each conjugated to an active agent. Accordingly, an antibody-drug conjugate may comprise at least one linker and at least one active agent. An antibody-drug conjugate may comprise at least two linkers, and an antibody-drug conjugate may comprise at least two active agents. An antibody-drug conjugate may comprise 1, 2, 3, or 4 linkers. An antibody-drug conjugate may comprise 1, 2, 3, or 4 active agents.

The antibody-drug conjugates according to the present invention may comprise an isoprenylation sequence, such as CYYX, XXCC, XCXC, or CXX, preferably CYYX (wherein, C represents cysteine, Y represents an aliphatic amino acid, such as leucine, isoleucine, valine, and/or methionine, and X represents an amino acid that determines a substrate specificity of the isoprenoid transferase, such as glutamine, glutamate, serine, cysteine, methionine, alanine, and/or leucine).

The active agent may be a drug, toxin, affinity ligand, detection probe, or combination of any of the foregoing.

The active agent may be selected from erlotinib; bortezomib; fulvestrant; sutent; letrozole; imatinib mesylate; PTK787/ZK 222584; oxaliplatin; 5-fluorouracil; leucovorin; rapamycin (Sirolimus); lapatinib; lonafarnib; sorafenib; gefitinib; AG1478; AG1571; alkylating agents (for example, thiotepa or cyclophosphamide); alkyl sulfonate (for example, busulfan, improsulfan, or piposulfan); aziridine (for example, benzodopa, carboquone, meturedopa, or uredopa); ethyleneimine, methylmelamine, altretamine, triethylenemelamine, triethylenephosphoramide, triethylenethiophosphoramide, trimethylolmelamine; acetogenins (for example, bullatacin or bullatacinone); camptothecin; topotecan; bryostatin; callystatin; CC-1065 (including its adozelesin, carzelesin, or bizelesin synthetic analogs); cryptophycins (for example, cryptophycin 1 or cryptophycin 8); dolastatin; duocarmycin (including synthetic analogs, e.g., KW-2189 and CB1-TM1); eleutherobin; pancratistatin; sarcodictyin; spongistatin; nitrogen mustard (for example, chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, or uracil mustard); nitrousurea (for example, carmustine, chlorozotocin, fotemustine, lomustine, nimustine, or ranimnustine); antibiotics (for example, enediyne antibiotics such as calicheamycin selected from calicheamycin gamma 11 and calicheamycin omega 11, or dynemicin including dynemicin A); bisphosphonate (for example, clodronate; esperamicin, neocarzinostatin chromophore, or related chromoprotein enediyne antibiotic chromophores, aclacinomysins, actinomycin, anthramycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin (for example, morpholino-doxorubicin, cyanomorpholino-doxorubicin, 2-pyrrolino-doxorubicin, liposomal doxorubicin, or deoxydoxorubicin), epirubicin, esorubicin, marcellomycin, mitomycins (for example, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, or zorubicin); anti-metabolites (for example, 5-fluorouracil); folic acid analogs (for example, denopterin, methotrexate, pteropterin, or trimetrexate); purine analogs (for example, fludarabine, 6-mercaptopurine, thiamiprine, or thiguanine); pyrimidine analogs (for example, ancitabine, azacitidine, 6-azauridine, carmofur, cytarabine, dideoxyuridine, doxifluridine, enocitabine, or floxuridine); androgens (for example, calusterone, dromostanolone propionate, epitiostanol, mepitiostane), or testolactone); anti-adrenals (for example, aminoglutethimide, mitotane, or trilostane); folic acid replenisher (for example, folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoids (for example, maytansine or ansamitocins); trichothecenes (particularly T-2 toxin, verracurin A, roridin A, or anguidine); mitoguazone; mitoxantrone; mopidanmol; nitraerine; pentostatin; phenamet; pirarubicin; losoxantrone; 2-ethylhydrazide; procarbazine; polysaccharide K complex; razoxane; rhizoxin; sizofiran; spirogermanium; tenuazonic acid; triaziquone; 2,2',2"-trichlorotriethylamine; trichothecenes (particularly, T-2 toxin, verracurin A, roridin A, and anguidine); urethane; vindesine; dacarbazine; mannomustine; mitobronitol; mitolactol; pipobroman; gacytosine; arabinoside; cyclophosphamide; thiotepa; rimeth (for example, paclitaxel), ABRAXANE™ cremophor-free, albumin-engineered nanoparticle formulation of paclitaxel, doxetaxel; chlorambucil; gemcitabine; 6-thioguanine; mercaptopurine; platinum analog (for example, cisplatin or carboplatin); vinblastine; platinum; etoposide, ifosfamide; mitoxantrone; vincristine; vinorelbine; novantrone; teniposide; edatrexate; daunomycin; aminopterin; xeloda; ibandronate; CPT-11; topoisomerase inhibitor (RFS 2000); difluoromethylornithine; retinoid (for example, retinoic acid); capecitabine, and pharmaceutically acceptable salts, solvates, acids, or derivatives thereof, but is not necessarily limited thereto.

The active agent may be selected from (i) anti-hormonal agents that act to regulate or inhibit hormone action on tumors such as anti-estrogens and selective estrogen receptor modulators, including, for example, tamoxifen, raloxifene, droloxifene, 4-hydroxytamoxifen, trioxifene, keoxifene, LY117018, onapristone, and toremifene; (ii) aromatase inhibitors that inhibit aromatase enzyme, which regulates estrogen production in the adrenal glands, for example, 4(5)-imidazoles, aminoglutethimide, megestrol acetate, exemestane, letrozole, and anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those that inhibit expression of genes in signaling pathways implicated in adherent cells, for example, PKC-alpha, Raf, H-Ras; (viii) ribozyme, for example, VEGF inhibitor such as ribozyme and HER2 expression inhibitors; (ix) vaccines such as a gene therapy vaccine; ALLOVECTIN® vaccine, LEUVECTIN vaccine, VAXID vaccine; PROLEUKIN®rIL-2; LURTOTECAN® topoisomerase 1 inhibitor; ABARELIX® rmRH; (x) an anti-angiogenic agent such as Bevacizumab; and (xi) pharmaceutically acceptable salts, solvates, acids, or derivatives thereof.

In addition, cytokines may be used as the active agent. Cytokines are small cell-signaling protein molecules that are secreted by numerous cells and are a category of signaling molecules used extensively in intercellular communication. The cytokines include monokines, lymphokines, traditional polypeptide hormones, and the like. Examples of the cytokines include growth hormone (for example, human growth hormone, N-methionyl human growth hormone, or bovine growth hormone); parathyroid hormone; thyroxine; insulin; proinsulin; relaxin; prorelaxin; glycoprotein hormone (for example, follicle stimulating hormone (FSH), thyroid stimulating hormone (TSH), or luteinizing hormone (LH)); hepatic growth factor; fibroblast growth factor; prolactin; placental lactogen; tumor necrosis factor-α, tumor necrosis factor-β; mullerian-inhibiting substance; mouse gonadotropin-associated peptide; inhibin; activin; vascular endothelial growth factor; integrin, thrombopoietin (TPO); nerve growth factor (for example, NGF-β); platelet-growth factor; transforming growth factor (TGF) (for example, TGF-α or TGF-β); insulin-like growth factor-I, insulin-like growth factor-II; erythropoietin (EPO); osteoinductive factor; interferon (for example, interferon-α, interferon-β, or interferon-γ); colony stimulating factor (CSF) (for example, macrophage-CSF (M-CSF), granulocyte-macrophage-CSF (GM-CSF), or granulocyte-CSF (G-CSF)); interleukin (IL) (for example, IL-1, IL-1α, IL-2, IL-3, IL-4, IL-5, IL-6, IL-7, IL-8, IL-9, IL-10, IL-11, or IL-12); tumor necrosis factor (TNF) (for example, TNF-α or TNF-β); and polypeptide factor (for example, LIF or kit ligand), but are not limited thereto. Further, the term "cytokine" also includes cytokines from natural sources or recombinant cell cultures and biologically active equivalents of the native sequence cytokines.

The term "toxin" refers substances that are poisonous to living cells or organisms. Toxins may be small molecules, peptides or proteins capable of causing cell dysfunction or cell death after contact with or absorption by body tissue, e.g., through an interaction with one or more biological macromolecules such as enzymes or cell receptors. Toxins include plant toxins and animal toxins. Examples of animal toxins include diphtheria toxin, botulinum toxin, tetanus toxin, dysentery toxin, cholera toxin, tetrodotoxin, brevetoxin, and ciguatoxin, but are not limited thereto. Examples of plant toxins include ricin and AM-toxin, but are not limited thereto.

Examples of small molecule toxins include auristatin, tubulysin, geldanamycin (Kerr et al., 1997, Bioconjugate Chem. 8(6):781-784), maytansinoid (EP 1391213, ACR 2008, 41, 98-107), calicheamicin (U.S. Patent Publication No. 2009/0105461, Cancer Res. 1993, 53, 3336-3342), daunomycin, doxorubicin, methotrexate, vindesine, SG2285 (Cancer Res. 2010, 70(17), 6849-6858), dolastatin, dolastatin analogs auristatin (U.S. Pat. No. 5,635,483), cryptophycin, camptothecin, rhizoxin derivative, CC-1065 analog or derivative, duocarmycin, enediyne antibiotic, esperamicin, epothilone, pyrrolobenzodiazepine (PBD) derivatives, α-amanitin, and toxoid, but are not limited thereto. Toxins may exhibit cytotoxicity and cell growth-inhibiting activity by tubulin binding, DNA binding, topoisomerase suppression, and the like.

The term "ligand" refers to a molecule capable of forming a complex with a target biomolecule. An example of the ligand is a molecule bound to a predetermined position of a target protein to transmit a signal. The ligand may be a substrate, an inhibitor, a stimulating agent, a neurotransmitter, or a radioisotope.

"Detectable moiety" or a "label" refers to a composition detectable by spectroscopic, photochemical, biochemical, immunochemical, radioactive, or chemical means. For example, useful labels include $^{32}P$, $^{35}S$, fluorescent dyes, electron-dense reagents, enzymes (for example, enzymes commonly used in an ELISA), biotin-streptavidin, dioxigenin, haptens, and proteins for which antisera or monoclonal antibodies are available, or nucleic acid molecules with a sequence complementary to a target. The detectable moiety often generates a measurable signal, such as a radioactive, chromogenic, or fluorescent signal, that may be used to quantify the amount of bound detectable moiety in a sample. Quantitation of the signal may be achieved, for example, by scintillation counting, densitometry, flow cytometry, ELISA, or direct analysis by mass spectrometry of intact or subsequently digested peptides (one or more peptide may be assessed).

The term "probe" as used herein refers to a material that may (i) provide a detectable signal, (ii) interact a first probe or a second probe to modify a detectable signal provided by the first or second probe, such as fluorescence resonance energy transfer (FRET), (iii) stabilize an interaction with an antigen or a ligand or increase binding affinity; (iv) affect electrophoresis mobility or cell-intruding activity by a physical parameter such as charge, hydrophobicity, etc., or (v) control ligand affinity, antigen-antibody binding, or ionic complex formation.

The active agent may be an immunomodulatory compound, an anticancer agent, an antiviral agent, an antibacterial agent, an antifungal agent, an antiparasitic agent, or a combination thereof.

An immunomodulatory compound may be selected from aminocaproic acid, azathioprine, bromocriptine, chlorambucil, chloroquine, cyclophosphamide, cyclosporine, cyclosporine A, danazol, dehydroepiandrosterone, dexamethasone, etanercept, hydrocortisone, hydroxychloroquine, infliximab, meloxicam, methotrexate, mycophenylate mofetil, prednisone, sirolimus, and tacrolimus. An anticancer agent may be selected from 1-methyl-4-phenylpyridinium ion, 5-ethynyl-1-beta-D-ribofuranosylimidazole-4-carboxamide (EICAR), 5-fluorouracil, 9-aminocamptothecin, actinomycin D, asparaginase, bicalutamide, bis-chloroethylnitrosourea (BCNU), bleomycin, bleomycin A2, bleomycin B2, busulfan, camptothecin, carboplatin, carmustine, CB1093, chlorambucil, cisplatin, crisnatol, cyclophosphamide, cytarabine, cytosine arabinoside, rimeth, dacarbazine, dactinomycin, daunorubicin, decarbazine, deferoxamine, demethoxy-hypocrellin A, docetaxel, doxifluridine, doxorubicin, EB 1089, epirubicin, etoposide, floxuridine, fludarabine, flutamide, gemcitabine, goserelin, hydroxyurea, idarubicin, ifosfamide, interferon-α, interferon-γ, irinotecan, KH1060, leuprolide acetate, lomustine, lovastatin, megestrol, melphalan, mercaptopurine, methotrexate, mitomycin, mitomycin C, mitoxantrone, mycophenolic acid, nitrogen mustard, nitrosourea, paclitaxel, peplomycin, photosensitizer Pe4, phthalocyanine, pirarubicin, plicamycin, procarbazine, raloxifene, raltitrexed, revlimid, ribavirin, staurosporine, tamoxifen, teniposide, thalomid, thapsigargin, thioguanine, tiazofurin, topotecan, treosulfan, trimetrexate, tumor necrosis factor, velcade, verapamil, verteporfin, vinblastine, vincristine, vinorelbine, and zorubicin. An antiviral agent may be selected from pencicyclovir, valacyclovir, gancicyclovir, foscarnet, ribavirin, idoxuridine, vidarabine, trifluridine, acyclovir, famcicyclovir, amantadine, rimantadine, cidofovir, antisense oligonucleotide, immunoglobulin, and interferon. An antibacterial agent may be selected from chloramphenicol, vancomycin, metronidazole, rimethoprim, sulfamethazole, quinupristin, dalfopristin, rifampin, spectinomycin, and nitrofurantoin. The antifungal agent may be selected from amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, balsam of peru, ciclopirox olamine, piroctone olamine, zinc pyrithione, and selenium sulfide. An antiparasitic agent may be selected from mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole, and miltefosine.

The antibody may comprise an amino acid motif selected from Ab-HC-(G)$_z$CVIM, Ab-HC-(G)$_z$CVLL, Ab-LC-(G)$_z$CVIM, and Ab-LC-(G)$_z$CVLL, wherein Ab represents an antibody, -HC- represents a heavy chain, -LC- represents a light chain, G represents a glycine, C represents cysteine, V represents valine, I represents isoleucine, M represents methionine, L represents leucine, and z is an integer from 0 to 20.

An antibody-drug conjugate may have the structure of Formula (V) or (VI).

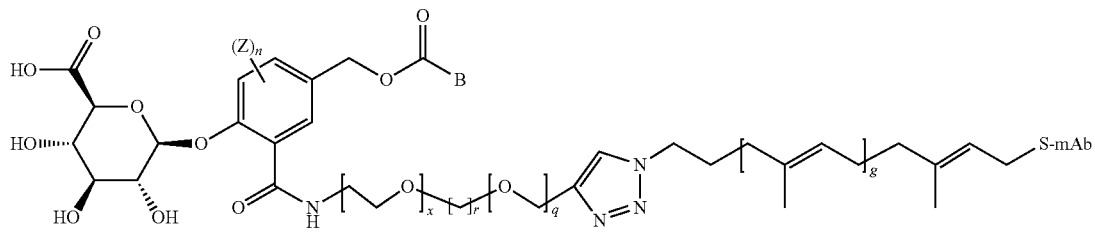

(V)

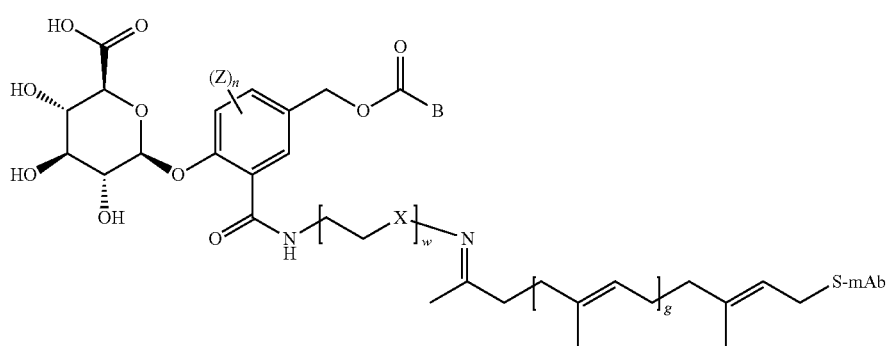

(VI)

Z is hydrogen, (C$_1$-C$_8$)alkyl, halogen, cyano, or nitro, preferably hydrogen;

X is —O—, (C$_1$-C$_8$)alkylene, or —NR$_{21}$—, preferably —O—;

R$_{21}$ is hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl;

n is an integer of 1 to 3, preferably 3, and when n is an integer of 2 or more, each of the Z(s) are the same as or different from each other, preferably the same;

r is an integer of 1 to 10, preferably 3;

q is an integer of 1 to 10, preferably 1;

w is an integer of 1 to 10, preferably 3.

X is an integer of 0 to 10, preferably 0;

g is an integer of 1 to 10, preferably 1;

—S-mAb is the antibody; and

B is the active agent.

B may be selected from any one of the following structures:

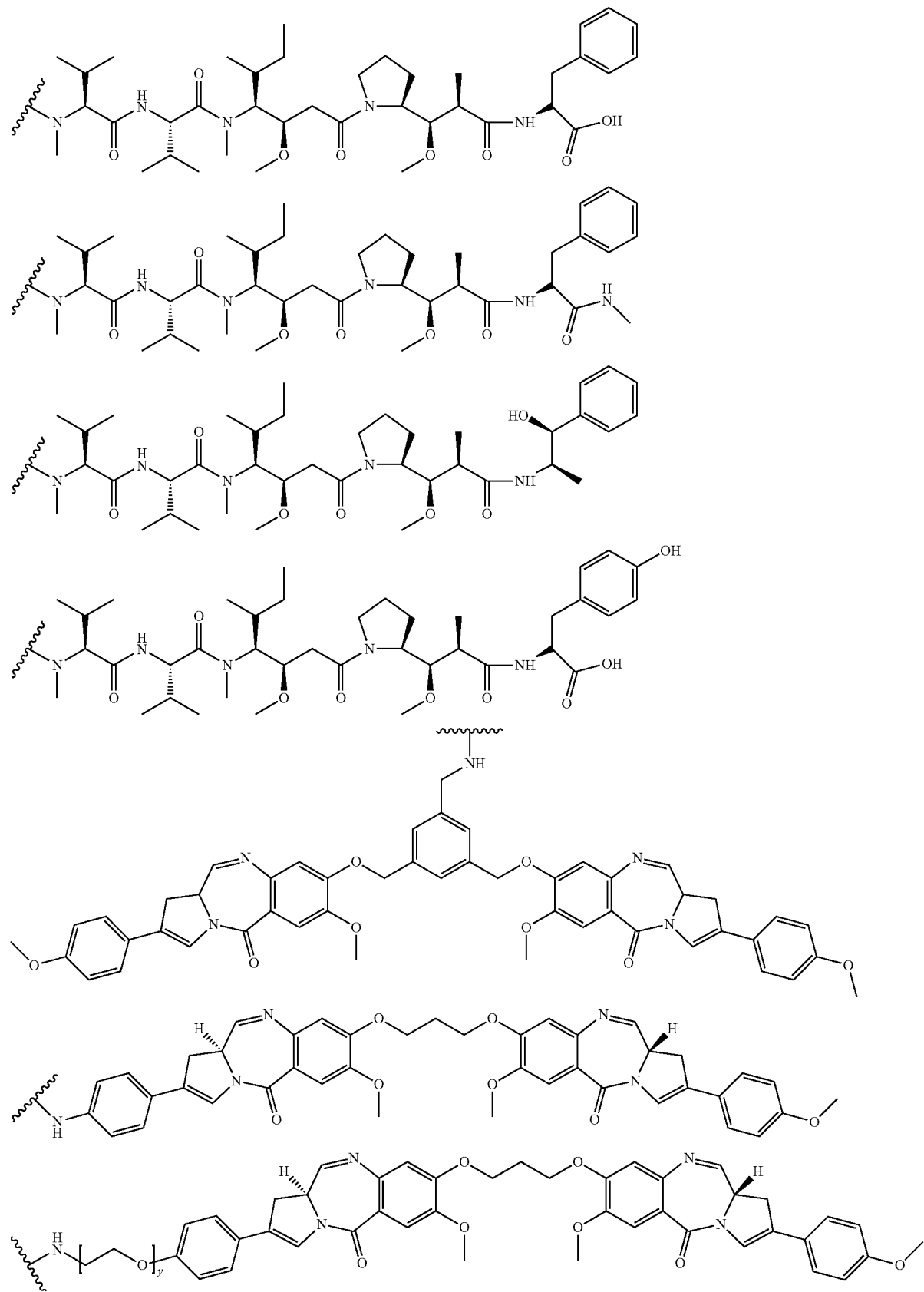

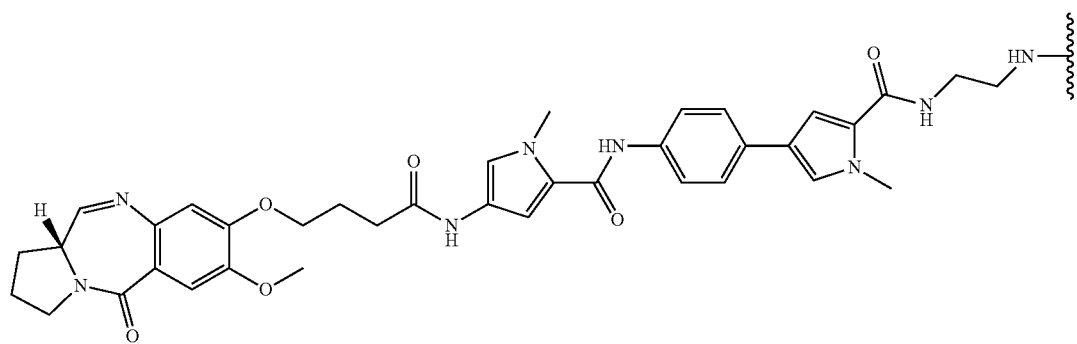
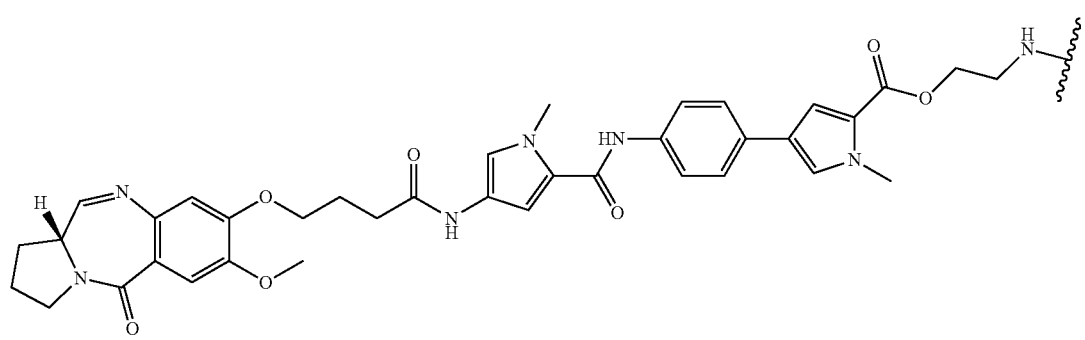
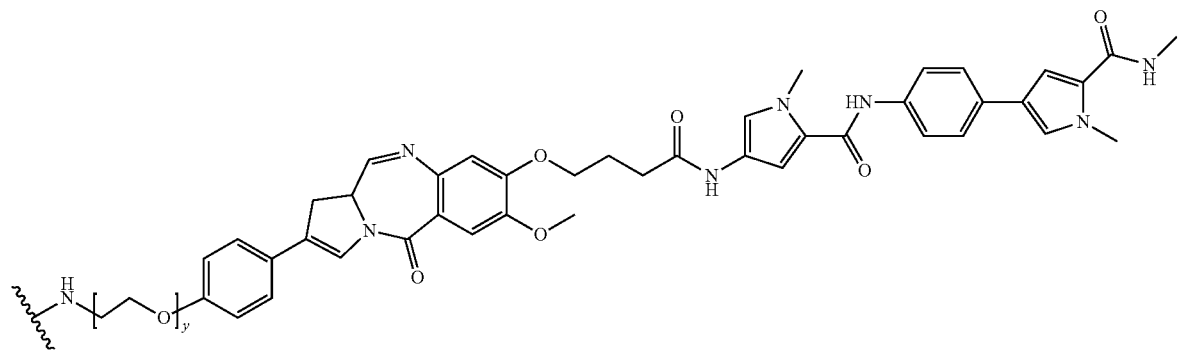
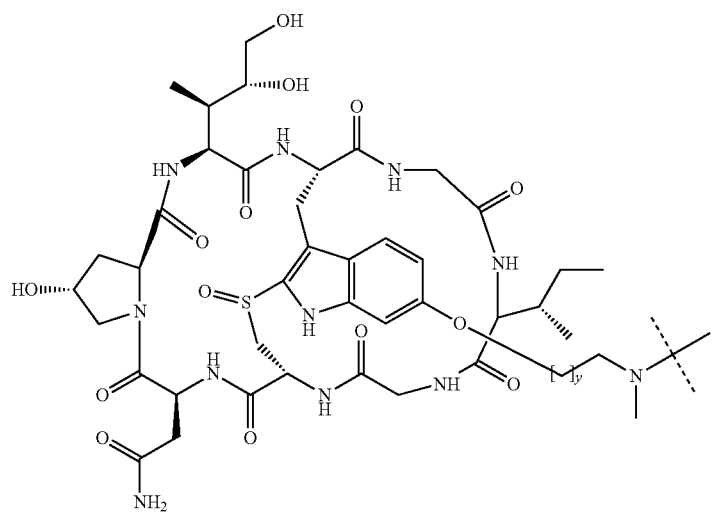

-continued

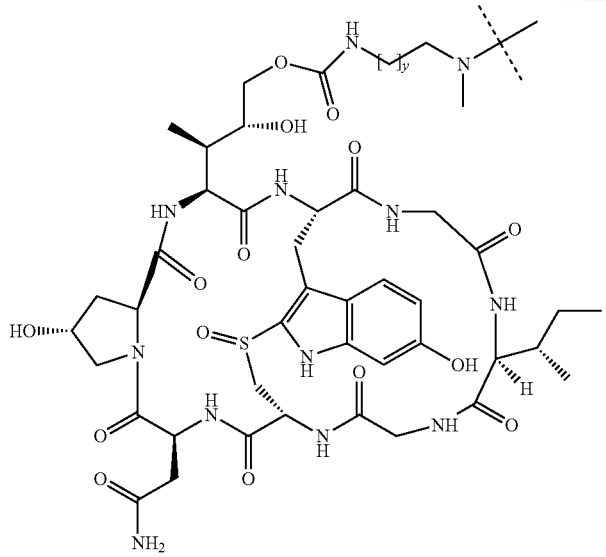

wherein y is an integer of 1 to 10.

The antibody-drug conjugate may be used to transfer the active agent to a target cell of a subject to treat the subject using a method of preparing a composition known to those skilled in the art. In some aspects, the invention relates to a composition (e.g., a pharmaceutical composition) comprising an antibody-drug conjugate as described herein.

Compositions may be prepared in an injectable form, either as a liquid solution or as a suspension. Solid forms suitable for injection may also be prepared, e.g., as emulsions, or with the antibody-drug conjugate encapsulated in liposomes. Antibody-drug conjugates may be combined with a pharmaceutically acceptable carrier, which includes any carrier that does not induce the production of antibodies harmful to the subject receiving the carrier. Suitable carriers typically comprise large macromolecules that are slowly metabolized, for example, proteins, polysaccharides, polylactic acids, polyglycolic acids, polymeric amino acids, amino acid copolymers, lipid aggregates, and the like.

The compositions may also contain diluents, for example, water, saline, glycerol, and ethanol. Auxiliary substances, for example, wetting or emulsifying agents, pH buffering substances, and the like may also be present therein. The compositions may be parenterally administered by injection, wherein such injection may be either subcutaneous or intramuscular injection. In some embodiments, a composition may be administered into a tumor. The composition may be inserted (e.g., injected) into a tumor. Additional formulations are suitable for other forms of administration, such as suppository or oral administration. Oral compositions may be administered as a solution, suspension, tablet, pill, capsule, or sustained release formulation.

The compositions may be administered in a manner compatible with a dose and a formulation. The composition preferably comprises a therapeutically effective amount of the antibody-drug conjugate. The term "therapeutically effective amount" means a single dose or a composition administered in a multiple dose schedule that is effective for the treatment or prevention of a disease or disorder. A dose may vary, depending on the subject to be treated, the subject's health and physical conditions, a degree of protection to be desired, and other relevant factors. The exact amount of an active ingredient (e.g., the antibody-drug conjugate) may depend on the judgment of a doctor. For example, a therapeutically effective amount of the antibody-drug conjugate or composition containing the same may be administered to a patient suffering from a cancer or tumor to treat the cancer or tumor.

The antibody-drug conjugate according to the present invention or the composition containing the same may be administered in the form of a pharmaceutically acceptable salt or solvate thereof. In some embodiments, the antibody-drug conjugate according to the present invention or the composition containing the same may be administered with a pharmaceutically acceptable carrier, a pharmaceutically acceptable excipient, and/or a pharmaceutically acceptable additive. The effective amount and the type of the pharmaceutically acceptable salt or solvate, excipient and additive may be measured using standard methods (see, e.g., Remington's Pharmaceutical Sciences, Mack Publishing Co., Easton, Pa., 18$^{th}$ Edition, 1990).

The term "therapeutically effective amount" with regard to cancer or tumor means an amount that may decrease the number of cancer cells; decrease a size of cancer cells; inhibit cancer cells from intruding into peripheral systems or decrease the intrusion; inhibit cancer cells from spreading to other systems or decrease the spreading; inhibit cancer cells from growing; and/or ameliorate at least one symptom related to the cancer. In the treatment of cancer, the effectiveness of a drug may be assessed by time to tumor progression (TTP) and/or response rate (RR).

The term "pharmaceutically acceptable salts" used herein includes organic salts and inorganic salts. Examples thereof include hydrochloride, hydrobromide, hydroiodide, sulfate, citrate, acetate, oxalate, chloride, bromide, iodide, nitrate, bisulfate, phosphate, acidic phosphate, isonicotinate, lactate, salicylate, acidic citrate, tartrate, oleate, tannate, pantonate, bitartrate, ascorbate, succinate, maleate, gentisinate, fumarate, gluconate, glucoronate, saccharate, formate, benzoate, glutamate, methane sulfonate, ethane sulfonate, benzene sulfonate, p-toluene sulfonate, and pamoate (that is, 1,1'-methylenebis-(2-hydroxy-3-naphthoate)). The pharmaceutically acceptable salt may include another molecule (for example, acetate ions, succinate ions, and/or other counter ions).

Exemplary solvates that may be used for pharmaceutically acceptable solvates of the antibody-drug conjugates described herein include water, isopropanol, ethanol, methanol, dimethyl sulfoxide, ethyl acetate, acetic acid, and ethanol amine.

In some embodiments, the invention relates to a method of treating cancer in a subject, comprising administering a pharmaceutical composition comprising an antibody-drug conjugate as described herein to the subject. The cancer is preferentially a cancer that is associated with EGFR, i.e., wherein at least some of the cancer cells express EGFR. The cancer may be adenocarcinoma, breast cancer, bronchioloalveolar carcinoma, colorectal cancer, epithelial cancer, lung cancer, pancreatic cancer, prostate cancer, squamous cell cancer, or head and neck cancer. The cancer may be a metastatic cancer. For example, the cancer may be metastatic colorectal cancer, metastatic non-small cell lung cancer, or head and neck cancer. In preferred embodiments, the subject is a mammal. For example, the subject may be selected from rodents, lagomorphs, felines, canines, porcines, ovines, bovines, equines, and primates. In certain preferred embodiments, the subject is a human.

Hereinafter, configurations of the present invention will be described in detail through Examples, but the following Examples are only to assist in understanding of the present invention. The scope of the present invention is not limited thereto.

EXEMPLIFICATION

Example 1. Preparation of Compound 1k

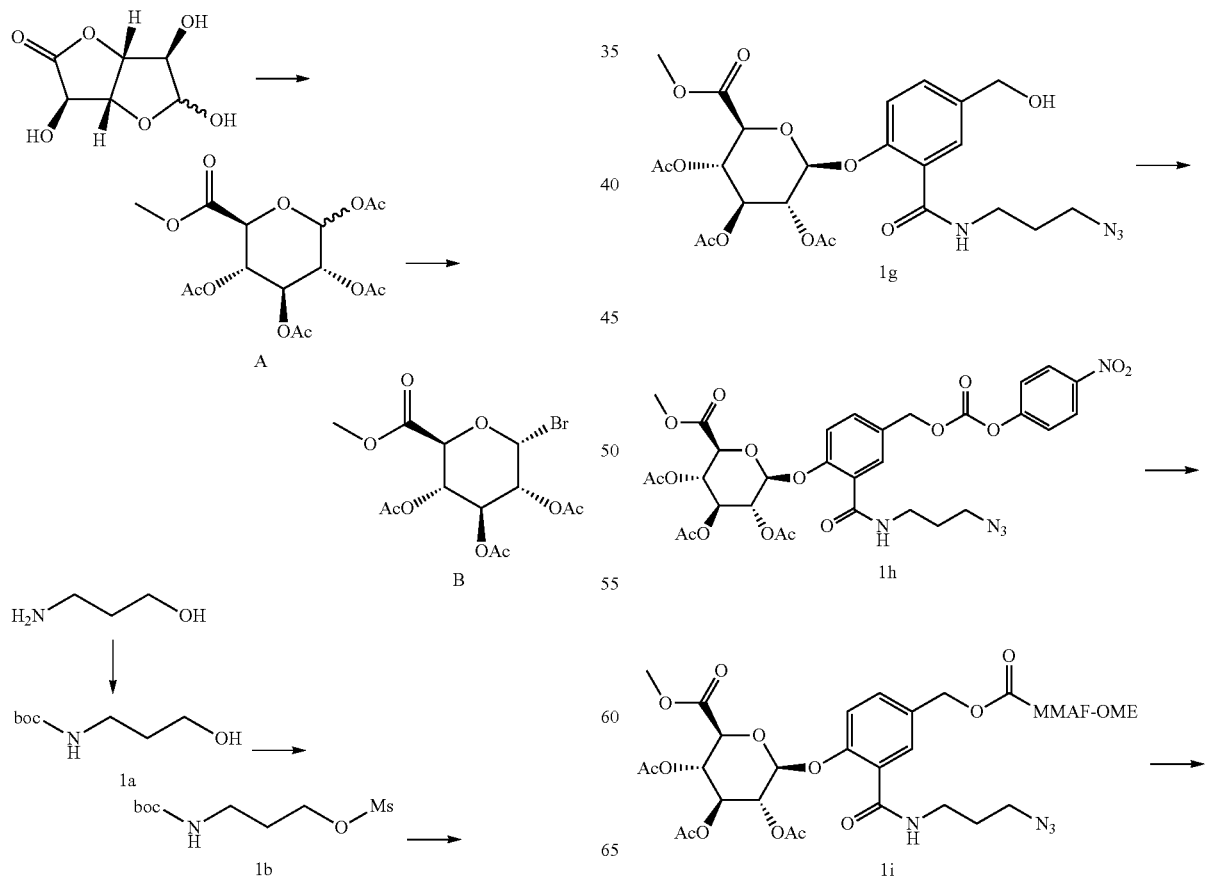

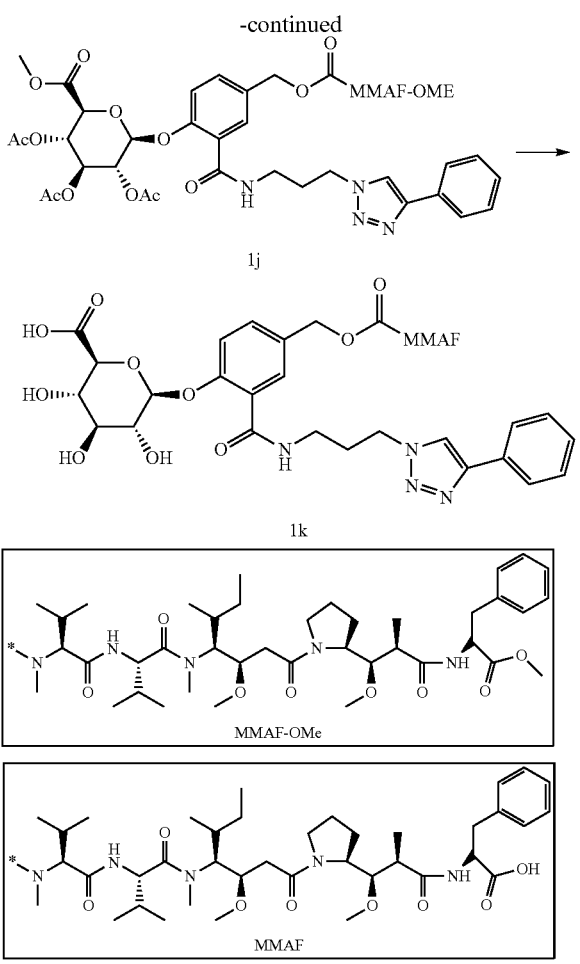

Preparation of Compound A

D-glucurono-6,3-lactone (19 g, 107.88 mmol) was dissolved in methanol (250 mL) at room temperature under nitrogen atmosphere, a solution of NaOH (100 mg) in methanol (100 mL) was slowly added thereto and stirred for 2 hours, and then, a solution of NaOH (200 mL) in methanol (15 mL) was added to the mixture and stirred for 3 hours. After the reaction was completed, the methanol solvent of the mixture was removed under reduced pressure, and pyridine (50 mL) and acetic anhydride (54 mL) were added thereto at 10° C. or less and stirred at room temperature for 4 hours. After the reaction was completed, the resultant product was concentrated under reduced pressure. The residue was subjected to column chromatography, thereby obtaining Compound A (20 g, 50%).

$^1$H NMR (600 MHz, CDCl$_3$) δ 5.77 (d, J=7.8 Hz, 1H), 5.31 (t, J=9.6 Hz, 1H), 5.24 (t, J=9.6 Hz, 1H), 5.14 (m, 1H), 4.17 (d, J=9 Hz, 1H), 3.74 (s, 3H), 2.12 (s, 3H), 2.04 (m, 9H)

Preparation of Compound B

Compound A (5 g, 13.28 mmol) was dissolved in 33% HBr in AcOH (20 mL) at 0° C. under nitrogen atmosphere and then, stirred at room temperature for 2 hours. After the reaction was completed, toluene (50 mL) was added thereto, and the mixture was concentrated under reduced pressure. Thereafter, ethylacetate (100 mL) and NaHCO$_3$ solution (100 mL) were added thereto to extract an organic layer, and the obtained organic layer was dried over anhydrous sodium sulfate, followed by concentration under reduced pressure. The residue was subjected to column chromatography, thereby obtaining Compound B (5.27 g, 100%).

$^1$H NMR (600 MHz, CDCl$_3$) δ 6.64 (d, J=3.6 Hz, 1H), 5.61 (t, J=3.6 Hz, 1H), 5.24 (t, J=3.6 Hz, 1H), 4.85 (m, 1H), 4.58 (d, d, J=10.2 Hz, 1H), 3.76 (s, 3H), 2.10 (s, 3H), 2.06 (s, 3H), 2.05 (s, 3H)

Preparation of Compound 1a (See U.S. Pat. No. 6,414,148, Hereby Incorporated by Reference)

3-amino-1-propanol (3.0 g, 66.569 mmol) was dissolved in dichloromethane (150 mL) at 0° C. under nitrogen atmosphere, and di-tert-butyldicarbonate (16 g, 73.226 mmol) was added thereto. The obtained mixture was stirred at room temperature for 12 hours. After the reaction was completed, the solvent was concentrated under reduced pressure. The residue was subjected to column chromatography, thereby obtaining Compound 1a (6.4 g, 92%).

$^1$H NMR (400 MHz, CDCl$_3$) δ 4.78 (s, 1H), 3.65 (m, 2H), 3.30 (m, 2H), 2.90 (s, 1H), 1.68 (m, 2H), 1.48 (s, 9H); EI-MS m/z: 176 (M+)

Preparation of Compound 1b (See U.S. Pat. No. 7,816,344, Hereby Incorporated by Reference)

Compound 1a (6.04 g, 34.469 mmol) and triethylamine (TEA, 14.4 mL, 103.407 mmol) were dissolved in tetrahydrofuran at 0° C. under nitrogen atmosphere and then, slowly treated with methanesulfonic anhydride (7.21 g, 41.363 mmol). The obtained mixture was stirred at room temperature under nitrogen atmosphere for 12 hours. After the reaction was completed, the solvent was concentrated under reduced pressure. The residue was subjected to column chromatography, thereby obtaining Compound 1b (9.01 g, 98%).

$^1$H NMR (400 MHz, CDCl$_3$) δ 4.73 (s, 1H), 4.30 (t, J=5.9 Hz, 2H), 3.31-3.24 (m, 2H), 3.04 (s, 3H), 1.94 (t, J=6.1 Hz, 2H), 1.44 (s, 9H). EI-MS m/z: 254 (M+)

Preparation of Compound 1c (See PCT Patent Application Publication No. WO 2013/166319, Hereby Incorporated by Reference)

Compound 1b (3.0 g, 11.842 mol) was dissolved in dimethylformamide (40 mL) at room temperature under nitrogen atmosphere, and then treated with sodium azide (924 mg, 14.211 mmol), and the obtained mixture was stirred at 60° C. for 12 hours. After the reaction was completed, ethylacetate (50 mL), distilled water (50 mL), and 1N HCl (5 mL) were added thereto. The organic layer obtained as described above was dried over anhydrous sodium sulfate and concentrated under reduced pressure. The residue was subjected to column chromatography, thereby obtaining Compound 1c (2.3 g, 99%).

$^1$H NMR (600 MHz, CDCl$_3$) δ 4.63 (s, 1H), 3.36 (t, J=6.6 Hz, 2H), 3.24-3.18 (m, 2H), 1.80-1.75 (m, 2H), 1.45 (s, 9H). EI-MS m/z: 201 (M+)

Preparation of Compound 1d

Compound 1c (3.8 g, 18.977 mmol) was dissolved in dichloromethane (10 mL) at 0° C. under nitrogen atmosphere, and then 4M-HCl in dioxane (10 mL) was slowly added thereto. The obtained mixture was stirred for 12 hours. After the reaction was completed, the resultant was concentrated under reduced pressure, thereby obtaining Compound 1d (2.5 g, 99%).

$^1$H NMR (600 MHz, DMSO-d$_6$) δ 8.06 (s, 3H), 3.47 (t, J=6.6 Hz, 2H), 2.82 (t, J=7.2 Hz, 2H), 1.84-1.79 (m, 2H). EI-MS m/z: 101 (M+)

Preparation of Compound 1e

Compound 1d (58 mg, 0.420 mmol) and 5-formylsalicylic acid (100 mg, 0.601 mmol) were dissolved in dimethylformamide (DMF, 2 mL) at 0° C. under nitrogen atmosphere, and then diisopropylethylamine (DIPEA, 0.2 mL, 1.202 mmol) and PyBop (375 mg, 0.721 mmol) were added to the mixed solution. The obtained mixture was stirred at room temperature for 3 hours. After the reaction was completed, ethylacetate (30 mL) and distilled water (10 mL) were added thereto. The organic layer obtained as described above was dried over anhydrous sodium sulfate and concentrated under reduced pressure. The residue was subjected to column chromatography, thereby obtaining Compound 1e (82 mg, 79%).

$^1$H NMR (400 MHz, CDCl$_3$) δ 13.39 (s, 1H), 9.87 (s, 1H), 8.29 (s, 1H), 7.89 (dd, J=1.6, 7.2 Hz. 1H), 7.60 (s, 1H), 7.10 (d, J=8.8 Hz), 3.63-3.57 (m, 2H), 3.48 (t, J=6.4 Hz, 2H), 1.99-1.92 (m, 2H). EI-MS m/z: 249 (M+)

Preparation of Compound 1f

Compound 1e (78 mg, 0.314 mmol) and Compound B (125 mg, 0.314 mmol) were dissolved in acetonitrile (3 mL) at room temperature under nitrogen atmosphere, and then silver oxide (291 mg, 1.256 mmol) and a molecular sieve (125 mg) were added thereto. The obtained mixture was stirred at room temperature for 3 hours. After the reaction was completed, the mixture was celite-filtered, and the filtrate was concentrated under reduced pressure. The residue was subjected to column chromatography, thereby obtaining Compound 1f (160 mg, 90%).

$^1$H NMR (400 MHz, CDCl$_3$) δ 10.00 (s, 1H), 8.66 (d, J=2.4 Hz, 1H), 8.02 (dd, J=2.0, 6.4 Hz, 1H), 7.46 (t, J=6.4 Hz, 1H), 7.14 (d, J=8.4 Hz, 1H), 5.48-5.33 (m, 4H), 4.28 (d, J=8.8 Hz, 1H), 3.74 (s, 3H), 3.73-3.64 (m, 1H), 3.50-3.42 (m, 3H), 2.09-2.07 (m, 9H), 2.00-1.92 (m, 2H).

EI-MS m/z: 565 (M+)

Preparation of Compound 1g

Compound 1f (160 mg, 1.510 mmol) was dissolved in 2-propanol (0.4 mL) and chloroform (2 mL) at 0° C. under nitrogen atmosphere, and then silica gel (2 g) and sodium borohydride (27 mg, 0.708 mmol) were added thereto. After the obtained mixture was stirred at 0° C. for 2 hours, the reactant was celite-filtered, and the filtrate was concentrated under reduced pressure. The residue was subjected to column chromatography, thereby obtaining Compound 1g (115 mg, 71%).

$^1$H NMR (600 MHz, CDCl$_3$) δ 8.06 (d, J=2.4 Hz, 1H), 7.50-7.44 (m, 2H), 7.01 (d, J=90 Hz, 1H), 5.45-5.31 (m, 4H), 4.38 (s, 2H), 4.22 (d, J=9.0 Hz, 1H), 3.74 (s, 3H), 3.67-3.61 (m, 1H), 3.46-3.41 (m, 3H), 2.07-2.04 (m, 9H), 1.97-1.91 (m, 2H). EI-MS m/z: 567 (M+)

Preparation of Compound 1h

Compound 1g (100 mg, 0.177 mmol) was dissolved in DMF (1 mL) at 0° C. under nitrogen atmosphere, and then bis(4-nitrophenyl)carbonate (110 mg, 0.353 mmol) and DIPEA (50 uL, 0.265 mmol) were added thereto. The obtained mixture was stirred at room temperature for 2 hours. After the reaction was completed, ethylacetate (30 mL) and distilled water (10 mL) were added thereto. The organic layer obtained as described above was dried over anhydrous sodium sulfate and concentrated under reduced pressure. The residue was subjected to column chromatography, thereby obtaining Compound 1h (75 mg, 58%).

$^1$H NMR (600 MHz, CDCl$_3$) δ 8.29-8.27 (m, 2H), 8.23 (d, J=2.4 Hz, 1H), 7.54 (dd, J=2.4, 6.6 Hz, 1H), 7.49 (t, J=6.4 Hz, 1H), 7.39-7.37 (m, 2H), 7.04 (d, J=8.4 Hz, 1H), 5.45-5.29 (m, 4H), 5.28 (s, 2H), 4.23 (d, J=9.0 Hz, 1H), 3.75 (s, 3H), 3.68-3.64 (m, 1H), 3.46-3.42 (m, 3H), 2.08-2.05 (m, 9H), 1.98-1.93 (m, 2H). EI-MS m/z: 732 (M+)

Preparation of Compound 1i

Compound 1h (50 mg, 0.068 mmol) was dissolved in DMF (0.8 mL) at room temperature under nitrogen atmosphere, and then MMAF-Ome (51 mg, 0.068 mmol) was added thereto. The resultant product was treated with 1-hydroxybenzotriazole anhydrous (HOBT, 2 mg, 0.013 mmol), pyridine (0.24 mL), and DIPEA (12 uL, 0.068 mmol). The obtained mixture was stirred at room temperature for 18 hours. After the reaction was completed, ethylacetate (20 mL) and distilled water (10 mL) were added thereto. The organic layer obtained as described above was dried over anhydrous sodium sulfate and concentrated under reduced pressure. The residue was subjected to column chromatography, thereby obtaining Compound 1i (71 mg, 78%).

EI-MS m/z: 1339 (M+)

Preparation of Compound 1j

Compound 1i (30 mg, 0.022 mmol) and phenylacetylene (3.7 uL, 0.033 mmol) were dissolved in ethanol (0.2 mL) and water (30 ul) at room temperature under nitrogen atmosphere, and then 0.1M CuSO$_4$ aqueous solution (30 ul) and 1.0M sodium ascorbate aqueous solution (30 ul) were added thereto. The resultant product was treated with HOBT (2 mg, 0.013 mmol), pyridine (0.24 mL), and DIPEA (12 uL, 0.068 mmol). The obtained mixture was stirred at room temperature for 5 hours. After the reaction was completed, ethylacetate (20 mL) and distilled water (5 mL) were added thereto. The organic layer obtained as described above was dried over anhydrous sodium sulfate and concentrated under reduced pressure. The residue was subjected to column chromatography, thereby obtaining Compound 1j (26 mg, 81%).

EI-MS m/z: 1441 (M+)

Preparation of Compound 1k

Compound 1j (20 mg, 0.013 mmol) was dissolved in methanol (0.2 mL) at 0° C. under nitrogen atmosphere, and then LiOH.H$_2$O (6 mg, 0.138 mmol) in water (0.2 mL) was added thereto. The resultant mixture was stirred at room temperature for 1 hour. After the reaction was completed, chloroform (10 mL), methanol (1 mL), distilled water (10 mL), and 0.5N HCl (1 mL) were added thereto. The organic layer obtained as described above was dried over anhydrous sodium sulfate and concentrated under reduced pressure. The residue was subjected to column chromatography, thereby obtaining Compound 1k (17 mg, 87%).

EI-MS m/z: 1286 (M+)

Examples 2 and 3. Preparation of Compounds 2i and 3i

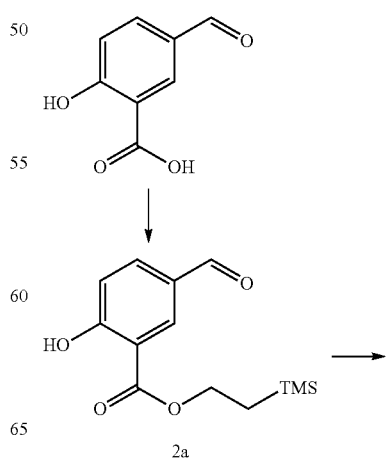

2a

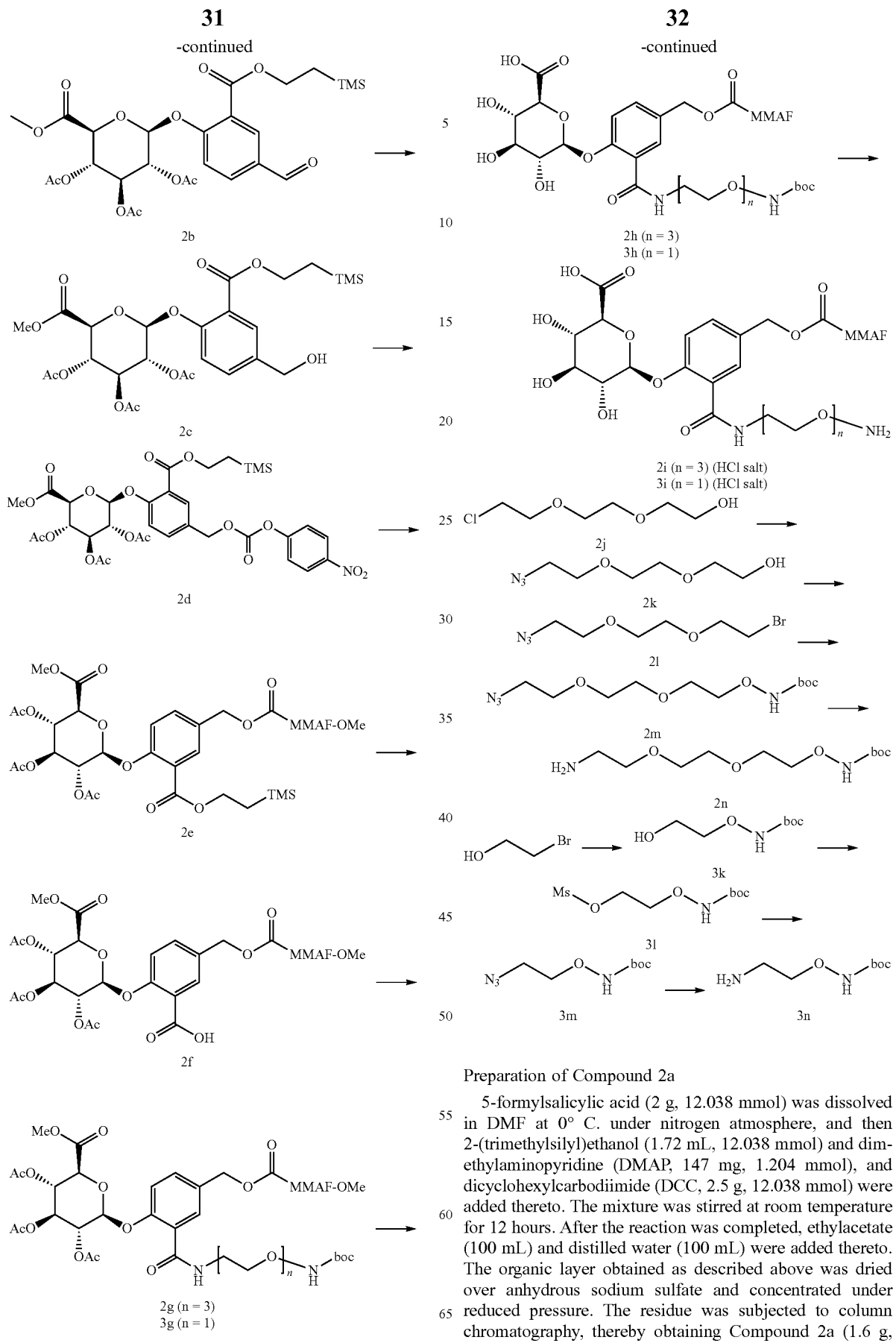

Preparation of Compound 2a 5-formylsalicylic acid (2 g, 12.038 mmol) was dissolved in DMF at 0° C. under nitrogen atmosphere, and then 2-(trimethylsilyl)ethanol (1.72 mL, 12.038 mmol) and dimethylaminopyridine (DMAP, 147 mg, 1.204 mmol), and dicyclohexylcarbodiimide (DCC, 2.5 g, 12.038 mmol) were added thereto. The mixture was stirred at room temperature for 12 hours. After the reaction was completed, ethylacetate (100 mL) and distilled water (100 mL) were added thereto. The organic layer obtained as described above was dried over anhydrous sodium sulfate and concentrated under reduced pressure. The residue was subjected to column chromatography, thereby obtaining Compound 2a (1.6 g, 50%).

$^1$H NMR (400 MHz, CDCl$_3$) δ 11.38 (s, 1H), 9.77 (s, 1H), 7.48 (d, J=8.4 Hz, 1H), 6.61 (dd, J=8.4, 2.0 Hz, 1H), 6.53 (d, J=2.0 Hz, 1H), 5.36-5.25 (m, 4H), 4.23 (m, 1H), 3.73 (s, 1H), 2.06 (s, 9H)

Preparation of Compound 2b

Compound 2a (60 mg, 0.225 mmol) was dissolved in acetonitrile (2 mL) at room temperature under nitrogen atmosphere, and then Compound C (90 mg, 0.225 mmol), silver oxide (209 mg, 0.900 mmol), and molecular sieve (90 mg) were added thereto. The mixture was stirred at room temperature for 2 hours. After the reaction was completed, ethylacetate (50 mL) and distilled water (30 mL) were added thereto. The organic layer obtained as described above was dried over anhydrous sodium sulfate and concentrated under reduced pressure. The residue was subjected to column chromatography, thereby obtaining Compound 2b (103 mg, 79%).

$^1$H NMR (400 MHz, CDCl$_3$) δ 9.93 (s, 1H), 8.22 (d, J=2.0 Hz, 1H), 7.97 (dd, J=6.4, 2.0 Hz, 1H), 7.26 (d, J=9.2 Hz, 1H), 5.42-5.27 (m, 4H), 4.42-4.30 (m, 2H), 4.24 (d, J=9.2 Hz, 1H), 3.70 (s, 3H), 2.06-2.04 (m, 9H), 1.14-1.08 (m, 2H), 0.07 (s, 9H)

Preparation of Compound 2c

Compound 2b (100 mg, 0.171 mmol) was dissolved in 2-propanol (0.3 mL) and chloroform (1.5 mL) at 0° C. under nitrogen atmosphere, and then silica gel (720 mg) and sodium borohydride (16 mg, 0.427 mmol) were added thereto. The mixture was stirred for 3 hours. After the reaction was completed, ethylacetate (50 mL) and distilled water (20 mL) were added thereto. The organic layer obtained as described above was dried over anhydrous sodium sulfate and concentrated under reduced pressure. The residue was subjected to column chromatography, thereby obtaining Compound 2c (94 mg, 94%).

$^1$H NMR (400 MHz, CDCl$_3$) δ 7.71 (d, J=2.0 Hz, 1H), 7.45 (dd, J=6.4, 2.0 Hz, 1H), 7.17 (d, J=8.4 Hz, 1H), 5.40-5.30 (m, 3H), 5.16-5.14 (m, 1H), 4.67 (s, 2H), 4.40-4.29 (m, 2H), 4.18 (d, J=8.8 Hz, 1H), 3.74 (s, 3H), 2.08-2.04 (m, 9H), 1.14-1.09 (m, 2H), 0.08 (s, 9H)

Preparation of Compound 2d

Compound 2c (90 mg, 0.154 mmol) was dissolved in DMF (1.0 mL) at 0° C. under nitrogen atmosphere, and then bis(4-nitrophenyl)carbonate (94 mg, 0.308 mmol) and DIPEA (40 uL, 0.231 mmol) were added thereto. The mixture was stirred at room temperature for 3 hours. After the reaction was completed, ethylacetate (50 mL) and distilled water (20 mL) were added thereto. The organic layer obtained as described above was dried over anhydrous sodium sulfate and concentrated under reduced pressure. The residue was subjected to column chromatography, thereby obtaining Compound 2d (104 mg, 90%).

$^1$H NMR (400 MHz, CDCl$_3$) δ 8.28 (m, 2H), 7.80 (d, J=2.4 Hz, 1H), 7.53 (dd, J=6.4, 2.0 Hz, 1H), 7.37 (m, 2H), 7.20 (d, J=8.8 Hz, 1H), 5.41-5.33 (m, 3H), 5.25 (s, 2H), 5.20-5.18 (m, 1H), 4.41-4.30 (m, 2H), 4.20 (d, J=8.8 Hz, 1H), 3.74 (s, 3H), 2.08-2.05 (m, 9H), 1.18-1.06 (m, 2H), 0.08 (s, 9H)

Preparation of Compound 2e

Compound 2d (1.5 g, 2.00 mmol) was dissolved in DMF (8 mL) at room temperature under nitrogen atmosphere, and then MMAF-Ome (1.34 g, 1.80 mmol) was added thereto. The resultant composition was treated with HOBT (54 mg, 0.4 mmol), pyridine (5.4 mL), and DIPEA (0.383 mL, 2.2 mmol). The mixture was stirred at room temperature for 12 hours. After the reaction was completed, ethylacetate (200 mL) and distilled water (300 mL) were added thereto. The organic layer obtained as described above was dried over anhydrous sodium sulfate and concentrated under reduced pressure. The residue was subjected to column chromatography, thereby obtaining Compound 2e (1.7 g, 70%).

EI-MS m/z: 1357 (M$^+$)

Preparation of Compound 2f

Compound 2e (1.7 g, 1.253 mmol) was dissolved in THF (15 mL) at 0° C. under nitrogen atmosphere, and then tetrabutylammonium fluoride (1M in THF) (2.5 mL, 2.506 mmol) was added thereto and stirred at room temperature for 4 hours. After the reaction was completed, ethylacetate (200 mL) and distilled water (300 mL) were added thereto. The organic layer obtained as described above was dried over anhydrous sodium sulfate and concentrated under reduced pressure. The residue was subjected to column chromatography, thereby obtaining Compound 2f (1.34 g, 85%).

EI-MS m/z: 1257 (M$^+$)

Preparation of Compound 2k

Compound 2j (10 g, 59.3 mmol) was dissolved in DMF (90 mL) at room temperature under nitrogen atmosphere, and then sodium azide (5.78 g, 88.9 mmol) was added thereto, and the mixture was stirred at 100° C. for 13 hours. After the reaction was completed, chloroform (200 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 2k (10.3 g, 99%).

$^1$H NMR (600 MHz, CDCl$_3$) δ 3.75-3.73 (m, 2H), 3.70-3.68 (m, 6H), 3.63-3.61 (m, 2H), 3.40 (t, J=5.4 Hz, 2H), 2.20 (t, J=6.0 Hz, 1H)

Preparation of Compound 2l

CBr$_4$ (21.4 g, 64.6 mmol) was dissolved in methylene chloride (MC, 100 mL) at 0° C. under nitrogen atmosphere, and then triphenylphosphine (16.9 g, 64.6 mmol) in methylene chloride (100 ml) and Compound 2k (10.3 g, 58.7 mmol) were added thereto, and the mixture was stirred at room temperature for 13 hours. After the reaction was completed, methylene chloride (300 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 2l (12 g, 85%).

$^1$H NMR (400 MHz, CDCl$_3$) δ 3.83 (t, J=6.4 Hz, 2H), 3.72-3.67 (m, 6H), 3.48 (t, J=6.0 Hz, 2H), 3.40 (t, J=4.8 Hz, 2H)

Preparation of Compound 2m

Compound 2l (1 g, 4.20 mmol) was dissolved in acetonitrile at room temperature under nitrogen atmosphere, and then N-Boc-hydroxylamine (643 mg, 4.82 mmol) and DBU (0.659 mL, 4.41 mmol) were added thereto, and the mixture was stirred at 60° C. for 13 hours. After the reaction was completed, methylene chloride (300 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 2m (748 mg, 70%).

$^1$H NMR (400 MHz, CDCl$_3$) δ 7.55 (s, 1H), 4.05-4.03 (m, 2H), 3.76-3.74 (m, 2H), 3.74-3.69 (m, 6H), 3.42 (t, J=4.8 Hz, 2H), 1.49 (s, 9H). EI-MS m/z: 291 (M+)

Preparation of Compound 2n

Compound 2m (200 mg, 0.688 mmol) was dissolved in methanol (5 mL), and then Pd/C (10%) (70 mg) was added thereto and stirred under hydrogen atmosphere for 3 hours. After the reaction was completed, the mixture was celite-filtered and concentrated under reduced pressure, thereby obtaining Compound 2n (180 mg, 98%).

$^1$H NMR (400 MHz, CDCl$_3$) δ 4.04-4.01 (m, 2H), 3.74-3.62 (m, 7H), 3.55 (t, J=5.2 Hz, 1H), 2.88 (t, J=5.2 Hz, 1H), 2.81 (t, J=5.2 Hz, 1H), 1.64 (s, 2H), 1.48 (s, 9H). EI-MS m/z: 265 (M+)

Preparation of Compound 2g

Compound 2f (1.34 g, 1.066 mmol) and Compound 2n (384 mg, 1.28 mmol) were dissolved in DMF (10 mL) at 0° C. under nitrogen atmosphere, and then DIPEA (464 uL, 2.665 mmol) and PyBOP (832 mg, 1.599 mmol) were added thereto and stirred at room temperature for 4 hours. After the reaction was completed, ethylacetate (200 mL) and distilled water (300 mL) were added thereto. The organic layer obtained as described above was dried over anhydrous sodium sulfate and concentrated under reduced pressure. The residue was subjected to column chromatography, thereby obtaining Compound 2g (1.2 g, 75%). EI-MS m/z: 1503 (M$^+$)

Preparation of Compound 2h

Compound 2g (530 mg, 0.352 mmol) was dissolved in methanol (10 mL) at −10° C. under nitrogen atmosphere, and then LiOH (147 mg, 7.98 mmol) in water (8 mL) was slowly added thereto and stirred for 1 hour. After the reaction was completed, chloroform (200 mL) and distilled water (30 mL, pH 2) were added thereto. The organic layer obtained as described above was dried over anhydrous sodium sulfate and concentrated under reduced pressure. The residue was subjected to column chromatography, thereby obtaining Compound 2h (260 mg, 45%). EI-MS m/z: 1349 (M$^+$)

Preparation of Compound 2i

Compound 2h (260 mg, 0.192 mmol) was dissolved in methylene chloride (4 mL) and water (2 mL) at 0° C. under nitrogen atmosphere, and then 4M-HCl (in dioxane, 4 mL) was added thereto and stirred at 0° C. for 1 hour. After the reaction was completed, the resultant was concentrated under reduced pressure, thereby obtaining Compound 2i (210 mg, 85%).

EI-MS m/z: 1249 (M$^+$)

Preparation of Compound 3k 2-bromoethanol (1.92 mL, 27.037 mmol) was dissolved in acetonitrile (15 mL) at room temperature under nitrogen atmosphere, and then Boc-hydroxylamine (3.0 g, 22.531 mmol) and DBU (3.7 mL, 24.8 mmol) were added thereto, and the mixture was stirred at 40° C. for 24 hours. After the reaction was completed, ethylacetate (100 mL) and distilled water (100 mL) were added thereto to extract an organic layer, and the extracted organic layer was dried over anhydrous sodium sulfate and concentrated under reduced pressure. The residue was subjected to column chromatography, thereby obtaining Compound 3k (2.75 g, 69%).

$^1$H NMR (400 MHz, CDCl$_3$) δ 7.28 (s, 1H), 3.93-3.91 (m, 2H), 3.76-3.74 (m, 2H), 1.50 (s, 9H).

Preparation of Compound 3l

Compound 3k (2.75 g, 15.697 mmol) was dissolved in THF (30 mL) at 0° C. under nitrogen atmosphere, and then TEA (3.3 mL, 23.518 mmol) and Ms$_2$O (3.28 g, 18.814 mmol) were added thereto, and the mixture was stirred at room temperature for 4 hours. After the reaction was completed, ethylacetate (200 mL) and distilled water (100 mL) were added thereto to extract an organic layer, and the extracted organic layer was dried over anhydrous sodium sulfate and concentrated under reduced pressure, thereby obtaining Compound 3l (3.83 g, 96%). $^1$H NMR (400 MHz, CDCl$_3$) δ 7.37 (s, 1H), 4.48-4.46 (m, 2H), 4.13-4.09 (m, 2H), 3.11 (s, 3H), 1.50 (s, 9H).

Preparation of Compound 3m

Compound 3l (3.83 g, 15.00 mmol) was dissolved in DMF (20 mL) at room temperature under nitrogen atmosphere, and then NaN$_3$ (1.95 g, 30.00 mmol) was added thereto, and the mixture was stirred at 60° C. for 13 hours. After the reaction was completed, ethylacetate (300 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 3m (2.02 g, 67%). $^1$H NMR (400 MHz, CDCl$_3$) δ 7.22-7.20 (m, 1H), 4.05-4.02 (m, 2H), 3.51-3.48 (m, 2H), 1.50 (s, 9H).

Preparation of Compound 3n

Compound 3m (2.02 g, 9.98 mmol) was dissolved in methanol (30 mL), and then Pd/C (10%) (1.0 g) and 4M HCl in dioxane (2.5 mL) were added thereto and stirred under hydrogen atmosphere for 3 hours. After the reaction was completed, the mixture was celite-filtered and concentrated under reduced pressure, thereby obtaining Compound 3n (1.98 g, 93%).

$^1$H NMR (400 MHz, CDCl$_3$) δ 10.26 (s, 1H), 8.05 (s, 3H), 3.91-3.88 (m, 2H), 3.1-2.98 (m, 2H), 1.44 (s, 9H).

Preparation of Compound 3g

Compound 2f (280 mg, 0.222 mmol) and Compound 3n (56 mg, 0.266 mmol) were dissolved in DMF (5 mL) at 0° C. under nitrogen atmosphere, and then DIPEA (58 uL, 0.334 mmol) and PyBOP (174 mg, 0.334 mmol) were added thereto and stirred at room temperature for 4 hours. After the reaction was completed, ethylacetate (100 mL) and distilled water (150 mL) were added thereto. The organic layer obtained as described above was dried over anhydrous sodium sulfate and concentrated under reduced pressure. The residue was subjected to column chromatography, thereby obtaining Compound 3g (221 mg, 69%). EI-MS m/z: 1415 (M$^+$)

Preparation of Compound 3h

Compound 3g (150 mg, 0.106 mmol) was dissolved in methanol (2 mL) at −10° C. under nitrogen atmosphere, and then LiOH (40 mg, 0.954 mmol) in water (2 mL) was slowly added thereto and stirred for 1 hour. After the reaction was completed, chloroform (150 mL) and distilled water (30 mL, pH 2) were added thereto. The organic layer obtained as described above was dried over anhydrous sodium sulfate and concentrated under reduced pressure. The residue was subjected to column chromatography, thereby obtaining Compound 3h (94 mg, 71%). EI-MS m/z: 1261 (M$^+$)

Preparation of Compound 3i

Compound 3h (90 mg, 0.071 mmol) was dissolved in methylene chloride (1 mL) at 0° C. under nitrogen atmosphere, and then trifluoroacetic acid (TFA, 0.2 mL) was added thereto and stirred at 0° C. for 3 hours. After the reaction was completed, the resultant was purified using Prep HPLC, thereby obtaining Compound 3i (47 mg, 52%).

EI-MS m/z: 1161 (M$^+$)

Example 4. Preparation of Compound 4i

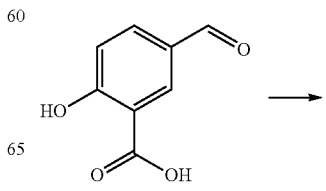

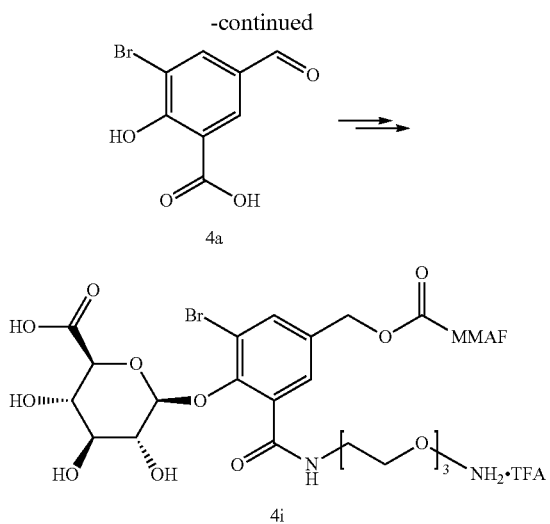

Preparation of 3-bromo-5-formylsalicylic acid (Compound 4a)

5-formylsalicylic acid (1 g, 6.019 mmol) was dissolved in DMF at 0° C. under nitrogen atmosphere, and then N-bromosuccinimide (1.07 g, 6.109 mmol) was added thereto and the mixture was stirred at 70° C. for 3 hours. After the reaction was completed, ethylacetate (100 mL), 2N—HCl aqueous solution (2 mL), and distilled water (100 mL) were added thereto. The organic layer obtained as described above was dried over anhydrous sodium sulfate and concentrated under reduced pressure. The residue was subjected to column chromatography, thereby obtaining Compound 4a (1.2 g, 84%). $^1$H NMR (400 MHz, DMSO-$d_6$) δ 9.64 (s, 1H), 8.19 (d, J=2.4 Hz, 1H), 8.00 (d, J=2.0 Hz, 1H), 3.16 (s, 1H)

Compound 4i was prepared using prepared 3-bromo-5-formylsalicylic acid (Compound 4a) by a method similar to methods of preparing Compounds 2i and 3i of Examples 2 and 3.

EI-MS m/z: 1328 (M+)

Examples 5 to 7. Preparation of LCB14-0648, LCB14-0664, and LCB14-0663

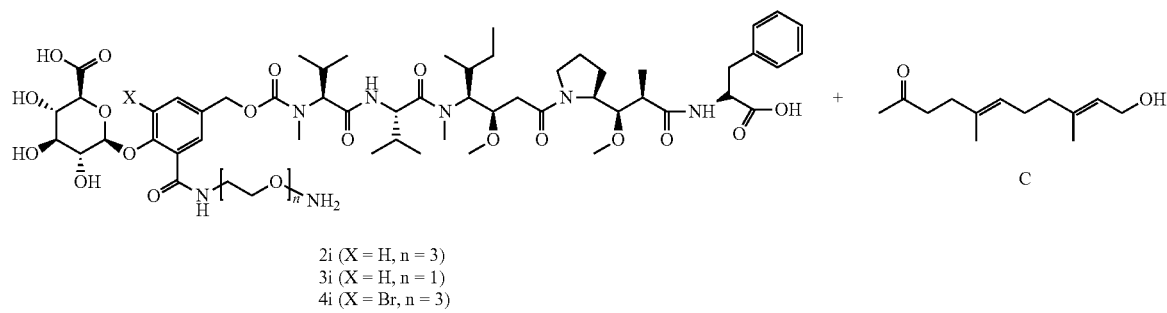

2i (X = H, n = 3)
3i (X = H, n = 1)
4i (X = Br, n = 3)

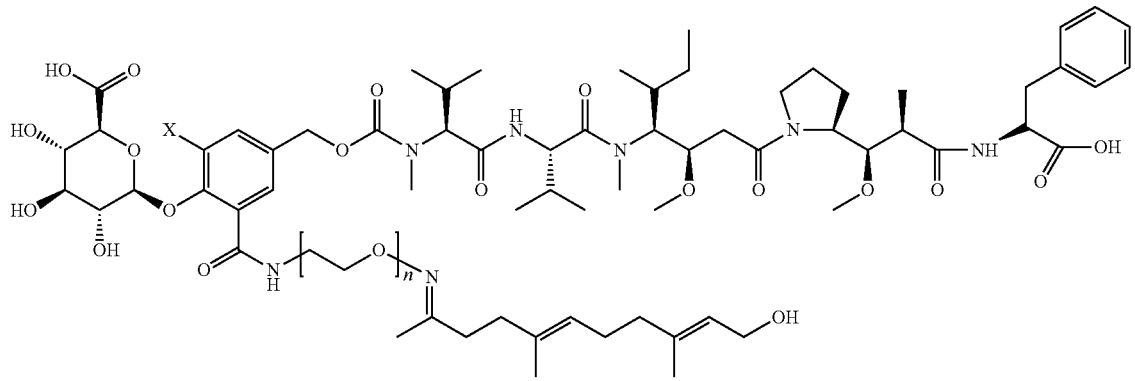

LCB14-0648 (X = H, n = 3)
LCB14-0664 (X = H, n = 1)
LCB14-0663 (X = Br, n = 3)

Compound C was prepared by a method disclosed in Korean Patent Laid-Open Publication No. 10-2014-0035393.

Example 5. Preparation of LCB14-0648

Compound 2i (20 mg, 0.014 mmol) was dissolved in ethanol (0.7 mL) at room temperature under nitrogen atmosphere, and then Compound C (3.7 mg, 0.017 mmol) was added thereto, and the mixture was stirred at 45° C. for 2 hours. After the reaction was completed, LCB14-0648 (10.2 mg, 49%) was obtained using Prep HPLC.

EI-MS m/z: 1441 (M$^+$)

LCB14-0663 (Example 6) and LCB14-0664 (Example 7) were prepared by a method similar to the method of preparing LCB14-0648 (Example 5).

EI-MS of LCB14-0663: m/z: 1520 (M$^+$)
EI-MS of LCB14-0664: m/z: 1353 (M$^+$)

Comparative Example 1. Preparation of Compound 5k

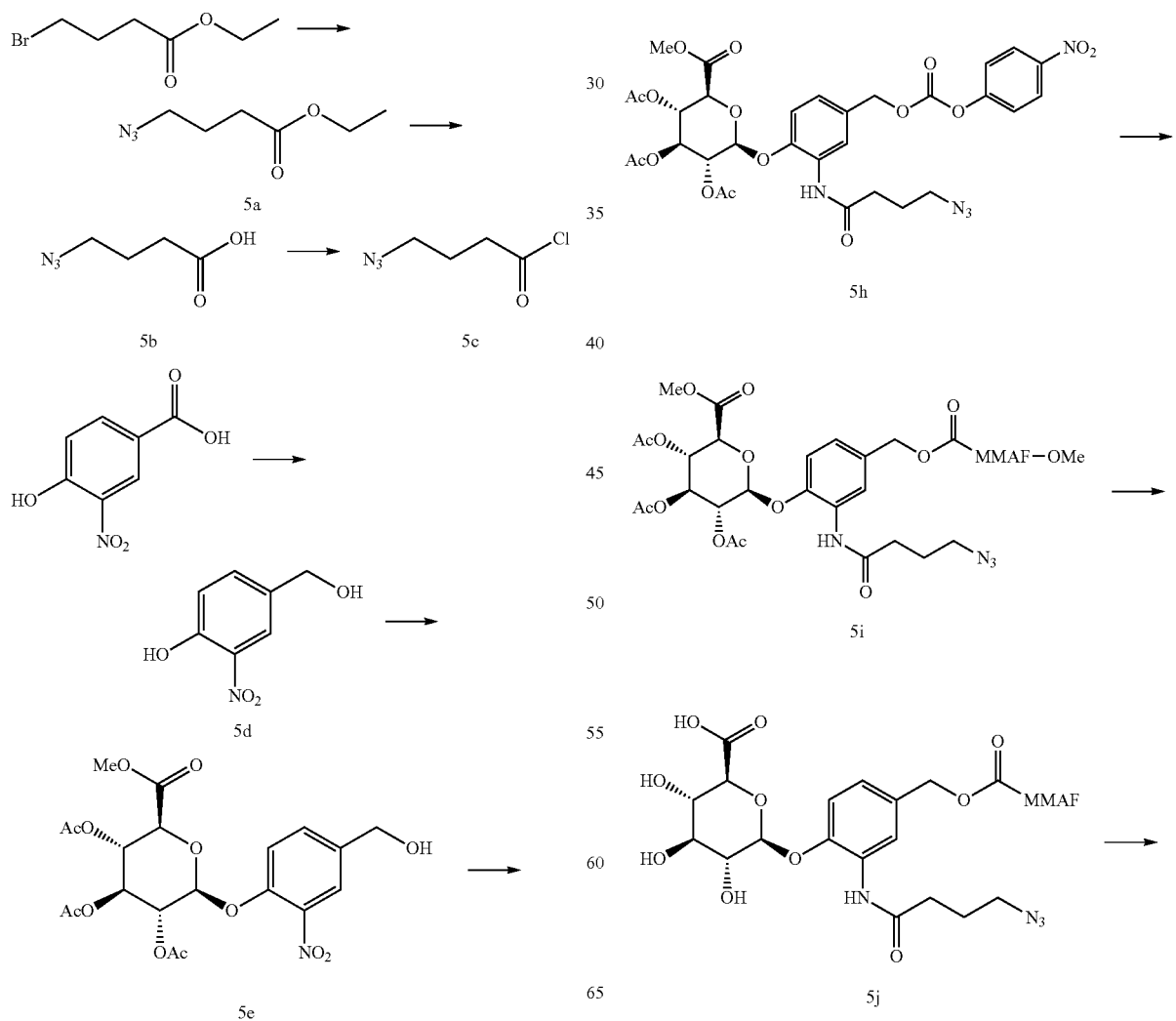

-continued

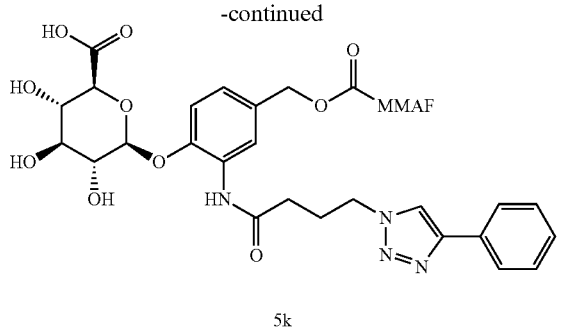

5k

Preparation of Compound 5a

Ethyl 4-bromobutanoate (5.0 mL, 34.604 mmol) was dissolved in MeOH (75 mL) at room temperature under nitrogen atmosphere, and then sodium azide (4.5 g, 69.209 mmol) in water (25 mL) was added thereto and stirred at 85° C. for 8 hours. After the reaction was completed, the solvent was concentrated under reduced pressure, and chloroform (300 mL) and distilled water (200 mL) were added thereto. The organic layer obtained as described above was dried over anhydrous sodium sulfate and concentrated under reduced pressure. The residue was subjected to column chromatography, thereby obtaining Compound 5a (5.1 g, 94%).

$^1$H NMR (600 MHz, CDCl$_3$) δ 4.15 (q, J=7.2 Hz, 2H), 3.36 (t, J=7.2 Hz, 2H), 2.41 (t, J=7.2 Hz, 2H), 1.94-1.89 (m, 2H), 1.28 (t, J=8.4 Hz, 3H).

Preparation of Compound 5b

Compound 5a (2.0 g, 12.725 mmol) was dissolved in MeOH (32 mL) at 0° C. under nitrogen atmosphere, and then KOH (3.56 g, 63.625 mmol) in water (26 mL) was slowly added thereto and stirred at room temperature for 6 hours. After the reaction was completed, the solvent was concentrated under reduced pressure, and chloroform (300 mL), 1N HCl (100 mL), and distilled water (100 mL) were added thereto. The organic layer obtained as described above was dried over anhydrous sodium sulfate and concentrated under reduced pressure. The residue was subjected to column chromatography, thereby obtaining Compound 5b (1.28 g, 78%).

$^1$H NMR (600 MHz, CDCl$_3$) δ 3.38 (t, J=7.2 Hz, 2H), 2.48 (t, J=7.2 Hz, 2H), 1.95-1.90 (m, 2H).

Preparation of Compound 5c

Compound 5b (850 mg, 6.580 mmol) was dissolved in MeOH (10 mL) at 0° C. under nitrogen atmosphere, and then oxalyl chloride (1.1 mL, 13.160 mmol) and DMF (1 drop) were added thereto and stirred at room temperature for 6 hours. After the reaction was completed, the solvent was concentrated under reduced pressure, such that Compound 5c (965 mg, Qu) corresponding to a crude product was obtained and used in the next reaction without purification.

Preparation of Compound 5d 4-hydroxy-3-nitrobenzoic acid (5 g, 27.304 mmol) was dissolved in THF (120 mL) at 0° C. under nitrogen atmosphere, and then 1M BH3-THF complex (54.6 mL, 54.6 mmol) was added thereto and stirred at room temperature for 20 hours. After the reaction was completed, ethylacetate (200 mL), 0.5N HCl (20 mL), and distilled water (100 mL) were added thereto. The organic layer obtained as described above was dried over anhydrous sodium sulfate and concentrated under reduced pressure. The residue was subjected to column chromatography, thereby obtaining Compound 5d (4.20 g, 91%).

$^1$H NMR (600 MHz, CD3OD) δ 8.06 (d, J=1.2 Hz, 1H), 7.59 (dd, J=1.2, 7.8 Hz, 1H), 7.12 (d, J=8.4 Hz, 1H), 4.83 (s, 2H)

Preparation of Compound 5e

Compound 5d (937 mg, 5.539 mmol) was dissolved in acetonitrile (15 mL) at room temperature under nitrogen atmosphere, and Compound 5c (2.0 g, 5.035 mmol), silver oxide (4.66 g, 20.108 mmol), and molecular sieve (2.0 g) were added thereto, and stirred at room temperature for 14 hours. After the reaction was completed, the mixture was celite-filtered, and the filtrate was concentrated under reduced pressure. The residue was subjected to column chromatography, thereby obtaining Compound 5e (1.0 g, 40%).

$^1$H NMR (600 MHz, CDCl$_3$) δ 7.81 (d, J=1.8 Hz, 1H), 7.54 (dd, J=1.8, 6.6 Hz, 1H), 7.37 (d, J=8.4 Hz, 1H), 5.37-5.27 (m, 3H), 5.20 (d, J=6.6 Hz, 1H), 4.72 (d, J=6.0 Hz, 2H), 4.21 (d, J=9.0 Hz, 1H), 3.75 (s, 3H), 2.12 (s, 3H), 2.06 (s, 3H), 2.05 (s, 3H), 2.04-2.02 (m, 1H).

Preparation of Compound 5f

Compound 5e (900 mg, 6.35 mmol) was dissolved in ethylacetate (100 mL), and then platinum (IV) oxide (84.2 mg, 0.370 mmol) was added thereto and stirred at room temperature under hydrogen atmosphere for 3 hours. After the reaction was completed, the mixture was celite-filtered, and the filtrate was concentrated under reduced pressure, such that Compound 5f (700 mg, 83%) corresponding to a crude product was obtained and used in the next reaction without purification.

Preparation of Compound 5g

Compound 5f (350 mg, 0.768 mmol) was dissolved in MC (10 mL) at 0° C. under nitrogen atmosphere, and then Compound 5c (136 mg, 0.921 mmol) and DIPEA (268 uL, 1.536 mmol) were added thereto and stirred at room temperature for 20 minutes. After the reaction was completed, ethylacetate (50 mL) and distilled water (50 mL) were added thereto. The organic layer obtained as described above was dried over anhydrous sodium sulfate and concentrated under reduced pressure. The residue was subjected to column chromatography, thereby obtaining Compound 5g (280 mg, 65%).

$^1$H NMR (600 MHz, CDCl$_3$) δ 8.37 (d, J=1.2 Hz, 1H), 8.00 (s, 1H), 7.07 (dd, J=1.8, 6.6 Hz, 1H), 6.93 (d, J=8.4 Hz, 1H), 5.43-5.28 (m, 3H), 5.06 (d, J=7.8 Hz, 1H), 4.63 (s, 2H), 4.19 (d, J=9.6 Hz, 1H), 3.76 (s, 3H), 3.44-3.41 (m, 2H), 2.56 (t, J=7.8 Hz, 2H), 2.17-2.00 (m, 12H).

EI-MS m/z: 567 (M+)

Preparation of Compound 5h

Compound 5g (250 mg, 0.441 mmol) was dissolved in DMF (4 mL) at 0° C. under nitrogen atmosphere, and then bis(4-nitrophenyl)carbonate (270 mg, 0.882 mmol) and DIPEA (115 uL, 0.661 mmol) were added thereto, and stirred at room temperature for 1 hour. After the reaction was completed, ethylacetate (50 mL) and distilled water (50 mL) were added thereto. The organic layer obtained as described above was dried over anhydrous sodium sulfate and concentrated under reduced pressure. The residue was subjected to column chromatography, thereby obtaining Compound 5h (290 mg, 90%).

$^1$H NMR (600 MHz, CDCl$_3$) δ 8.54 (d, J=1.8 Hz, 1H), 8.28-8.25 (m, 2H), 8.02 (s, 1H), 7.40-7.36 (m, 2H), 7.11 (dd, J=1.8, 6.6 Hz, 1H), 6.96 (d, J=8.4 Hz, 1H), 5.44-5.29 (m, 3H), 5.23 (s, 2H), 5.10 (d, J=7.8 Hz, 1H), 4.21 (d, J=9.6 Hz, 1H), 3.76 (s, 3H), 3.45-3.42 (m, 2H), 2.58 (t, J=7.2 Hz, 2H), 2.11-2.00 (m, 12H). EI-MS m/z: 732 (M+)

Preparation of Compound 5i

Compound 5h (250 mg, 0.341 mmol) was dissolved in DMF (4 mL) at room temperature under nitrogen atmosphere, and then MMAF-Ome (255 mg, 0.341 mmol) was added thereto. The resultant composition was treated with HOBT (9 mg, 0.068 mmol), pyridine (1.2 mL), and DIPEA (60 uL, 0.341 mmol). The obtained mixture was stirred at room temperature for 2 days. After the reaction was completed, ethylacetate (50 mL), 2N HCl (5 mL), and distilled water (50 mL) were added thereto. The organic layer obtained as described above was dried over anhydrous sodium sulfate and concentrated under reduced pressure. The residue was subjected to column chromatography, thereby obtaining Compound 5i (340 mg, 74%).

EI-MS m/z: 1339 (M+)

Preparation of Compound 5j

Compound 5i (210 mg, 0.156 mmol) was dissolved in methanol (2 mL) at 0° C. under nitrogen atmosphere, and then LiOH.H₂O (66 mg, 1.560 mmol) in water (2 mL) was added thereto. The obtained mixture was stirred at room temperature for 1.5 hours. After the reaction was completed, chloroform (50 mL), methanol (5 mL), distilled water (50 mL), and 0.5N HCl (5 mL) were added thereto. The organic layer obtained as described above was dried over anhydrous sodium sulfate and concentrated under reduced pressure. The residue was subjected to column chromatography, thereby obtaining Compound 5j (107 mg, 57%).

EI-MS m/z: 1184 (M+)

Preparation of Compound 5k

Compound 5j (10 mg, 0.008 mmol) and phenylacetylene (0.92 uL, 0.008 mmol) were dissolved in ethanol (150 ul) and water (10 ul) at room temperature under nitrogen atmosphere, and then 0.1M CuSO₄ aqueous solution (10 ul) and 1.0M sodium ascorbate aqueous solution (10 ul) were added thereto. The obtained mixture was stirred at room temperature for 5 hours. After the reaction was completed, ethylacetate (10 mL) and distilled water (5 mL) were added thereto. The organic layer obtained as described above was dried over anhydrous sodium sulfate and concentrated under reduced pressure. The residue was subjected to column chromatography, thereby obtaining Compound 5k (5 mg, 46%).

EI-MS m/z: 1286 (M+)

Example 8. Preparation of Compound 6e

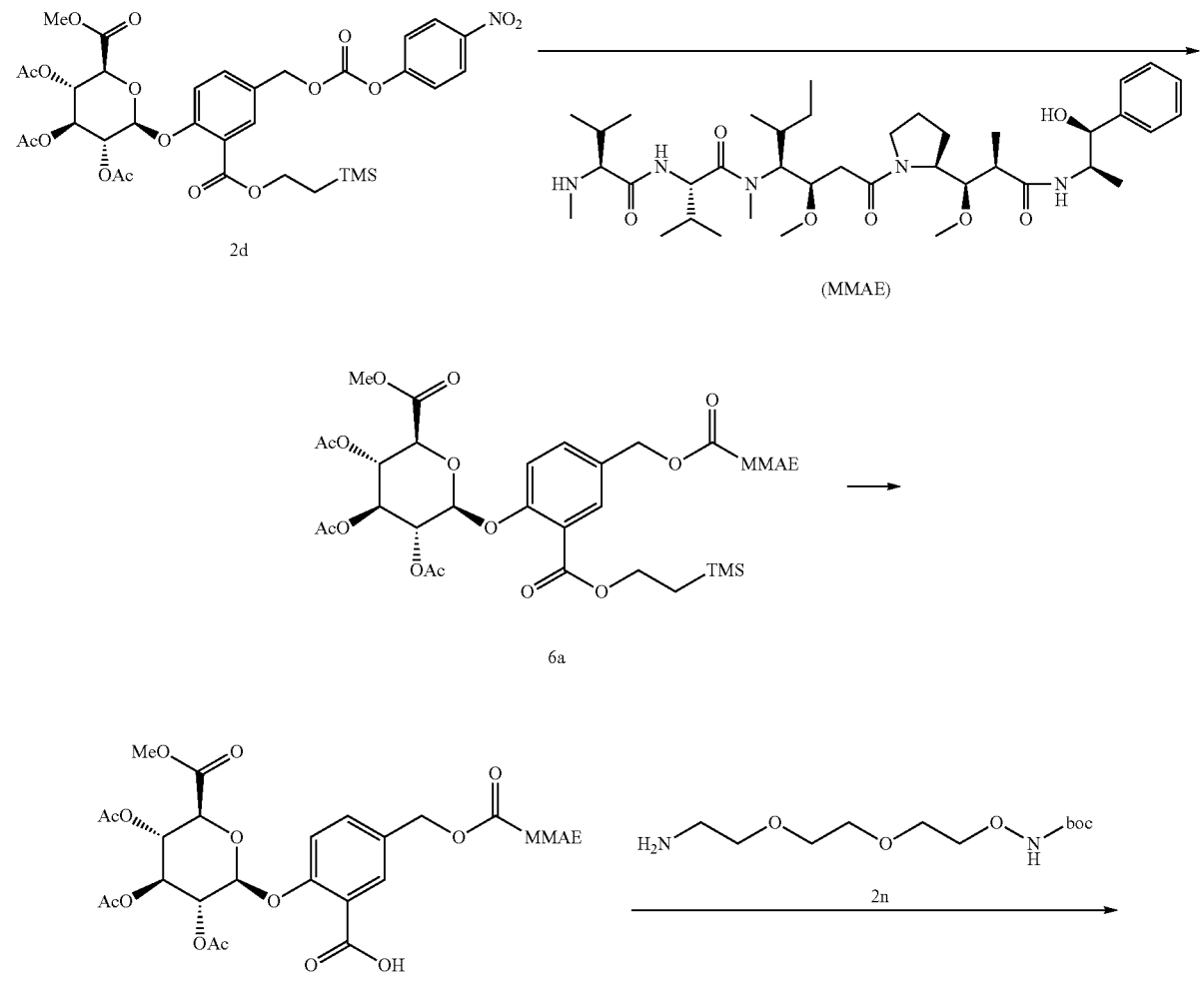

-continued

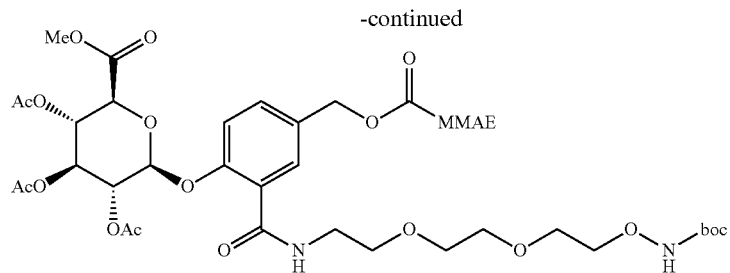

6c

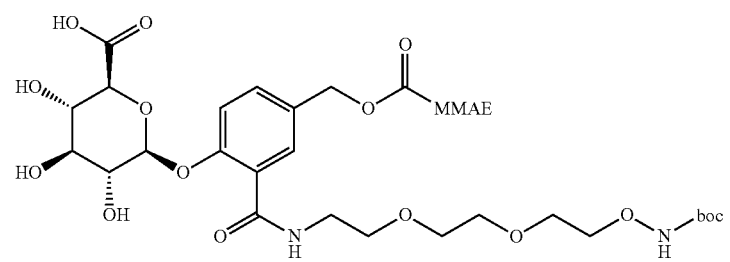

6d

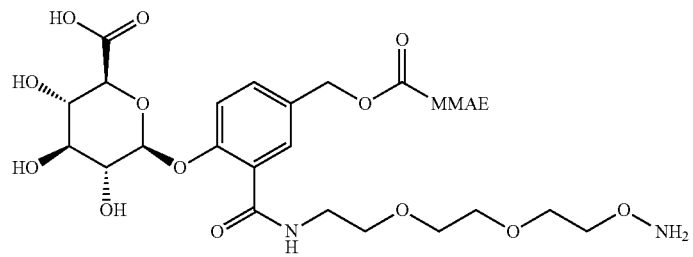

6e (HCl salt)

Preparation of Compound 6a

Compound 2d (229 mg, 0.30 mmol) was dissolved in DMF (2 mL) at room temperature under nitrogen atmosphere, and then MMAE (1.34 g, 1.80 mmol) was added thereto. The resultant composition was treated with HOBT (8.2 mg, 0.06 mmol), pyridine (0.8 mL), and DIPEA (56 uL, 0.29 mmol). The mixture was stirred at room temperature for 12 hours. After the reaction was completed, ethylacetate (100 mL) and distilled water (100 mL) were added thereto. The organic layer obtained as described above was dried over anhydrous sodium sulfate and concentrated under reduced pressure. The residue was subjected to column chromatography, thereby obtaining Compound 6a (239 mg, 65%).

EI-MS m/z: 1328 (M+)

Preparation of Compound 6b

Compound 6a (239 mg, 0.18 mmol) was dissolved in THF (5 mL) at 0° C. under nitrogen atmosphere, and then tetrabutylammonium fluoride (1M in THF) (540 uL, 2.50.58 mol) was added thereto and stirred at room temperature for 3 hours. After the reaction was completed, methylene chloride (100 mL) and distilled water (100 mL) were added thereto. The organic layer obtained as described above was dried over anhydrous sodium sulfate and concentrated under reduced pressure. The residue was subjected to column chromatography, thereby obtaining Compound 6b (212 mg, 95%).

EI-MS m/z: 1228 (M$^+$)

Preparation of Compound 6c

Compound 6b (200 mg, 0.16 mmol) and Compound 2n (51 mg, 0.19 mmol) were dissolved in DMF (4 mL) at 0° C. under nitrogen atmosphere, and then DIPEA (42 uL, 0.32 mmol) and PyBOP (126 mg, 0.24 mmol) were added thereto and stirred at room temperature for 4 hours. After the reaction was completed, ethylacetate (100 mL) and distilled water (100 mL) were added thereto. The organic layer obtained as described above was dried over anhydrous sodium sulfate and concentrated under reduced pressure. The residue was subjected to column chromatography, thereby obtaining Compound 6c (142 mg, 60%).

EI-MS m/z: 1474 (M+)

Preparation of Compound 6d

Compound 6c (142 mg, 0.09 mmol) was dissolved in methanol (2 mL) at −20° C. under nitrogen atmosphere, and then LiOH (36 mg, 0.86 mmol) in water (2 mL) was slowly added thereto and stirred at 0° C. for 1 hour. After the reaction was completed, chloroform (100 mL), distilled water (50 mL), and 2N—HCl aqueous solution (2 mL) were added thereto. The organic layer obtained as described above was dried over anhydrous sodium sulfate and concentrated under reduced pressure. The residue (6d, 128 mg, 99%) was used in the next reaction without purification.

EI-MS m/z: 1334 (M$^+$)

Preparation of Compound 6e

Compound 6d (105 mg, 0.08 mmol) was dissolved in methylene chloride (3 mL) at −20° C. under nitrogen atmosphere, and then 4M-HCl (in dioxane, 1 mL) was added thereto and stirred at 0° C. for 1 hour. After the reaction was completed, the resultant was concentrated under reduced pressure. The residue was purified using preparative HPLC, thereby obtaining Compound 6e (47 mg, 46%).

EI-MS m/z: 1234 (M$^+$)

Experimental Example 1. Responsiveness Comparison Test with Respect to β-Glucuronidase in Order to Compare Responsiveness of Compound 1k of Example 1 and Compound 5k of Comparative Example 1 to/3-Glucuronidase with Each Other, Comparison Test was Performed as Follows Compound 1k of Example 1 and Compound 5k of Comparative Example 1 were each prepared as 500 μM and 50 μM DMSO stock solutions. Reaction solutions in which 880 μL of phosphate buffer saline (PBS) solution and 100 μL of Compound 1k and Compound 5k stock solutions were mixed with each other, respectively, were prepared (final concentrations thereof were 50 μM and 5 μM, respectively). After 20 μL of E. coli β-glucuronidase enzyme (1 mg/ml, Sigma: E.C.3.2.1.31 Type IX-A; 1 mg/mL in PBS; 3.6 μg, 13 μmol) was added to the reaction solutions, reactions were initiated in a constant temperature water bath at 37° C. 100 μL of the mixed solutions were dispensed at 0 min, 25 min, 60 min, and 90 min, respectively, and 200 μL of acetonitrile was added thereto. MMAF released from each of the supernatants obtained by performing centrifugation (4° C., 15 min, 14000 rpm) on the mixture samples was quantitatively analyzed using LC-MS/MS (the experiment was performed by a method similar to a method disclosed in U.S. Pat. No. 8,568,728, hereby incorporated by reference).

Figure 2:
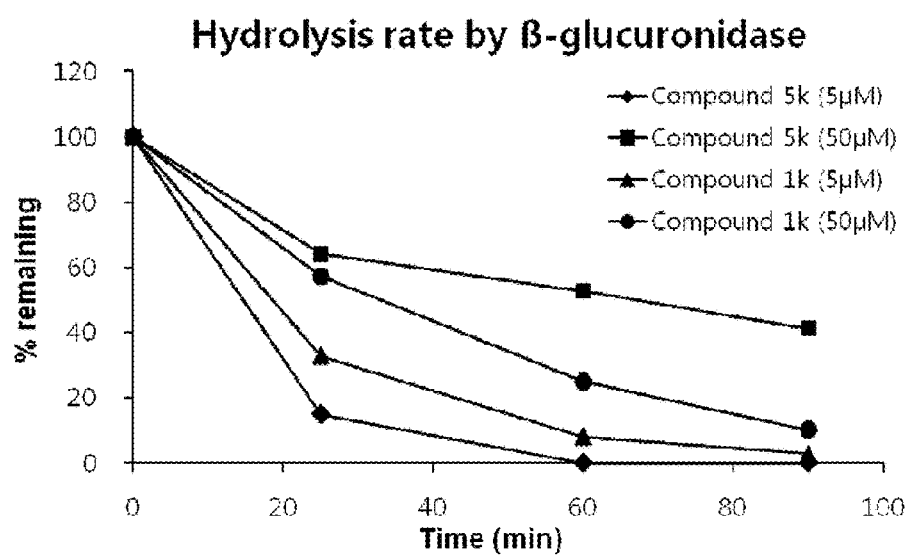
FIG. 2 is a graph depicting the hydrolysis of a linker by β-glucuronidase from Experimental Example 1.

The test results were illustrated in FIG. 2, and it was confirmed from FIG. 2 that MMAF was significantly rapidly released from each Compound 1k of Example 1 and Compound 5k of Comparative Example 1 through a 1,6-elimination reaction after enzyme reactions by β-glucuronidase (U.S. Pat. No. 8,568,728, hereby incorporated by reference).

Experimental Example 2. Plasma Stability Comparison Test

The plasma stability of Compound 1k of Example 1 and Compound 5k of Comparative Example 1 were compared.

10 μL of Compound 1k or 5k was dissolved in DMSO at 5 mM, and each composition was mixed with 990 μL of mouse plasma, thereby preparing 50 μM samples, for assessing plasma stability. The plasma/compound solutions were incubated at 37° C. for 6 days. During the 6-day incubation, 100 μL aliquots were taken at 0, 1, 2, 3, and 6 days and mixed with 200 μL of acetonitrile containing an internal standard for monitoring plasma protein precipitation. Supernatants were obtained by centrifuging the acetonitrile/plasma samples (4° C., 15 min, 14000 rpm), and the amount of each compound and product was quantified by performing LC-MS/MS on the supernatants. (The experiment was performed using similar to those disclosed in J. Chromatography B, 780:451-457 (2002)).

Figure 3:
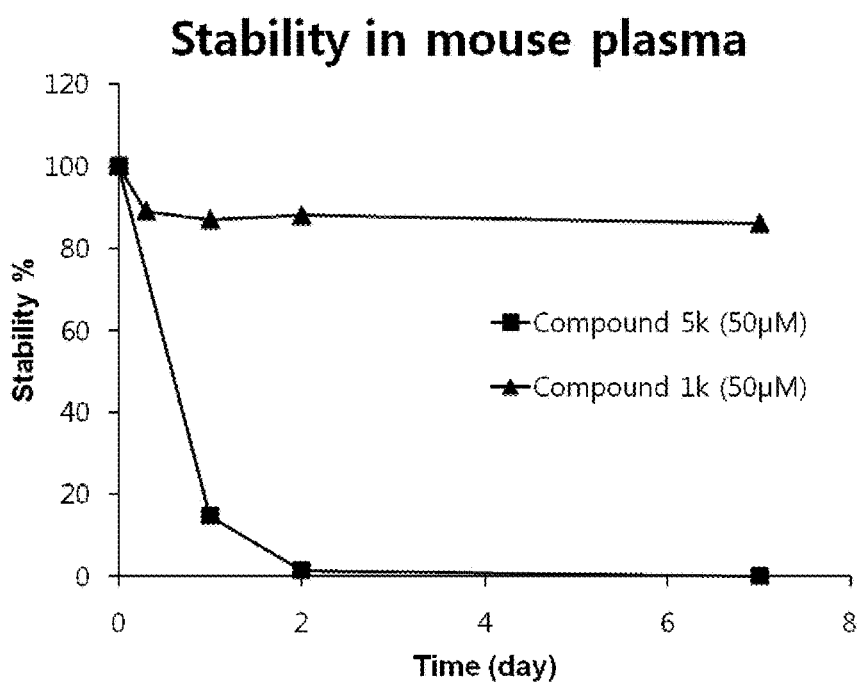
FIG. 3 is a graph depicting the plasma stability of two drug-linker conjugates from Experimental Example 2.

Results obtained for Compound 1k of Example 1 and Compound 5k of Comparative Example 1 using LS-MS/MS are illustrated in FIG. 3 and Table 1. The stability of Compound 5k of Comparative Example 1 and stability of Compound 1k of Example 1 was 14% and 80% at 1 day, respectively. Thus, the stability of Compound 1k of Example 1 in mouse plasma was superior to Compound 5k of Comparative Example 1.

TABLE 1

Stability of Compound 1k and Compound 5k in mouse plasma

|  | Compound 1k of Example 1 | Compound 5k of Comparative Example 1 |
|---|---|---|
| Linker | Glucuronide | Glucuronide |
| Plasma Stability (mouse plasma) | 80% Stability (@7 days) | 14% Stability (@1 day) |
| Result | Stable | Unstable |

Experimental Example 3. Plasma Stability Test

Figure 4:
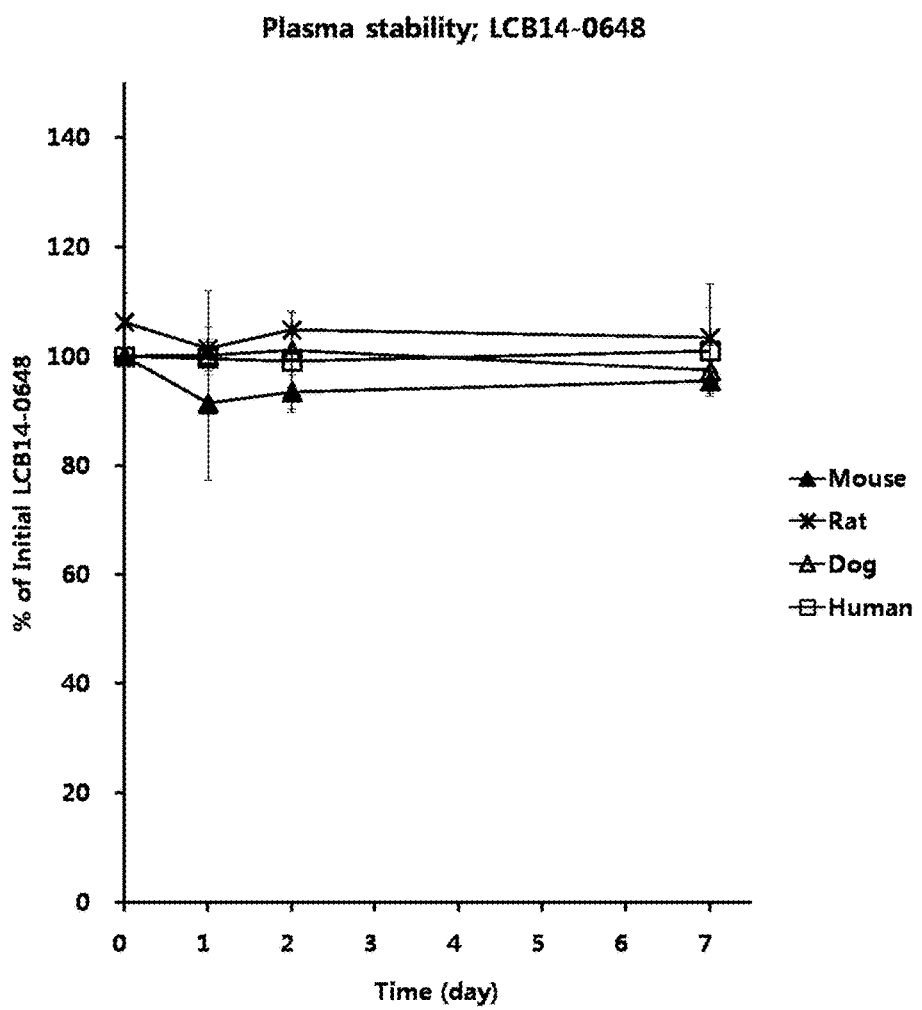
FIG. 4 is a graph depicting the plasma stability of LCB14-0648 prepared in Example 5.
Figure 5:
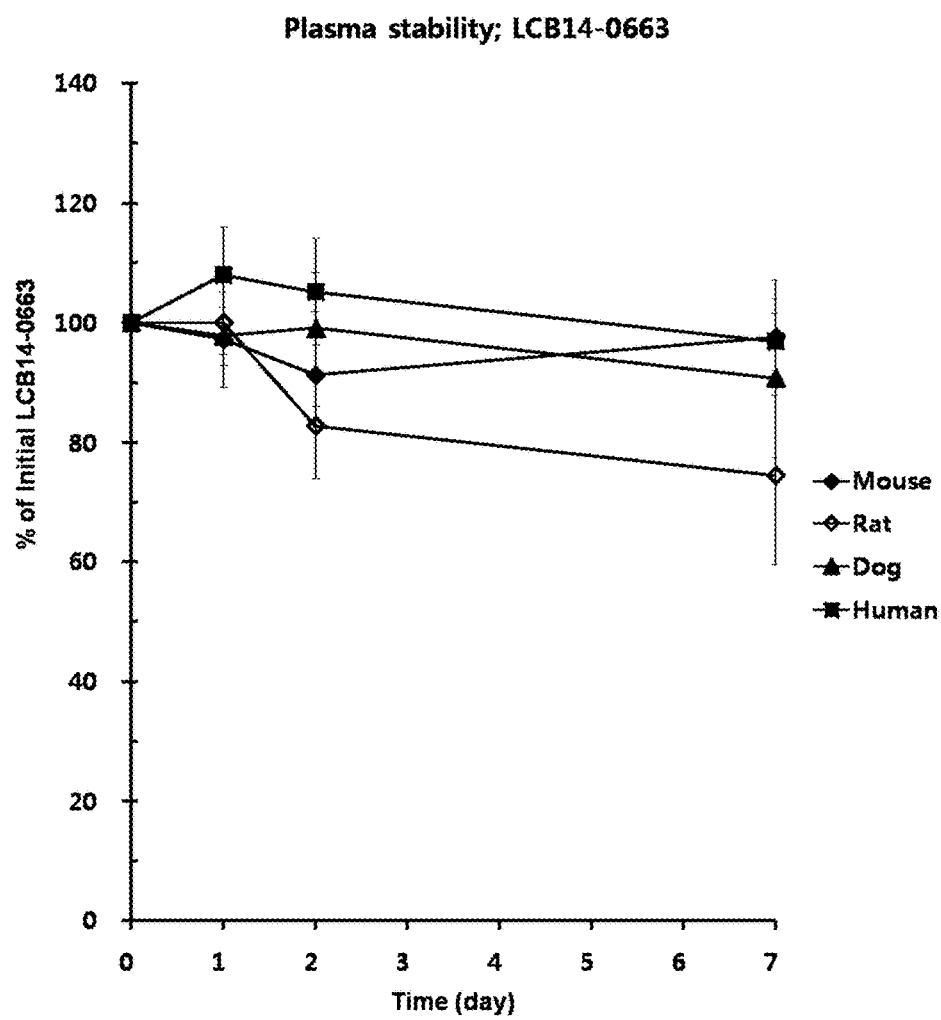
FIG. 5 is a graph depicting the plasma stability of LCB14-0663 prepared in Example 6.
Figure 6:
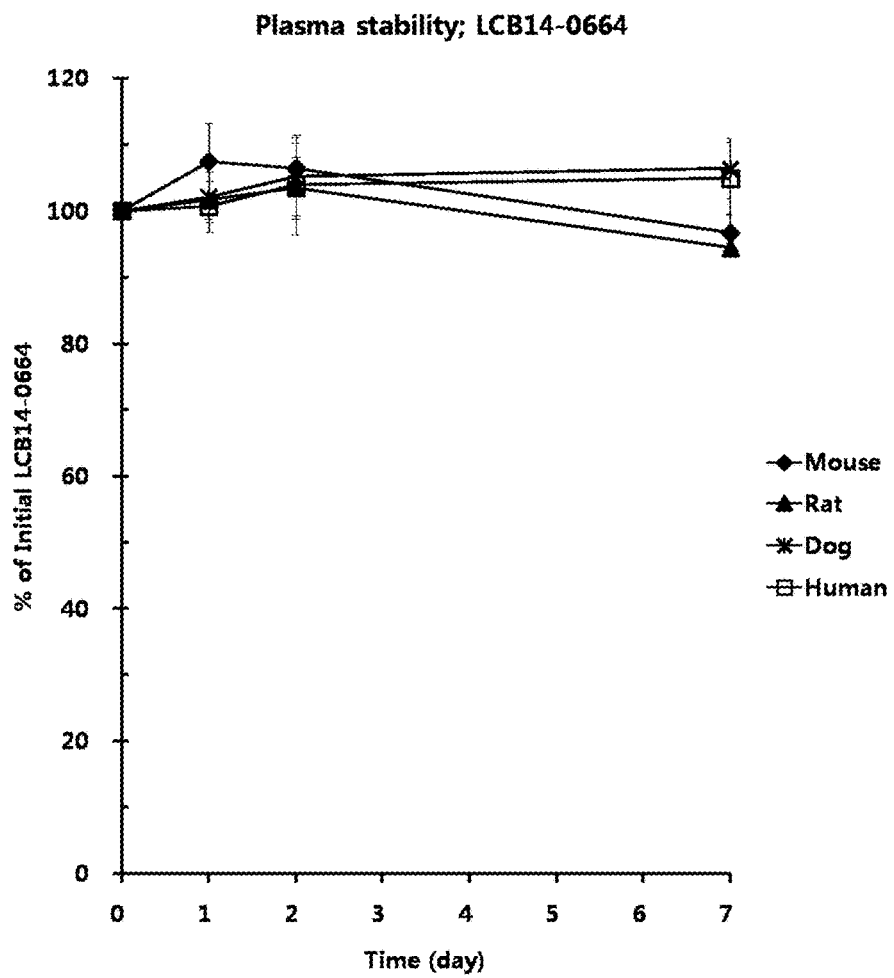
FIG. 6 is a graph depicting the plasma stability of LCB14-0664 prepared in Example 7.
Figure 7:
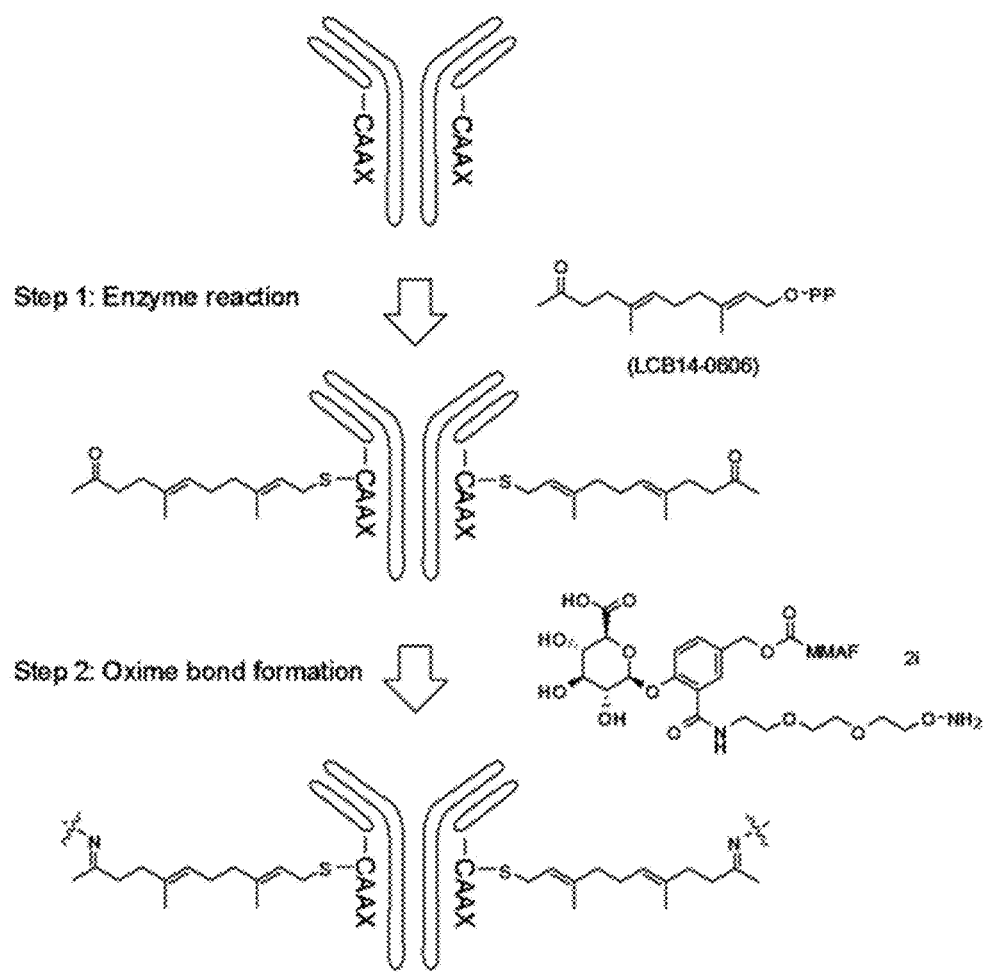
FIG. 7 displays a strategy for conjugating a drug to an antibody.

In order to confirm stability in various plasmas using LCB14-0648 (Example 5), LCB14-0664 (Example 6), and LCB14-0663 (Example 7), which were compounds prepared in Examples 5 to 7, plasma stability test was performed by the same method as in Experimental Example 2, and the results were illustrated in FIGS. 4 to 6.

It was confirmed that LCB14-0648 (Example 5), LCB14-0664 (Example 6), and LCB14-0663 (Example 7), which were compounds prepared in Examples 5 to 7, were all stable in mouse, rat, dog, and human plasmas up to 7 days.

Examples 9 to 14: Preparation of Antibody-Drug Conjugates (ADCs)

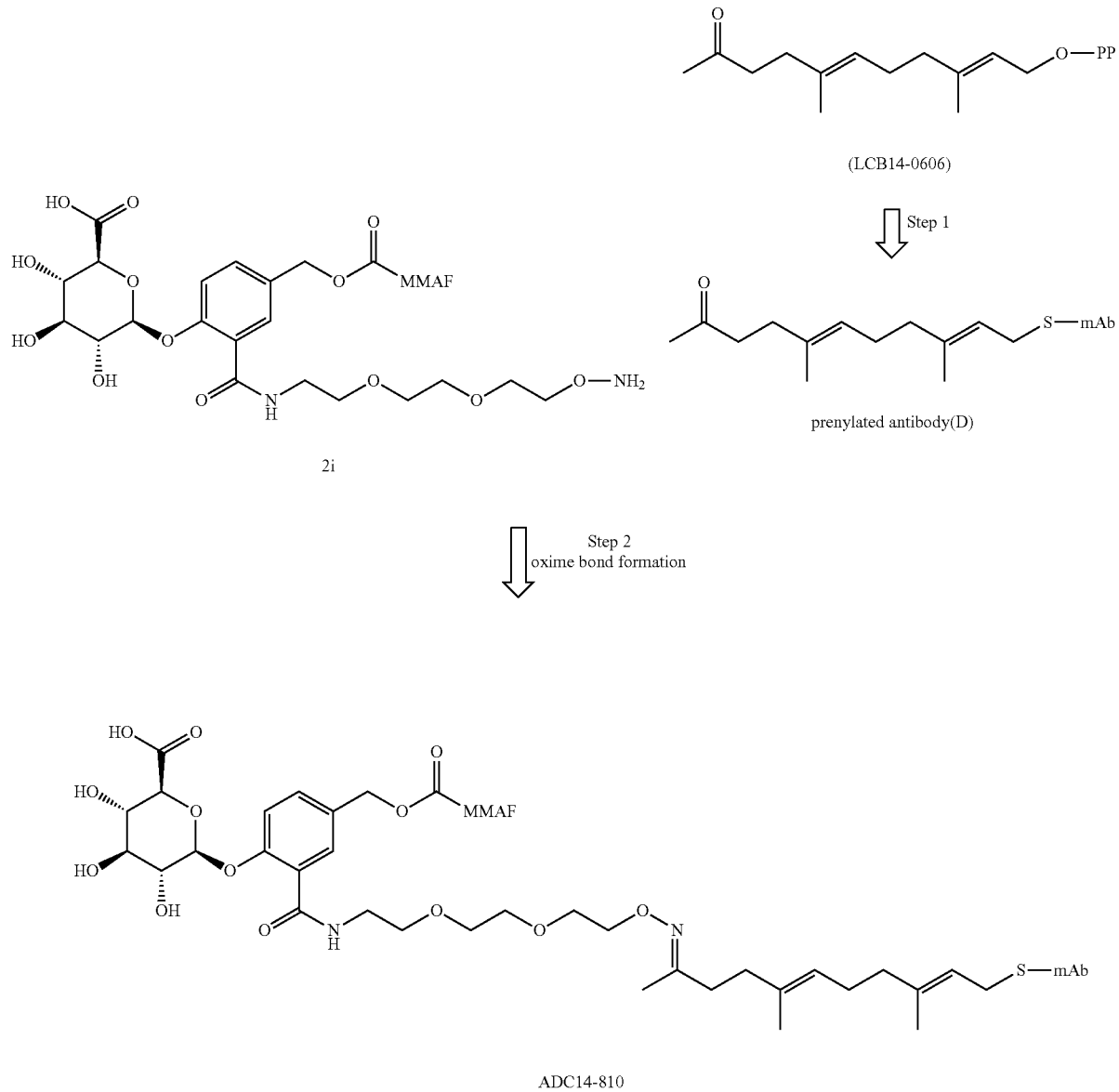

ADC14-810

Figure 8:
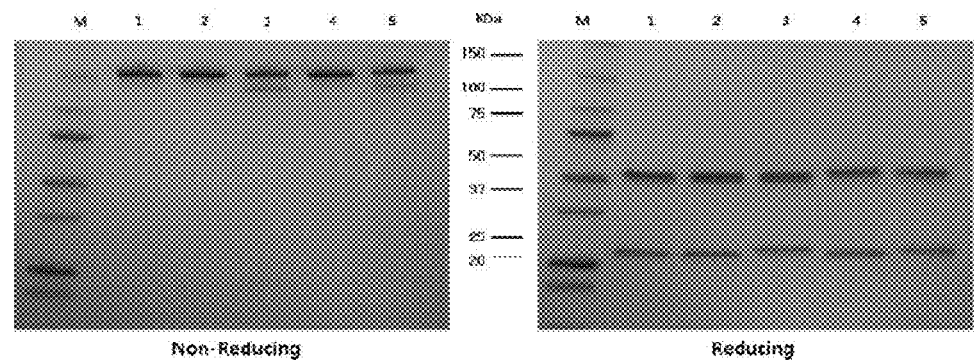
FIG. 8 consists of two panels, labeled panel (A) and (B).
Figure 8:
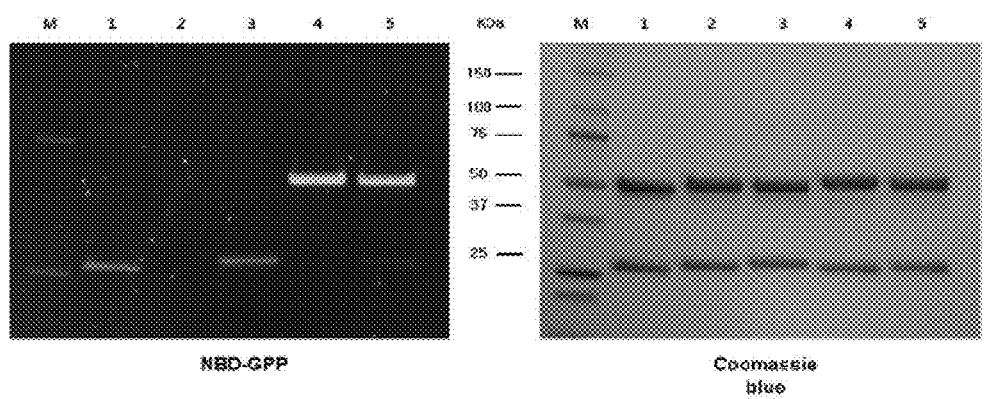

Example 9. SDS-PAGE Analysis of Antibodies Comprising a Peptide Linker and an Isoprenylation Sequence Erbitux(LC)-G7CVIM was prepared by adding the polypeptide sequence GGGGGGGCVIM (SEQ ID NO: 1) ("G7CVIM") to the C-terminus of the light chain of anti-EGFR antibody cetuximab (Erbitux®). Erbitux(HC)-G7CVIM was prepared by adding the polypeptide sequence GGGGGGGCVIM (SEQ ID NO: 1) to the C-terminus of the heavy chain of cetuximab. Erbitux(LC, HC)-G7CVIM was prepared by adding the polypeptide sequence GGGGGGGCVIM (SEQ ID NO: 1) to the C-terminus of both the light chain and heavy chain of cetuximab. The three cetuximab derivatives were denatured and analyzed by SDS-polyacrylamide gel electrophoresis (SDS-PAGE). Briefly, 2 µg of each protein sample was analyzed under non-reducing and reducing conditions (FIG. 8). Erbitux (LC)-G7CVIM, Erbitux(HC)-G7CVIM, and Erbitux(LC, HC)-G7CVIM antibodies ran as intact antibodies under non-reducing conditions (FIG. 8; top left), and the antibodies ran as a light chains of about 25 kDa and heavy chains of about 50 kDa under reducing conditions (FIG. 8, top right).

Example 10. Preparation of NBD-GPP

Tris-ammonium[3,7-dimethyl-8-(7-nitro-benzo[1,2,5]oxadiazol-4-ylamino)-octa-2,6-diene-1]pyrophosphate (NBD-GPP) is prepared by a method similar to the method described in JACS 128:2822-2835 (2006) (hereby incorporated by reference).

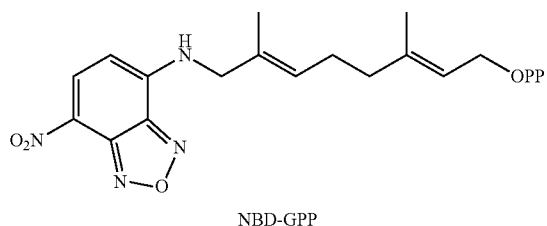

NBD-GPP $^1$H NMR (600 MHz, D$_2$O) δ 8.51 (d, J=9 Hz, 1H), 6.37 (d, J=9 Hz, 1H), 5.50 (t, J=6.6 Hz, 1H), 5.42 (t, J=6.6 Hz, 1H), 4.43 (t, J=6.6 Hz, 2H), 4.08 (s, 2H), 2.22 (m, 2H), 2.10 (t, J=7.2 Hz, 2H), 1.69 (s, 6H).

Example 11. Prenylation of Cetuximab-GGGGGGG-CVIM

Erbitux(LC)-G7CVIM, Erbitux(LHC)-G7CVIM, and Erbitux(LC, HC)-G7CVIM, as described in Example 9, were isoprenylated with the fluorescent analog of geranyl pyrophosphate 3,7-dimethyl-8-(7-nitro-benzo[1,2,5]oxadiazol-4-ylamino)-octa-2,6-diene-1-pyrophosphate (NBD-GPP) using farnesyltransferase (FTase) using the reaction mixture in Table 2.

TABLE 2

| NBD-GPP Prenylation Reaction Mixture | | | |
|---|---|---|---|
| Reagents | Stock Conc. | Vol. (ul) | Final conc. |
| 10x prenylation buffer | 10 | 1 | 1 |
| Antibody, (uM) | 18 | 1.7 | 3 |
| Substrate NBD-GPP, (uM) | 250 | 1 | 25 |
| FTase #344145, (uM) | 5.319 | 1.5 | 0.8 |
| DDW | | 4.8 | |
| Total volume (ul) | | 10 | |

The 10× prenylation buffer consisted of 500 mM Tris HCl (pH 7.4), 50 mM MgCl$_2$, 0.1 mM ZnCl$_2$, and 50 mM dithiothreitol (DTT). NBD-GPP was obtained from Jena Bioscience (Cat. No. LI-014). FTase was obtained from Calbiochem (#344145). The reaction was incubated at 30° C. for 3 hours and subsequently analyzed by SDS-PAGE (FIG. 8). SDS-PAGE analysis indicated that NBD-GPP was incorporated into the light chains of Erbitux(LC) G7-CVIM and Erbitux(LC, HC) G7-CVIM and the heavy chains of Erbitux(HC) G7-CVIM and Erbitux(LC, HC) G7-CVIM, but not the light chain of Erbitux(HC) G7-CVIM or the heavy chain of Erbitux(LC) G7-CVIM.

Erbitux(LC)-G7CVIM, Erbitux(LHC)-G7CVIM, and Erbitux(LC, HC)-G7CVIM, as described above, were prenylated with substrate LCB14-0606 using farnesyltransferase (FTase) using the reaction mixture in Table 3.

TABLE 3

| LCB14-0606 Prenylation Reaction Mixture | | | |
|---|---|---|---|
| Reagents | Stock Conc. | Vol. (ul) | Final conc. |
| 10x prenylation buffer | 10 | 5.5 | 1 |
| Antibody, (uM) | 120 | 11.0 | 24 |

TABLE 3-continued

| LCB14-0606 Prenylation Reaction Mixture | | | |
|---|---|---|---|
| Reagents | Stock Conc. | Vol. (ul) | Final conc. |
| Substrate, (uM) | 1000 | 7.9 | 144 |
| FTase #344145, (uM) | 5.319 | 2.1 | 0.2 |
| DDW | | 28.5 | |
| Total volume (ul) | | 55 | |

The 10× prenylation buffer consisted of 500 mM Tris HCl (pH 7.4), 50 mM MgCl$_2$, 0.1 mM ZnCl$_2$, and 50 mM dithiothreitol (DTT). LCB14-0606 was prepared according to the methods disclosed in U.S. Patent Application Publication No. 2012/0308584 (hereby incorporated by reference).

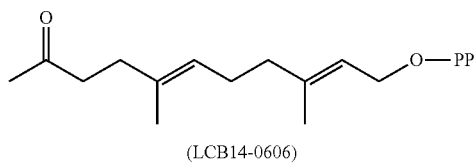

(LCB14-0606)

Figure 9:
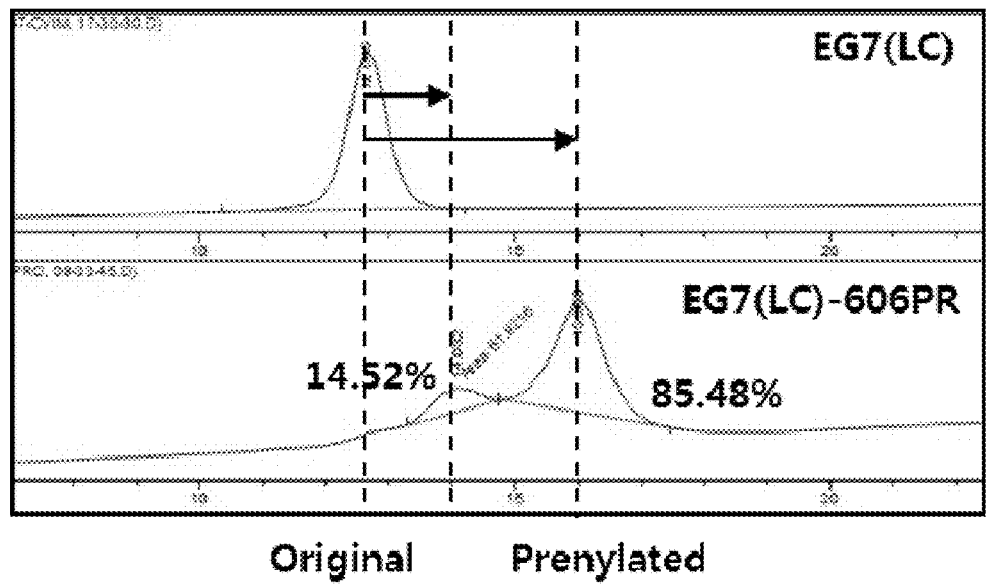
FIG. 9 consists of three panels, labeled panel (A), (B) and (C). Each panel shows HPLC traces for antibodies before and after prenylation with the LCB14-0606 substrate. Prenylation increases the hydrophobicity of an antibody, thereby increasing its retention time in the HPLC column. The HPLC traces show that the prenylation reaction with the CVIM sequence (SEQ ID NO: 2) is highly efficient, resulting in high yields.
Figure 9:
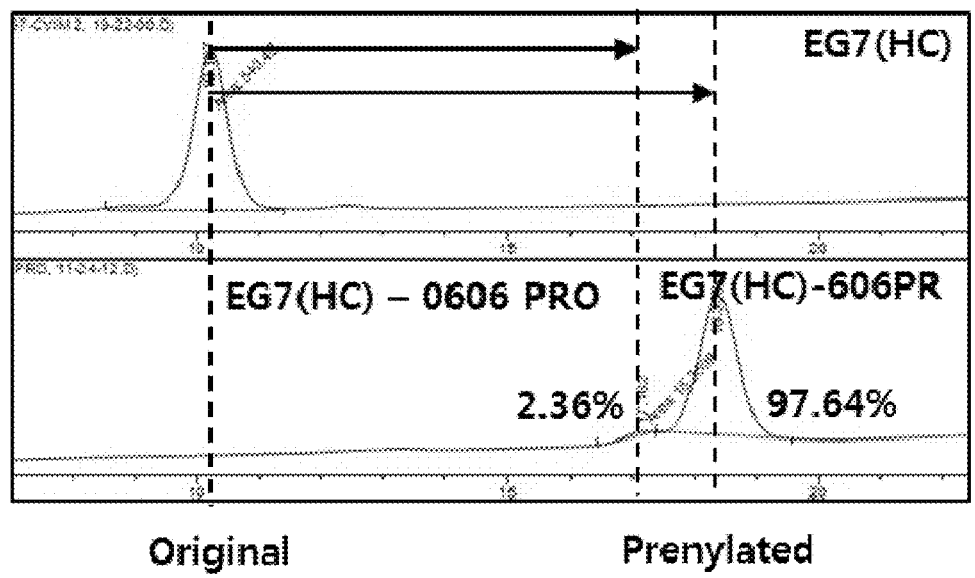
Figure 9:
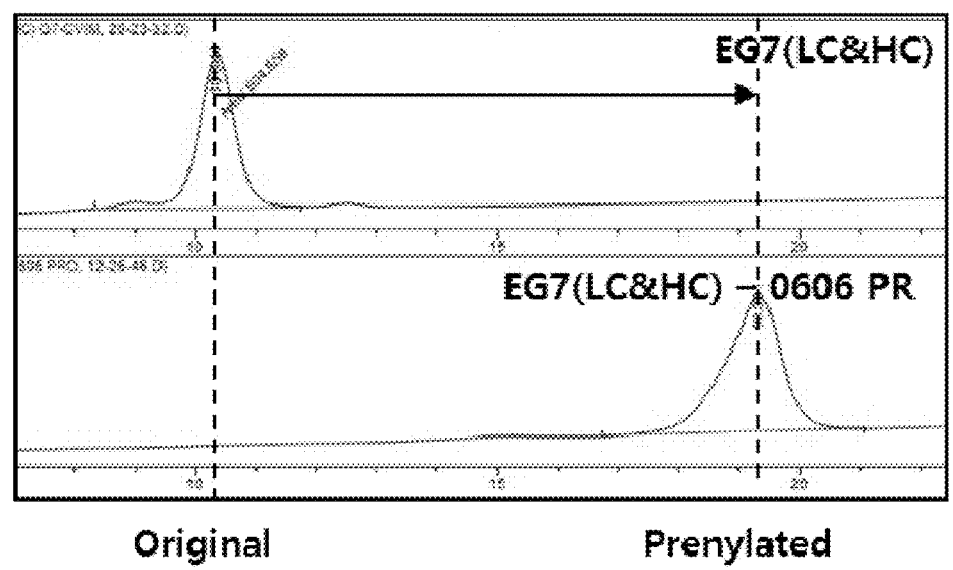

FTase was obtained from Calbiochem (#344145). The reaction was incubated at 30° C. for 16 hours. The prenylated antibodies were analyzed by HPLC (FIG. 9) using a phenyl-5PW column (Tosoh Bioscience) and a decreasing ammonium sulfate/increasing acetonitrile gradient (Table 4). Each prenylated antibody displayed a longer retention time than its non-prenylated parent, consistent with an increase in hydrophobicity associated with the isoprenyl and NBD moieties.

TABLE 4

| Heavy and Light Chain Analysis Settings (phenyl-5PW column) | | | | | |
|---|---|---|---|---|---|
| Heavy chain analysis setting Flow rate: 1 ml/min | | | Light chain analysis setting Flow rate: 1 ml/min | | |
| Time | A | B | Time | A | B |
| initial | 60% | 40% | initial | 70% | 30% |
| 25 | 10% | 90% | 25 | 10% | 90% |
| 35 | 10% | 90% | 35 | 10% | 90% |

A: 1.5M NH$_4$SO$_4$ + 50 mM PO$_4^{3-}$
B: 50 mM PO$_4^{3-}$ + 20% acetonitrile

Example 12. Oxime Formation

The LCB14-0606-prenylated Erbitux(LC)-G7CVIM antibody was desalted using a PD-10 column and concentrated using a Vivaspin® 500 concentrator. The prenylated Erbitux (LV)-G7CVIM antibody was conjugated to the β-glucuronidase linker and MMAF (compound 2i; LCB14-0645) in a 100 mM sodium acetate buffer, pH 4.5, containing 10% DMSO, 12 μM antibody, and 360 uM of compound 2i at 30° C. for 24 hours with gentle shaking.

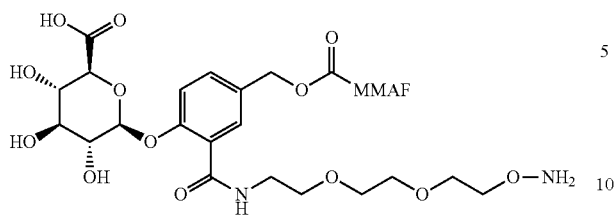

2i

TABLE 5
Ketone-alkoxyamine reaction mixture used for oxime formation.

| Reagents | Stock Conc. | Vol. (ul) | Final conc. |
|---|---|---|---|
| Prenylated Ab | 109 μM | 368.8 | 12 μM |
| LCB14-0645 | 10000 μM | 120.6 | 360 μM |
| DMSO | 100% | 214.4 | 10% |
| 0.2M Na-acetate (pH 4.5) | 0.2M | 1675.0 | 0.1M |
| DDW | | 971.2 | |
| Total volume (ul) | | 3350.0 | |

Figure 10:
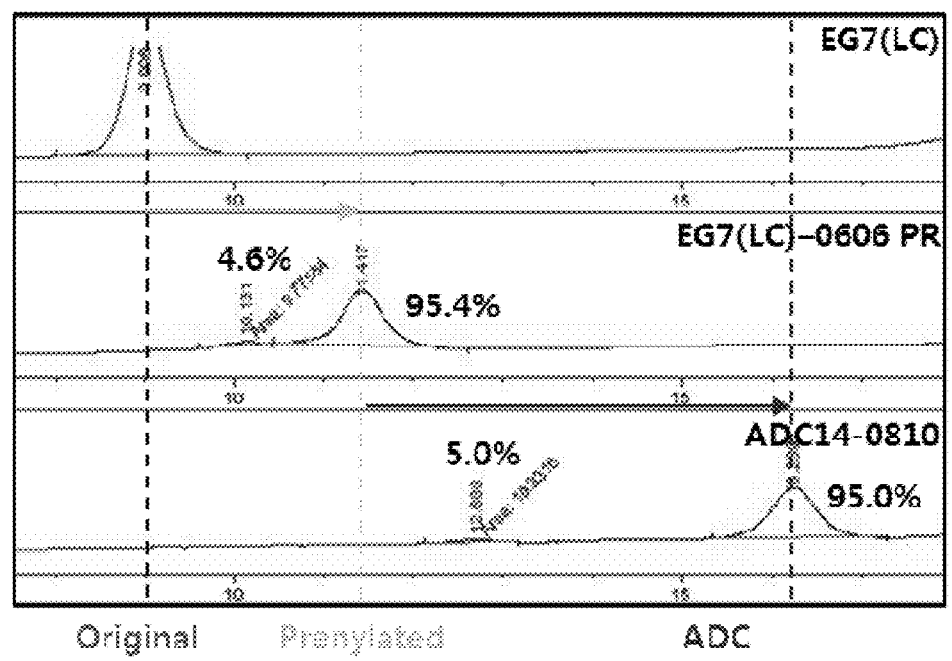
FIG. 10 shows HPLC traces for cetuximab with the linker/prenylation peptide sequence GGGGGGGCVIM (SEQ ID NO: 1) before prenylation (EG7(LC)), after prenylation with the LCB14-0606 substrate (EG7(LC)-0606PR), and after conjugation with MMAF (ADC14-0810). Both prenylation and conjugation increase the hydrophobicity of the antibody, thereby increasing its retention time in the HPLC column. The HPLC traces show that both the prenylation reaction and the conjugation reaction are highly efficient, resulting in high yields.

After incubation for 24 hours, the antibody-drug conjugate, named ADC14-0810, was purified by FPLC. The reaction mixture was analyzed by HPLC (FIG. 10) using a phenyl-5PW column (Tosoh Bioscience) and a decreasing ammonium sulfate/increasing acetonitrile gradient (Table 6). The antibody-drug conjugate displayed an increased retention time in the HPLC column relative to the antibody parent and the prenylated antibody, consistent with the addition of an hydrophobic peptide derivative to the antibody (i.e., monomethyl auristatin F).

TABLE 6

| Light Chain Analysis Settings (phenyl-5PW column) Flow rate: 1 ml/min | | |
|---|---|---|
| Time | A | B |
| initial | 70% | 30% |
| 25 | 10% | 90% |
| 35 | 10% | 90% |

A: 1.5M $NH_4SO_4$ + 50 mM $PO_4^{3-}$
B: 50 mM $PO_4^{3-}$ + 20% acetonitrile

Example 13. Preparation of Cetuximab (LC)-Glucuronide Linker-MMAE

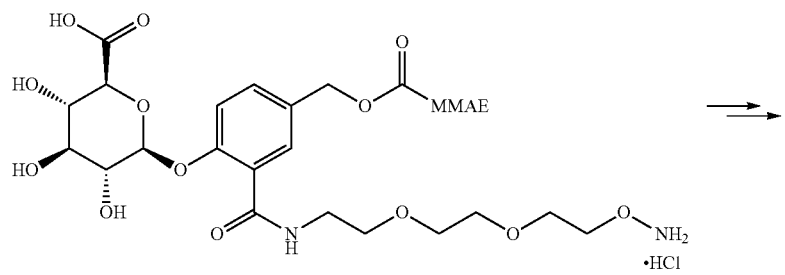

6e

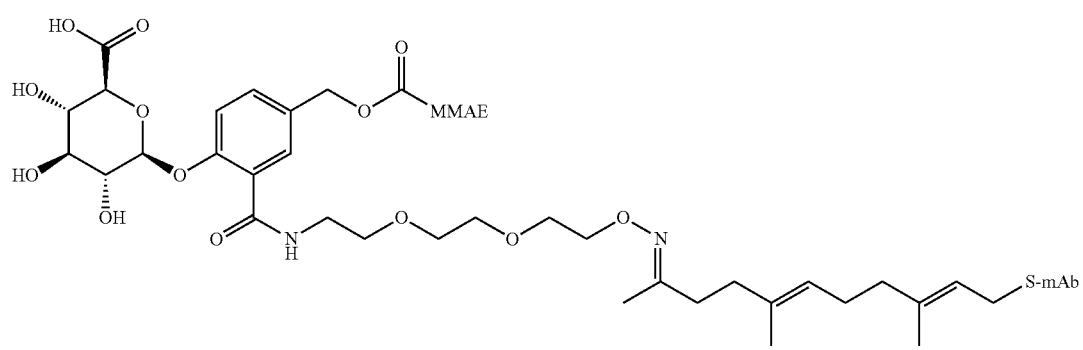

A cetuximab (LC)-glucuronide linker-MMAE antibody-drug conjugate is prepared using the prepared Compound 6e by a method similar to those disclosed in Examples 9-12.

Example 14. Preparation of Cetuximab (LC)-Glucuronide Linker-Amanitin

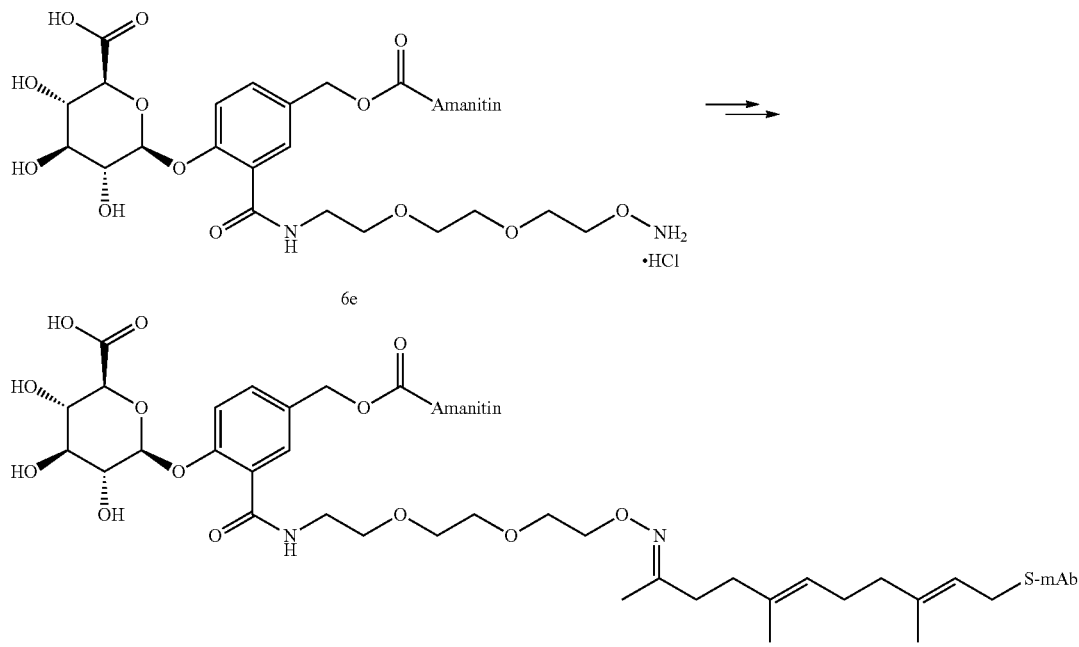

A cetuximab (LC)-glucuronide linker-Amanitin antibody-drug conjugate is prepared by a method similar to those disclosed in Examples 9-12.

Example 15. Flow Cytometry Analysis of Cetuximab (LC)-Glucuronide Linker-MMAF (ADC14-0810) Binding to A431 Cells A431 cells were labeled using anti-EGFR antibodies cetuximab (Erbitux®), Erbitux(LC)-G7CVIM, and ADC14-0810 (Erbitux(LC)-G7CVIM-LBG-MMAF) as primary antibodies. A431 cells are human squamous carcinoma cells, which express high levels of EGFR. Briefly, A431 cells were harvested with dissociation buffer (Gibco #13151-014). 200,000 cells per sample were blocked with 4% normal goat serum in phosphate buffered saline (PBS) on ice for 30 minutes. The cells were pelleted to remove the blocking buffer. The cells were then incubated with 0.5 µg/mL of each antibody in 100 µL of PBS containing 2% fetal bovine serum (FBS) on ice for 60 minutes. Human IgG$_1$ at 2 µg/mL was prepared in parallel as a negative control, and unlabeled cells were used as negative controls as well. Cells were washed three times with cold 2% FBS in PBS by centrifugation at 2000 rpm for 5 minutes. Next, 100 µL of 2 µg/mL phycoerythrin-conjugated secondary antibody (anti-human IgG$_1$-PE; BD 555787) in 2% FBS in PBS was added to the cells, and the mixture was incubated on ice for 30 minutes. The cells were washed three times with cold 2% FBS in PBS by centrifugation at 2000 rpm for 5 minutes. Labeled cells were analyzed on a BD FACSCanto II, and the resultant data was analyzed by FACS Express 3.0 software.

Figure 11:
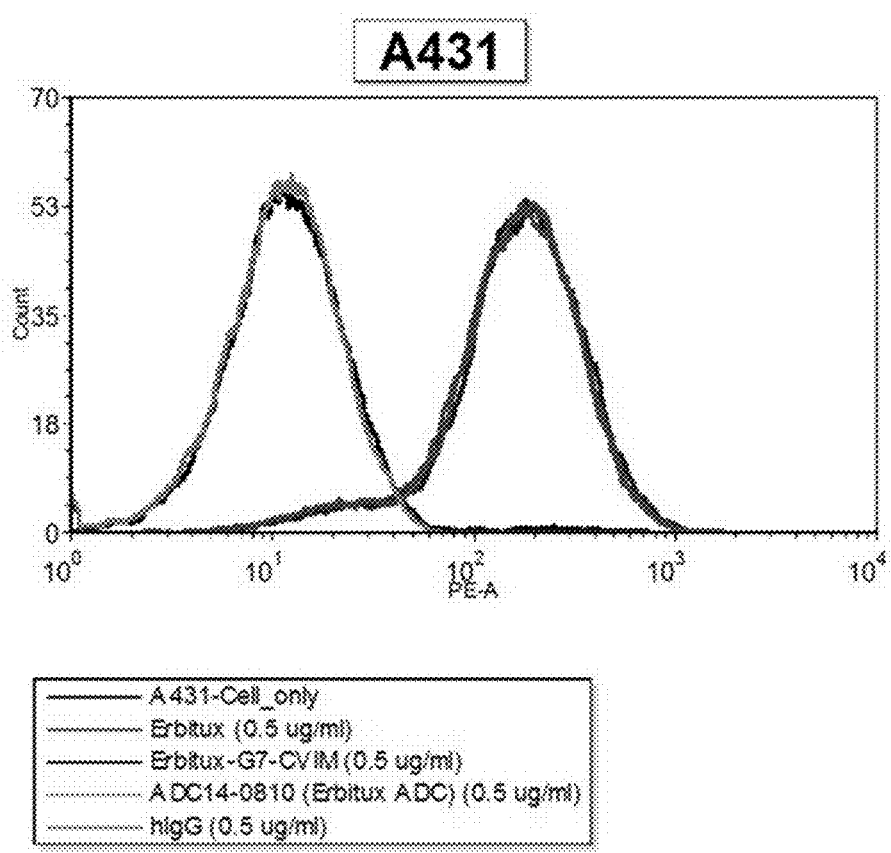
FIG. 11 shows flow cytometry results for A431 cells, which are human squamous carcinoma cells, labeled using anti-EGFR antibodies cetuximab (Erbitux®), Erbitux(LC)-G7CVIM, and ADC14-0810 (Erbitux(LC)-G7CVIM-LBG-MMAF) as primary antibodies. Cells labeled with anti-human IgG$_1$ as the primary antibody or without an antibody, were used as negative controls. Each anti-EGFR antibody bound to A431 cells, resulting in similar labeling relative to the negative controls.

The ADC14-0810 antibody bound to A431 cells, resulting in fluorescence intensity that was comparable to cetuximab and Erbitux(LC)-G7CVIM (FIG. 11).

TABLE 7

FIG. 11 Flow cytometry Parameters

| Filename | Parameter | Low Bound | High Bound | # of events | % of gated cells |
|---|---|---|---|---|---|
| cell only.fcs | PE-A | 1 | 9910 | 9669 | 100.0 |
| Erbitux.fcs | PE-A | 1 | 9910 | 9697 | 100.0 |
| Erbitux G7-CVIM(LC).fcs | PE-A | 1 | 9910 | 9672 | 100.0 |
| ADC14-0810(Erbitux ADC).fcs | PE-A | 1 | 9910 | 9696 | 100.0 |
| hIgG.fcs | PE-A | 1 | 9910 | 9684 | 100.0 |

| Filename | Median | Geometric Mean | CV | Peak Value | Peak Channel |
|---|---|---|---|---|---|
| cell only.fcs | 11.76 | 11.7 | 204.02 | 85.0 | 10.84 |
| Erbitux.fcs | 166.98 | 150.39 | 90.71 | 62.0 | 176.24 |
| Erbitux G7-CVIM(LC).fcs | 176.24 | 160.11 | 76.47 | 69.0 | 192.82 |
| ADC14-0810(Erbitux ADC).fcs | 170.01 | 152.93 | 72.46 | 66.0 | 159.63 |
| hIgG.fcs | 11.44 | 10.93 | 67.64 | 100.0 | 11.44 |

Example 16. Cytotoxicity of Cetuximab (LC)-Glucuronide Linker-MMAF (ADC14-0810)

Figure 12:
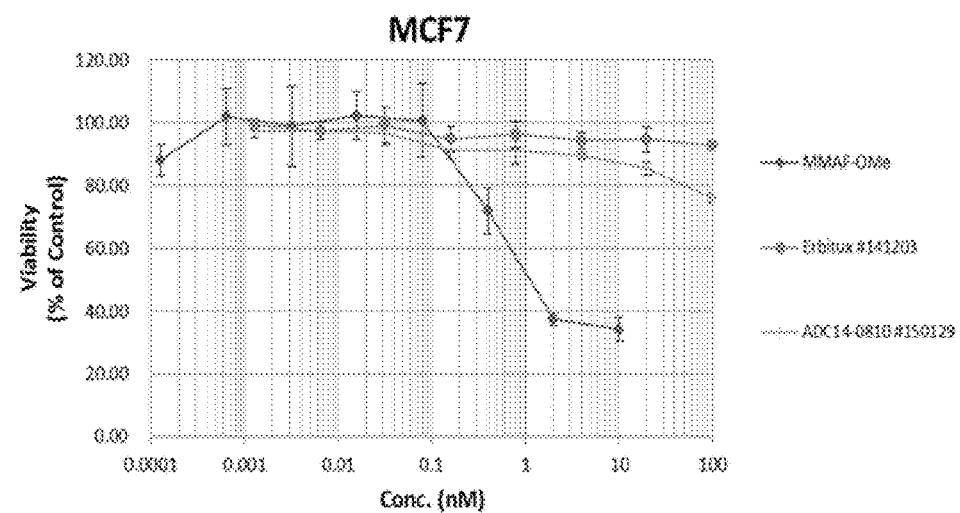
FIG. 12 consists of three panels, labeled panel (A), (B), and (C).
Figure 12:
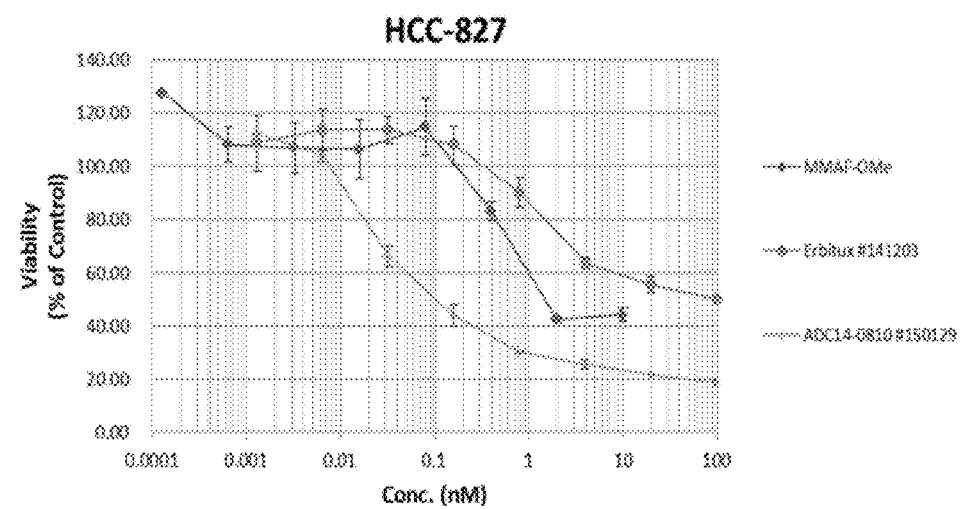
Figure 12:
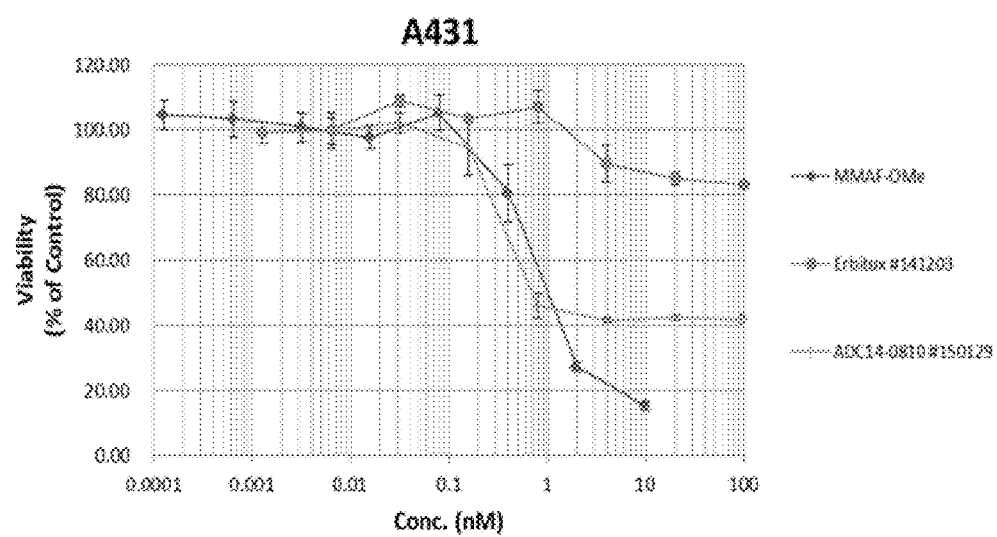

A431 cells, which express high levels of EGFR, and MCF-7 cells, which express low levels of EGFR, were plated at about 1000 cells per well in a 96-well plate in 100 µL of media. HCC-827 cells, which express an intermediate level of EGFR were plated at about 500 cells per well in a 96-well plate in 100 µL of media. The cells were incubated at 37° C. in 5% CO$_2$ for 24 hours. Then, serial dilutions of monomethyl auristatin F-Ome (MMAF-Ome), Erbitux(LC)-G7CVIM, and the antibody-drug conjugate ADC14-0810 (comprising Erbitux(LC)-G7CVIM and MMAF) were added to the cells at concentrations of 100 to 0.00128 nM. The cells were incubated for 72 hours and then fixed for 1 hour at 4° C. after adding 100 µL of ice-cold 10% tricholoracetic acid to each well. Viable cells were counted using SRB dye (Sulphorhodamine, Sigma S 1402) and a Molecular Devices SpectraMax 190 plate reader running Softmax Pro v5, monitoring absorbance at 540 nm (FIG. 12).

Erbitux(LC)-G7CVIM had an $IC_{50}$ greater than 100 nM for each cell line (Table 8) (A431, MCF-7, and HCC-827). MMAF-Ome had an $IC_{50}$ of 1.81 nM against MCF-7 cells, 1.99 nM against HCC-827 cells, and 1.11 nM against A431 cells. The antibody-drug conjugate ADC12-810 had an $IC_{50}$ of greater than 100 nM against MCF-7 cells, 0.25 nM against HCC-827 cells, and 6.54 nM against A431 cells, thus displaying superior specificity over MMAF-Ome and superior potency over Erbitux(LC)-G7CVIM (FIG. 12).

TABLE 8

$IC_{50}$ Values

| Sample | MCF7 (EGFR low) | HCC-827 (EGFR Intermediate: del E746_A750) | A431 (EGFR high) |
|---|---|---|---|
| MMAF-Ome | 1.81 | 1.99 | 1.11 |
| Erbitux G7-CVIM | >100 | >100 | >100 |
| ADC14-0810 | >100 | 0.25 | 6.54 |

Example 17. Pharmacokinetics of Cetuximab (LC)-Glucuronide Linker-MMAF (ADC14-0810)

Male Sprague Dawley rats were dosed intravenously with 3 mg/kg of cetuximab (Erbitux®) or the antibody-drug conjugate ADC14-0810. Blood samples were taken at multiple time points after dosing, chilled in ice water, and plasma was isolated. Plasma was frozen at −80° C. until subsequent LC/MS/MS analysis.

20 µL of each sample was mixed with 340 µL of PBS and 60 µL of protein A magnetic beads and incubated for 2 hours at room temperature with gentle shaking. The beads were washed three time with PBS. Then, 25 µL of an internal standard (isotope-labeled peptides at 10 µg/mL), 75 µL of RapiGest SF (Waters), and 10 µL of dithiothreitol were added to the beads. The mixture was shaken for 1 minute and then incubated for 1 hour at 60° C. 25 µL of iodoacetic acid was added to the mixture, the mixture was shaken for 1 minute, and then incubated for 30 minutes at room temperature. 10 µL of sequencing grade modified trypsin (Promega) was added to the mixture, the mixture was shaken for 1 minute, and the mixture was incubated overnight at 37° C. 15 µL of hydrochloric acid was added to the mixture, the mixture was shaken for 1 minute, and the mixture was incubated for 30 minutes at 37° C. The mixture was centrifuged at 5000×G for 10 minutes at 4° C. and the supernatant was transferred into an HPLC vial.

The liquid chromatography-mass spectrometry system consisted of two Shimadzu LC-20AD pumps, a Shimadzu CBM-20A HPLC pump controller (Shimadzu Corporation, Columbia, Md., USA), a CTC HTS PAL autosampler (CEAP Technologies, Carrboro, N.C., USA) and a triple time of flight 5600 mass spectrometer (Triple TOF MS) (AB Sciex, Foster City, Calif., USA). The analytical column was a Phenomenex Kinetex XB-C18 column, 2.1×30 (2.6 um). HPLC was performed with a water/acetonitrile gradient and acidified with 0.1% formic acid. Injection volumes were 10 µL. Triple TOF MS, equipped with a Duospray™ ion source, was used to complete the high resolution experiment. The Triple TOF MS was operated in the positive ion mode. High-purity nitrogen gas was used for the nebulizer/Duospray™ and curtain gases. The source temperature was set at 500° C. with a curtain gas flow of 30 L/min. The ion spray voltage was set at 5500 V, declustering potential was 145 V, and the collision energy was 38 V. The product ion mode was used as scan mode. Analyst® TF Version 1.6 (AB Sciex) operated with Windows® (Microsoft) was used for instrument control and data acquisition. Peak integrations were performed with MultiQuant® Version 2.1.1 (AB Sciex). Calculations were performed with MultiQuant® Version 2.1.1 for peak area ratios, standard curve regressions, sample concentration values, and descriptive statistics. The LC/MS/MS was calibrated using cetuximab standard solutions at concentrations of 0.1, 0.4, 1, 2, 5, 10, 20, 40, 80, and 100 µg/mL.

Figure 13:
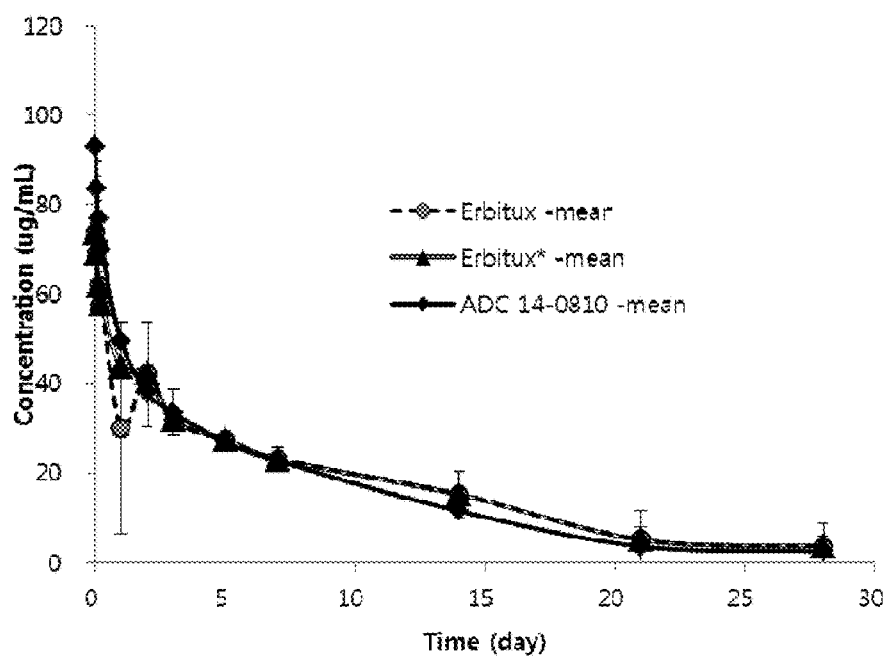
FIG. 13 shows pharmacokinetics results for cetuximab (Erbitux®) and the antibody-drug conjugate ADC14-0810, comprising cetuximab and MMAF. The half-life for ADC14-0810 was calculated to be 6.35 days, which was similar to cetuximab.
Figure 14:
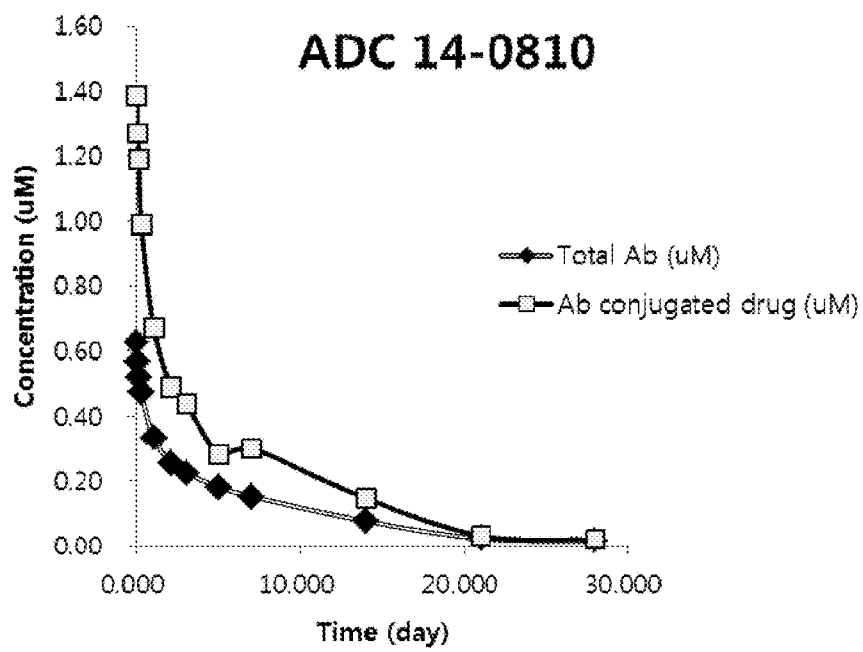
FIG. 14 consists of two panels, labeled panel (A) and (B).
Figure 14:
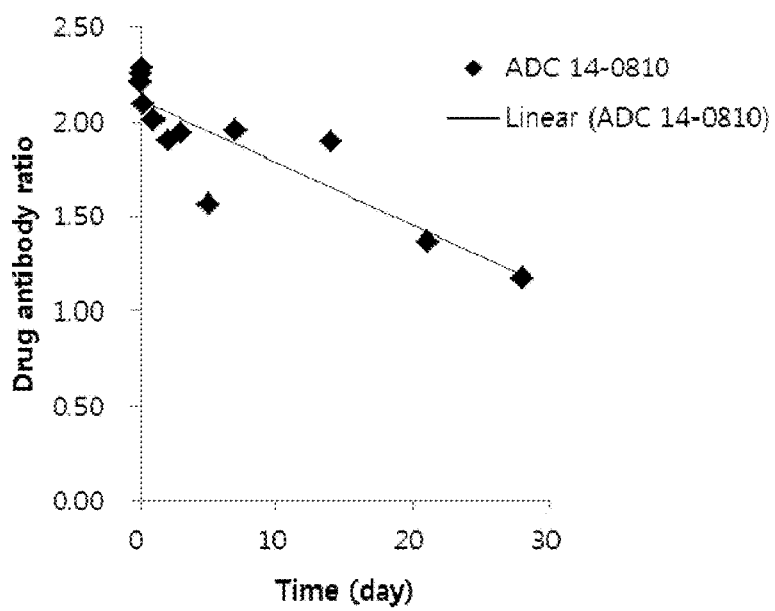

The pharmacokinetics analysis suggested that ADC14-0810 has a half-life of 6.35 days, which was comparable to the half-life calculated for cetuximab (FIG. 13).

TABLE 9

PK parameters using WinNonlin Phoenix 6.3
PK parameters using WinNonlin Phoenix 6.3

| | AUC (ug*/day/ml) | Cl (mL/day/kg) | Alpha HL (day) | Beta HL (day) |
|---|---|---|---|---|
| Erbitux | 503.39 ± 43.21 | 5.96 ± 0.51 | 0.19 ± 0.10 | 8.21 ± 0.99 |
| Erbitux* | 504.13 ± 24.41 | 5.95 ± 0.29 | 0.22 ± 0.09 | 7.41 ± 0.51 |
| ADC14-0810 | 454.46 ± 14.67 | 6.60 ± 0.21 | 0.32 ± 0.07 | 6.35 ± 0.32 |

| | Cmax (ug/ml) | V1 (ml/kg) | Vss (ml/kg) | Compartment model |
|---|---|---|---|---|
| Erbitux | 74.65 ± 5.42 | 40.19 ± 2.92 | 69.30 ± 5.13 | 2 |
| Erbitux* | 72.92 ± 3.21 | 41.14 ± 1.81 | 62.60 ± 2.72 | 2 |
| ADC14-0810 | 89.33 ± 2.25 | 33.58 ± 0.85 | 58.00 ± 1.89 | 2 |

*PK parameters were recalculated excluding the value measured at day 1, which was an outlier.

Example 18. Stability of Cetuximab (LC)-Glucuronide Linker-MMAF (ADC14-0810)

The drug-antibody ratio (DAR) was calculated for drug that was conjugated to cetuximab from the rat plasma samples obtained in Example 17. Frozen samples were thawed and mixed with 150 µL of protein A magnetic beads in PBS. The beads were washed three times, and 10 µL of PBS and 30 µL of beta-glucuronidase (1 mg/mL, Sigma G7396) were added to release MMAF from the antibody. The beads were incubated with beta-glucuronidase for 2 hours at 37° C. 40 µL of 30% acetonitrile in 1% formic acid was added to each beta-glucuronidase reaction, the mixture for each sample was centrifuged at 5000×G for 5 minutes, and the supernatant of each sample was loaded into HPLC vials. ADC14-0810 standards at 0.1, 0.5, 1, 2, 5, 10, 20, 40, 80, and 100 µg/mL in monkey plasma were prepared in parallel. The beta-glucuronidase-treated samples and standards were analyzed by LC/MS/MS using methods similar to those described in Example 17.

Rat plasma samples taken at 1 to 14 days displayed a drug-antibody ratio of about 2:1, consistent with MMAF bound to each of the two cetuximab light chains. The calculated drug-antibody ratio was 1.96 at 7 days, 1.90 at 14 days, 1.36 at 21 days, and 1.17 at 28 days (FIG. 13).

INCORPORATION BY REFERENCE

Each of the patents, published patent applications, and non-patent references cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An antibody drug conjugate, having the structure of Formula I:

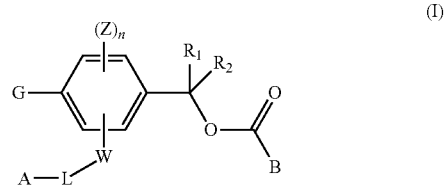

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Gly Gly Gly Cys Val Ile Met
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Val Ile Met
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Val Leu Leu
1
``` wherein:

G is a glucuronic acid moiety or

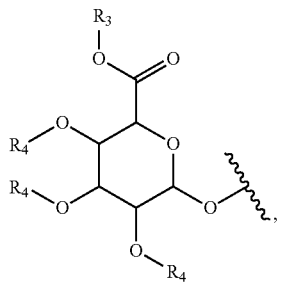

wherein R3 is hydrogen or a carboxyl protecting group; and each $R_4$ is independently hydrogen or a hydroxyl protecting group;

A represents an anti-EGFR antibody;

B represents an active agent;

W is —C(O)—, —C(O)NR'—, —C(O)O—, —S(O)₂NR'—, —P(O)R"NR'—, —S(O)NR'—, or —PO₂NR'—, in each case where the C(O), S, or P is directly bound to the phenyl ring, and R' and R" are each independently hydrogen, $(C_1-C_8)$alkyl, $(C_3-C_8)$cycloalkyl, $(C_1-C_8)$alkoxy, $(C_1-C_8)$alkylthio, mono- or di-$(C_1-C_8)$alkylamino, $(C_3-C_{20})$heteroaryl, or $(C_6-C_{20})$aryl;

each Z independently represents hydrogen, $(C_1-C_8)$alkyl, halogen, cyano, or nitro;

n is an integer from 1 to 3;

L comprises an alkylene chain of 3 to 50 atoms that covalently links A to W, wherein the chain further comprises an oxime and either:
  (a) the oxygen atom of the oxime is substituted with a group that covalently links the oxime to W; and the carbon atom of the oxime is substituted with a group that covalently links the oxime to A; or
  (b) the carbon atom of the oxime is substituted with a group that covalently links the oxime to W; and the oxygen atom of the oxime is substituted with a group that covalently links the oxime to A;

$R_1$ and $R_2$ are each independently hydrogen, $(C_1-C_8)$alkyl, or $(C_3-C_8)$cycloalkyl, or $R_1$ and $R_2$ taken together with the carbon atom to which they are attached form a $(C_3-C_8)$cycloalkyl ring; and the moieties connecting A and B, taken together, form the linker.

2. The antibody-drug conjugate of claim 1, wherein W represents —C(O)NR'—, wherein C(O) is bonded to the phenyl ring and NR' is bonded to L.

3. The antibody-drug conjugate of claim 1, wherein the linker comprises at least one isoprenyl unit, represented by

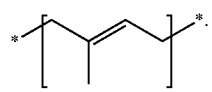

4. The antibody-drug conjugate of claim 3, wherein the isoprenyl unit covalently links the oxime to the antibody.

5. The antibody-drug conjugate of claim 4, wherein the linker comprises:

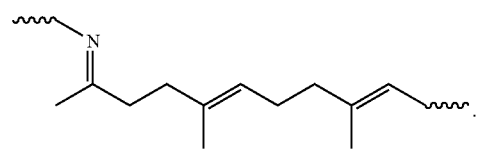

6. The antibody-drug conjugate of claim 1, wherein the linker comprises at least one polyethylene glycol unit, represented by

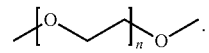

7. The antibody-drug conjugate of claim 6, wherein the linker comprises an oxime, and the at least one polyethylene glycol unit covalently links the oxime to the active agent.

8. The antibody-drug conjugate of claim 2, wherein the linker comprises a connection unit represented by —$(CH_2)_r(V(CH_2)_p)_q$—, wherein:

r is an integer of 1 to 10;
p is an integer of 0 to 10;
q is an integer of 1 to 10;
V is a single bond, —O—, —S—, —$NR_{21}$—, —C(O)$NR_{22}$—, —$NR_{23}$C(O)—, —$NR_{24}SO_2$—, or —$SO_2NR_{25}$—; and
$R_{21}$ to $R_{25}$ are each independently hydrogen, $(C_1-C_6)$alkyl, $(C_1-C_6)$alkyl$(C_6-C_{20})$aryl, or $(C_1-C_6)$alkyl$(C_3-C_{20})$heteroaryl.

9. The antibody-drug conjugate of claim 1, wherein the linker comprises a connection unit represented by $(CH_2CH_2X)_w$—, wherein:

X represents —O—, $(C_1-C_8)$alkylene, or —$NR_{21}$—;
$R_{21}$ represents hydrogen, $(C_1-C_6)$alkyl, $(C_1-C_6)$alkyl$(C_6-C_{20})$aryl, or $(C_1-C_6)$alkyl$(C_3-C_{20})$heteroaryl; and
w is an integer of 1 to 10.

10. The antibody-drug conjugate of claim 1, wherein the linker comprises a linking moiety formed by a 1,3-dipolar cycloaddition reaction, hetero-Diels-Alder reaction, nucleophilic substitution reaction, non-aldol type carbonyl reaction, addition to carbon-carbon multiple bond, oxidation reaction, or click reaction.

11. The antibody-drug conjugate of claim 10, wherein the linking moiety is represented by any one of Formulas A, B, C, or D:

(A)
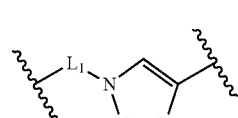

(B)
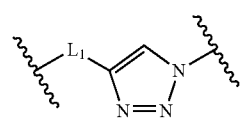

(C)
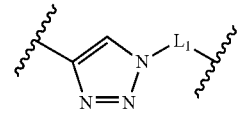

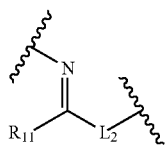
(D)

wherein:
L₁ is a single bond or alkylene having 1 to 30 carbon atoms;
R₁₁ is hydrogen or alkyl having 1 to 10 carbon atoms; and
L₂ is alkylene having 1 to 30 carbon atoms.

12. The antibody-drug conjugate of claim 11, wherein: the linker comprises

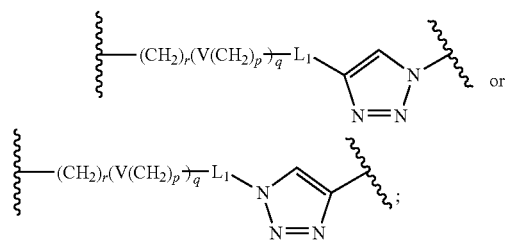

V is a single bond, —O—, —S—, —NR₂₁—, —C(O)NR₂₂—, —NR₂₃C(O)—, —NR₂₄SO₂—, or —SO₂NR₂₅—;
R₂₁ to R₂₅ are each independently hydrogen, (C₁-C₆) alkyl, (C₁-C₆)alkyl(C₆-C₂₀)aryl, or (C₁-C₆)alkyl(C₃-C₂₀)heteroaryl;
r is an integer of 1 to 10;
p is an integer of 0 to 10;
q is an integer of 1 to 10; and
L₁ is a single bond.

13. The antibody-drug conjugate of claim 1, comprising the structure of Formula III:

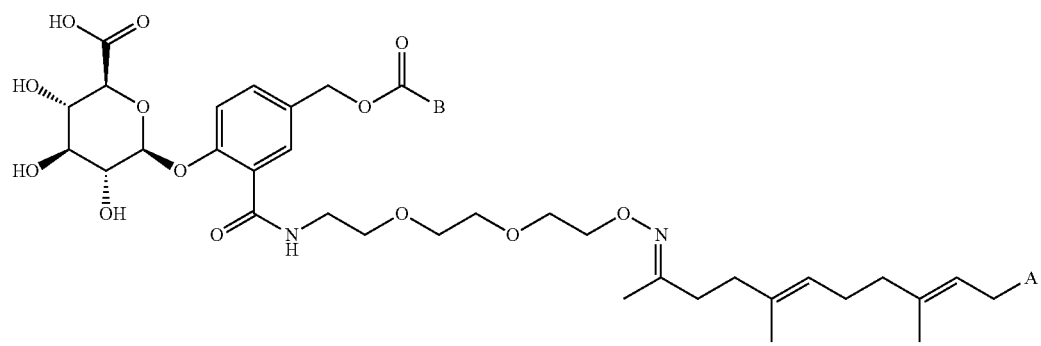

(III)

wherein A represents the antibody; and B represents the active agent.

14. The antibody-drug conjugate of claim 1, wherein the linker is covalently bound to the antibody by a thioether bond, and the thioether bond comprises a sulfur atom of a cysteine of the antibody.

15. The antibody-drug conjugate of claim 1, wherein the antibody is a monoclonal antibody, polyclonal antibody, antibody fragment, Fab, Fab', Fab'-SH, F(ab')₂, Fv, single chain Fv ("scFv"), diabody, linear antibody, bispecific antibody, multispecific antibody, chimeric antibody, humanized antibody, human antibody, or fusion protein comprising the antigen-binding portion of an antibody.

16. The antibody-drug conjugate of claim 1, wherein the antibody can specifically bind an extracellular epitope on EGFR.

17. The antibody-drug conjugate of claim 1, wherein the active agent is a chemotherapeutic agent or a toxin.

18. The antibody-drug conjugate of claim 1, wherein the active agent is selected from:
(a) erlotinib, bortezomib, fulvestrant, sutent, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, trietylenephosphoramide, triethiylenethiophosphoramide, trimethylolomelamine, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, antrmycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubucin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2''-trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;
(b) monokine, a lymphokine, a polypeptide hormone, parathyroid hormone, thyroxine, relaxin, prorelaxin, a glycoprotein hormone, follicle stimulating hormone, thyroid stimulating hormone, luteinizing hormone, hepatic growth factor fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-α, interferon-β, interferon-γ, a colony stimulating factor ("CSF"), macrophage-CSF, granulocyte-macrophage-CSF, granulocyte-CSF, an interleukin ("IL"), IL-1, IL-1a, IL-2, IL-3, IL-4, IL-5, IL-6, IL-7, IL-8, IL-9, IL-10, IL-11, IL-12, a tumor necrosis factor, TNF-α, TNF-β, a polypeptide factor, LIF, kit ligand, or a combination of any of the foregoing;
(c) diphtheria toxin, botulium toxin, tetanus toxin, dysentery toxin, cholera toxin, amanitin, α-amanitin, pyrrolobenzodiazepine, tetrodotoxin, brevetoxin, ciguatoxin, ricin, AM toxin, auristatin, tubulysin, geldanamycin, maytansinoid, calicheamycin, daunomycin, doxorubicin, methotrexate, vindesine, SG2285, dolastatin, auristatin, cryptophycin, camptothecin, rhizoxin, CC-1065, duocarmycin, an enediyne antibiotic, esperamicin, epothilone, a toxoid, or a combination of any of the foregoing;
(d) an affinity ligand, wherein the affinity ligand is a substrate, an inhibitor, a stimulating agent, a neurotransmitter, a radioisotope, or a combination of any of the foregoing;
(e) a radioactive label, $^{32}$P, $^{35}$S, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;
(f) an immunomodulatory compound, an anti-cancer agent, an anti-viral agent, an anti-bacterial agent, an anti-fungal agent, and an anti-parasitic agent, or a combination of any of the foregoing;
(g) tamoxifen, raloxifene, droloxifene, 4-hydroxytamoxifen, trioxifene, keoxifene, LY117018, onapristone, or toremifene;
(h) 4(5)-imidazoles, aminoglutethimide, megestrol acetate, exemestane, letrozole, or anastrozole;
(i) flutamide, nilutamide, bicalutamide, leuprolide, goserelin, or troxacitabine;
(j) an aromatase inhibitor;
(k) a protein kinase inhibitor;
(l) a lipid kinase inhibitor;
(m) an antisense oligonucleotide;
(n) a ribozyme;
(o) a vaccine; and
(p) an anti-angiogenic agent.

19. The antibody-drug conjugate of claim 1, wherein the active agent is amanitin, auristatin, calicheamicin, camptothecin, cryptophycin, daunomycin, dolastatin, doxorubicin, duocarmycin, epothilone, esperamicin, geldanamycin, maytansinoid, methotrexate, monomethyl auristatin E ("MMAE"), monomethyl auristatin F ("MMAF"), pyrrolobenzodiazepine, rhizoxin, SG2285, tubulysin, vindesine, or toxoid.

20. The antibody-drug conjugate of claim 1, wherein B is:

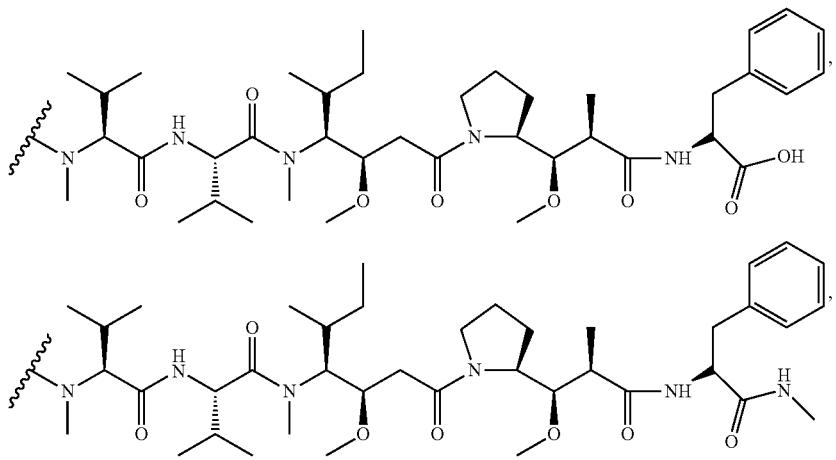

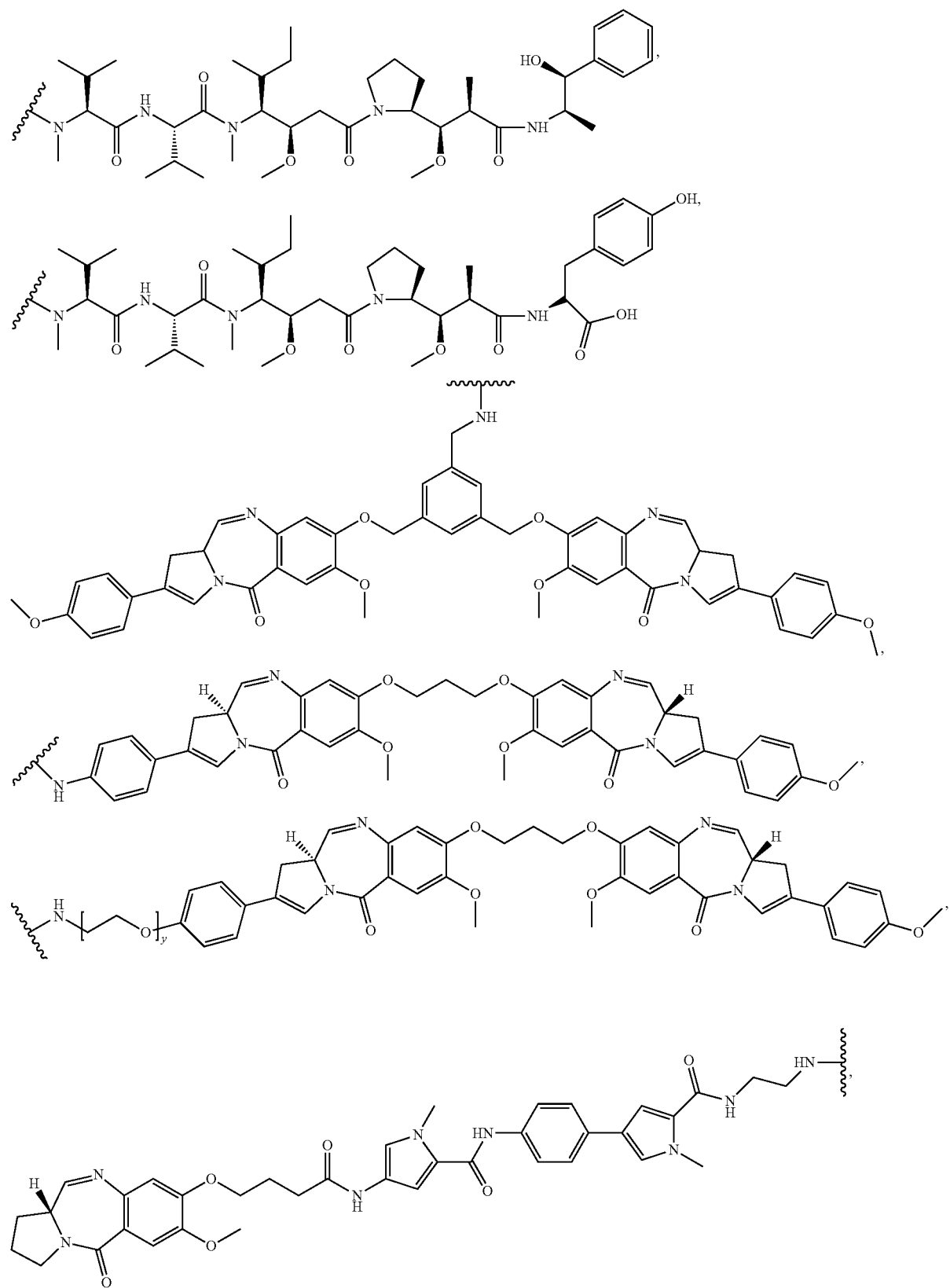

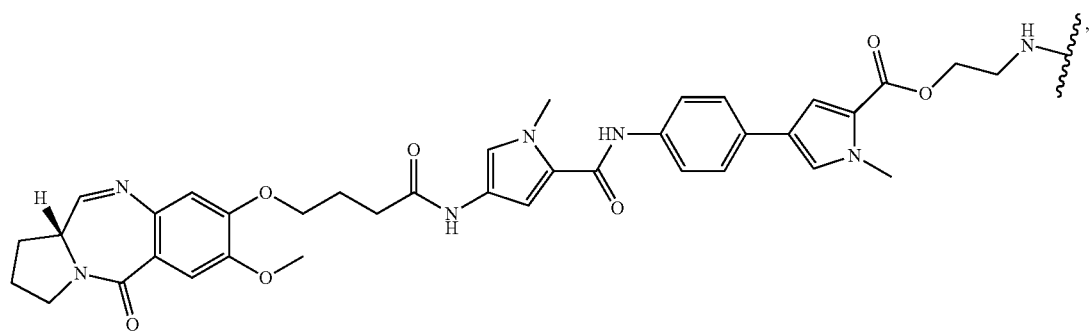
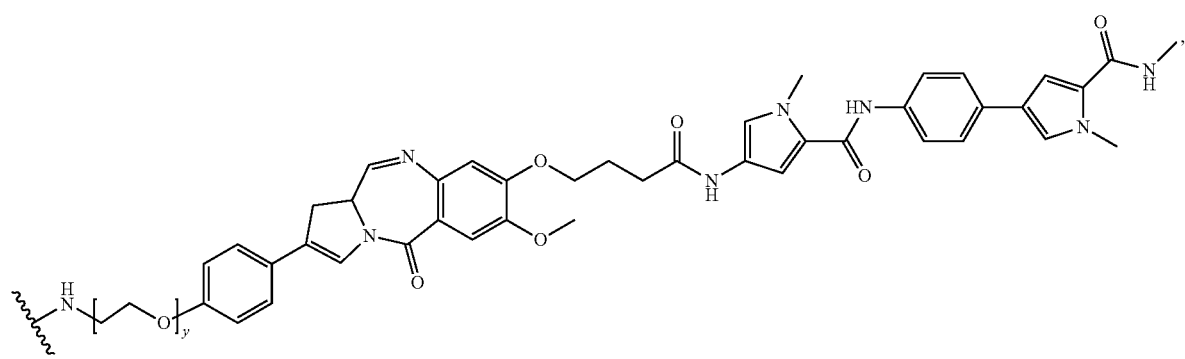
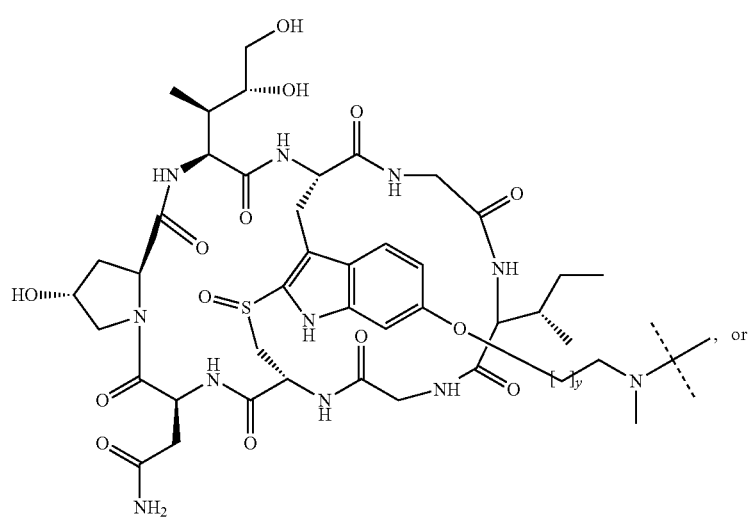

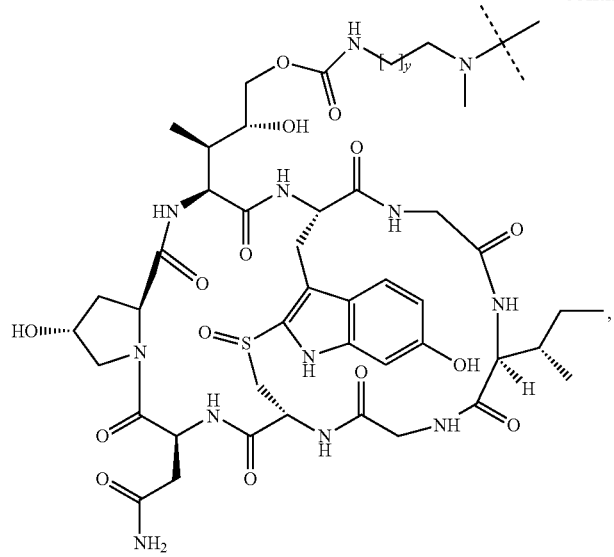

wherein y is an integer of 1 to 10.

21. A pharmaceutical composition comprising the antibody-drug conjugate of claim 1.

22. A method of treating cancer in a subject, comprising administering the pharmaceutical composition of claim 21 to the subject.

23. The antibody-drug conjugate of claim 8, wherein the linker comprises at least one isoprenyl unit, represented by

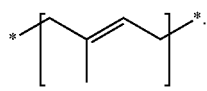

24. The antibody-drug conjugate of claim 9, wherein the linker comprises at least one isoprenyl unit, represented by

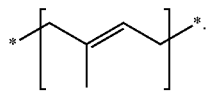

25. The antibody-drug conjugate of claim 11, wherein the linker comprises at least one isoprenyl unit, represented by

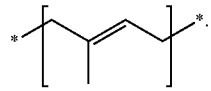

26. The antibody-drug conjugate of claim 1, wherein L satisfies at least one of the following (i) to (iii):

(i) the alkylene includes at least one unsaturated bond,
(ii) the alkylene includes at least one heteroarylene,
(iii) the alkylene is substituted with one or more alkyls having 1 to 20 carbon atoms.

* * * * *

UNITED STATES PATENT AND TRADEMARK OFFICE
CERTIFICATE OF CORRECTION

PATENT NO. : 10,118,965 B2
APPLICATION NO. : 15/276231
DATED : November 6, 2018
INVENTOR(S) : Yong Zu Kim et al.

Page 1 of 1

It is certified that error appears in the above-identified patent and that said Letters Patent is hereby corrected as shown below:

In the Claims

In Column 61, Lines 17-19, Claim 1, cancel the text "wherein R3 is hydrogen or a carboxyl protecting group; and each $R_4$ is independently hydrogen or a hydroxyl protecting group;" and insert:
--wherein $R_3$ is hydrogen or a carboxyl protecting group; and each $R_4$ is independently hydrogen or a hydroxyl protecting group;--

In Column 62, Lines 12-17, Claim 6, cancel the text " 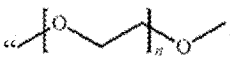 " and insert:

-- 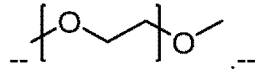 .--

Signed and Sealed this
Seventh Day of May, 2019

Andrei Iancu
*Director of the United States Patent and Trademark Office*